US007910805B2

(12) United States Patent
Duck et al.

(10) Patent No.: US 7,910,805 B2
(45) Date of Patent: Mar. 22, 2011

(54) BACTERIAL GLUTAMINE SYNTHETASES AND METHODS OF USE

(75) Inventors: Nicholas B. Duck, Apex, NC (US);
Todd K. Hinson, Rougemont, NC (US);
Vadim Beilinson, Cary, NC (US); Laura Cooper Schouten, Pittsboro, NC (US);
Daniel John Tomso, Bahama, NC (US)

(73) Assignee: Athenix Corp., Morrisville, NC (US)

( * ) Notice: Subject to any disclaimer, the term of this patent is extended or adjusted under 35 U.S.C. 154(b) by 704 days.

(21) Appl. No.: 11/760,602

(22) Filed: Jun. 8, 2007

(65) Prior Publication Data

US 2009/0018016 A1 Jan. 15, 2009

Related U.S. Application Data

(60) Provisional application No. 60/812,000, filed on Jun. 8, 2006.

(51) Int. Cl.
*C12N 15/52* (2006.01)
*C12N 15/82* (2006.01)

(52) U.S. Cl. .......... 800/300; 435/252.3; 435/320.1; 435/419; 536/23.2; 800/288; 800/298; 800/302

(58) Field of Classification Search .......... None
See application file for complete search history.

(56) References Cited

U.S. PATENT DOCUMENTS

| | | | | |
|---|---|---|---|---|
| 5,098,838 A * | 3/1992 | Goodman et al. | | 435/183 |
| 5,145,777 A | 9/1992 | Goodman et al. | | |
| 5,646,024 A | 7/1997 | Leemans et al. | | |
| 5,739,082 A | 4/1998 | Donn | | |
| 5,955,651 A * | 9/1999 | Coruzzi et al. | | 800/298 |
| 6,107,547 A | 8/2000 | Coruzzi et al. | | |
| 7,041,814 B1 * | 5/2006 | Weinstock et al. | | 536/24.1 |
| 2003/0041357 A1 * | 2/2003 | Jepson et al. | | 800/300 |

OTHER PUBLICATIONS

Stadtman et al 1970, Advances in Enzyme Regulation vol. 8, pp. 99-118 (abstract only).*
DIR 012/2002 Risk Assessment and Risk Management Plan, "Commercial release of Bollgard II cotton", Sep. 2002, Australian Office of the Gene Technology Regulator.*
Crespo, J.L., et al., "Mutational Analysis of Asp51 of *Anabaena azollae* Glutamine Synthetase. D51E Mutation Confers Resistance to the Active Site Inhibitors L-methionine-DL-sulfoximine and Phosphinothricin," *Eur. J. Biochem.*, Feb. 1999, pp. 1202-1209, vol. 266.
Mehta, R., et al., "Adenylylation and Catalytic Properties of *Mycobacterium tuberculosis* Glutamine Synthetase Expressed in *Escherichia coli* versus Mycobacteria," *J. Biol. Chem.*, May 21, 2004, pp. 22477-22482, vol. 279, No. 21.
Yamamoto, S., et al., "Cloning and Expression of *Pseudomonas taetrolens* Y-30 Gene Encoding Glutamine Synthetase: An Enzyme Available for Theanine Production by Coupled Fermentation with Energy Transfer," *Biosci. Biotechnol. Biochem.*, 2006, pp. 500-507, vol. 70, No. 2.
NCBI Database Report for Accession No. AAN37400, Direct Submission on Aug. 27, 2002.
NCBI Database Report for Accession No. CAG72951, Direct Submission on Feb. 18, 2004.
NCBI Database Report for Accession No. NP_290495, Direct Submission on Sep. 28, 2001.
NCBI Database Report for Accession No. ZP_00824355, Direct Submission on Oct. 20, 2005.
McClelland, M. et al., "Complete Genome Sequence of *Salmonella enterica* serovar Typhimurium LT2," *Nature*, Oct. 25, 2001, pp. 852-856, vol. 413, No. 6858.
Miller, E.S., and J.E. Brenchley, "1-Methionine *SR*-Sulfoximine-resistant Glutamine Synthetase from Mutants of *Salmonella typhimurium*," *J. Biol. Chem.*, Nov. 10, 1981, pp. 11307-11312, vol. 256, No. 21.
EMBL Database Report for Accession No. AE008887, Oct. 29, 2001.

* cited by examiner

*Primary Examiner* — David H Kruse
(74) *Attorney, Agent, or Firm* — Destiny M. Davenport

(57) ABSTRACT

Compositions and methods for conferring herbicide resistance to and improving nitrogen utilization of bacteria, plants, plant cells, tissues and seeds are provided. Compositions comprising a coding sequence for a polypeptide that confers resistance or tolerance to herbicidal glutamine synthetase inhibitors are provided. The coding sequences can be used in DNA constructs or expression cassettes for transformation and expression in plants. Compositions also comprise transformed bacteria, plants, plant cells, tissues, and seeds. In particular, isolated polynucleotides corresponding to herbicidal glutamine synthetase inhibitor-resistant polynucleotides are provided. Additionally, polypeptides corresponding to the polynucleotides are encompassed. In particular, the present invention provides for isolated polynucleotides comprising a variant of SEQ ID NO:1, wherein the variant polynucleotide encodes a polypeptide that is resistant to inhibition by herbicidal glutamine synthetase inhibitor.

62 Claims, 3 Drawing Sheets

|  | 420 | 440 | 460 |  |
|---|---|---|---|---|
| AGS-1 | : GSLDEAMAALNEDREFLTRGGVPTDDAIDAYIELRKEEMDRVRMTPHPVEFELYYSV- | : 469 |
| pAX3421m1 | : ............................................................ | : 469 |
| pAX3422m2 | : ............................................................ | : 469 |
| pAX3427m3 | : ............................................................ | : 469 |
| pAX3428m4 | : ............................................................ | : 469 |
| pAX3430m6 | : ............................................................ | : 469 |
| pAX3431m7 | : ............................................................ | : 469 |
| pAX3432m8 | : ............................................................ | : 469 |
| pAX3433m9 | : .....................C...................................... | : 469 |
| pAX3434m10 | : ............................................................ | : 469 |
| pAX3435m11 | : ............................................................ | : 469 |
| pAX3436m12 | : ............................................................ | : 469 |
| pAX3437m13 | : ............................................................ | : 469 |
| pAX3438m14 | : ........V................................................... | : 469 |
| pAX3426m15 | : ............................................................ | : 469 |
| pAX3439m16 | : ............................................................ | : 469 |

SEQUENCE LISTING

<160> NUMBER OF SEQ ID NOS: 47

<210> SEQ ID NO 1
<211> LENGTH: 1410
<212> TYPE: DNA
<213> ORGANISM: Serratia marcescens
<220> FEATURE:
<221> NAME/KEY: CDS
<222> LOCATION: (1)...(1410)

<400> SEQUENCE: 1

| | | | | | | | | | | | | | | | | |
|---|---|---|---|---|---|---|---|---|---|---|---|---|---|---|---|---|
| atg | tcc | gct | gaa | cac | gtt | ttg | acg | atg | ctg | aat | gag | cat | gaa | gtg | aaa | 48 |
| Met | Ser | Ala | Glu | His | Val | Leu | Thr | Met | Leu | Asn | Glu | His | Glu | Val | Lys | |
| 1 | | | | 5 | | | | | 10 | | | | | 15 | | |
| ttc | gta | gac | ctg | cgt | ttc | act | gac | acc | aag | ggt | aag | gaa | cag | cac | gtg | 96 |
| Phe | Val | Asp | Leu | Arg | Phe | Thr | Asp | Thr | Lys | Gly | Lys | Glu | Gln | His | Val | |
| | | 20 | | | | | 25 | | | | | 30 | | | | |
| act | atc | ccg | gct | cac | cag | gta | aac | gcc | gac | ttc | ttc | gaa | gaa | ggt | aaa | 144 |
| Thr | Ile | Pro | Ala | His | Gln | Val | Asn | Ala | Asp | Phe | Phe | Glu | Glu | Gly | Lys | |
| | 35 | | | | | 40 | | | | | 45 | | | | | |
| atg | ttt | gac | ggc | tcc | tct | atc | ggt | ggt | tgg | aag | ggc | atc | aac | gaa | tct | 192 |
| Met | Phe | Asp | Gly | Ser | Ser | Ile | Gly | Gly | Trp | Lys | Gly | Ile | Asn | Glu | Ser | |
| 50 | | | | | 55 | | | | | 60 | | | | | | |
| gac | atg | gtg | ctg | atg | ccg | gac | gcc | agc | acg | gcg | gtt | ctg | gat | ccg | ttc | 240 |
| Asp | Met | Val | Leu | Met | Pro | Asp | Ala | Ser | Thr | Ala | Val | Leu | Asp | Pro | Phe | |
| 65 | | | | | 70 | | | | | 75 | | | | | 80 | |
| ttc | gaa | gaa | cct | acg | ctg | atc | att | cgc | tgt | gac | att | ctc | gag | ccg | ggc | 288 |
| Phe | Glu | Glu | Pro | Thr | Leu | Ile | Ile | Arg | Cys | Asp | Ile | Leu | Glu | Pro | Gly | |
| | | | | 85 | | | | | 90 | | | | | 95 | | |
| acc | atg | caa | ggc | tac | gat | cgc | gac | ccg | cgt | tcc | atc | tcc | aaa | cgc | gcc | 336 |
| Thr | Met | Gln | Gly | Tyr | Asp | Arg | Asp | Pro | Arg | Ser | Ile | Ser | Lys | Arg | Ala | |
| | | | 100 | | | | | 105 | | | | | 110 | | | |
| gaa | gac | ttc | ctg | cgc | tcc | tcc | ggc | atc | gcg | gac | acc | gtg | ctg | ttc | ggg | 384 |
| Glu | Asp | Phe | Leu | Arg | Ser | Ser | Gly | Ile | Ala | Asp | Thr | Val | Leu | Phe | Gly | |
| | | 115 | | | | | 120 | | | | | 125 | | | | |
| cca | gag | cct | gag | ttc | ttc | ctg | ttc | gac | gac | atc | cgc | ttc | ggc | agc | agc | 432 |
| Pro | Glu | Pro | Glu | Phe | Phe | Leu | Phe | Asp | Asp | Ile | Arg | Phe | Gly | Ser | Ser | |
| | 130 | | | | | 135 | | | | | 140 | | | | | |
| atc | cgc | ggt | tcc | cac | gtg | gcg | atc | gac | gat | atc | gaa | ggc | gcc | tgg | aac | 480 |
| Ile | Arg | Gly | Ser | His | Val | Ala | Ile | Asp | Asp | Ile | Glu | Gly | Ala | Trp | Asn | |
| 145 | | | | | 150 | | | | | 155 | | | | | 160 | |
| tcc | ggc | aca | aaa | tac | gac | ggc | ggc | aac | aaa | ggc | cac | cgt | ccg | gcg | gtg | 528 |
| Ser | Gly | Thr | Lys | Tyr | Asp | Gly | Gly | Asn | Lys | Gly | His | Arg | Pro | Ala | Val | |
| | | | 165 | | | | | 170 | | | | | 175 | | | |
| aaa | ggc | ggt | tac | ttc | ccg | gtt | cca | ccg | gtc | gac | tct | tcg | cag | gat | ctg | 576 |
| Lys | Gly | Gly | Tyr | Phe | Pro | Val | Pro | Pro | Val | Asp | Ser | Ser | Gln | Asp | Leu | |
| | | 180 | | | | | 185 | | | | | 190 | | | | |
| cgt | tcc | acc | atg | tgt | ctg | acc | atg | gaa | gag | atg | ggc | ctg | gtg | gtt | gaa | 624 |
| Arg | Ser | Thr | Met | Cys | Leu | Thr | Met | Glu | Glu | Met | Gly | Leu | Val | Val | Glu | |
| | 195 | | | | | 200 | | | | | 205 | | | | | |
| gcg | cac | cac | cac | gaa | gtg | gcg | acc | gcc | ggt | cag | aac | gaa | gtg | gca | acc | 672 |
| Ala | His | His | His | Glu | Val | Ala | Thr | Ala | Gly | Gln | Asn | Glu | Val | Ala | Thr | |
| 210 | | | | | 215 | | | | | 220 | | | | | | |
| cgc | ttc | aac | acc | atg | acc | aag | aaa | gcc | gac | gaa | att | cag | atc | tat | aag | 720 |
| Arg | Phe | Asn | Thr | Met | Thr | Lys | Lys | Ala | Asp | Glu | Ile | Gln | Ile | Tyr | Lys | |
| 225 | | | | | 230 | | | | | 235 | | | | | 240 | |
| tac | gtg | gtg | cac | aac | gtg | gcg | cac | gcc | ttc | ggt | aaa | acc | gcg | acc | ttc | 768 |
| Tyr | Val | Val | His | Asn | Val | Ala | His | Ala | Phe | Gly | Lys | Thr | Ala | Thr | Phe | |
| | | | | 245 | | | | | 250 | | | | | 255 | | |
| atg | ccg | aag | ccc | atg | ttc | ggc | gac | aac | ggt | tcc | ggc | atg | cac | tgc | cac | 816 |

-continued

```
      Met Pro Lys Pro Met Phe Gly Asp Asn Gly Ser Gly Met His Cys His
                  260                 265                 270 atg tcg ctg tcc aag aac ggc acc aac ctg ttc gcc ggc gac aaa tac        864
Met Ser Leu Ser Lys Asn Gly Thr Asn Leu Phe Ala Gly Asp Lys Tyr
        275                 280                 285 ggc ggc ctg tct gaa acc gca ctg ttc tac atc ggc ggt atc atc aag        912
Gly Gly Leu Ser Glu Thr Ala Leu Phe Tyr Ile Gly Gly Ile Ile Lys
290                 295                 300 cac gcc aag gcg atc aac gcg ctg gcc aac ccg acc acc aac tcg tac        960
His Ala Lys Ala Ile Asn Ala Leu Ala Asn Pro Thr Thr Asn Ser Tyr
305                 310                 315                 320 aaa cgt ctg gtg cca ggc tac gaa gcg ccg gtg atg ctg gct tac tcc       1008
Lys Arg Leu Val Pro Gly Tyr Glu Ala Pro Val Met Leu Ala Tyr Ser
                325                 330                 335 gcc cgt aac cgc tcc gcg tcc atc cgt atc ccg gtg gtc gcc agc ccg       1056
Ala Arg Asn Arg Ser Ala Ser Ile Arg Ile Pro Val Val Ala Ser Pro
                340                 345                 350 aaa gcg cgc cgc atc gaa gcc cgc ttc ccg gat ccg gcg gct aac cca       1104
Lys Ala Arg Arg Ile Glu Ala Arg Phe Pro Asp Pro Ala Ala Asn Pro
                355                 360                 365 tac ctg tgc ttc gcc gca ctg ctg atg gcc ggc ctg gac ggc atc atc       1152
Tyr Leu Cys Phe Ala Ala Leu Leu Met Ala Gly Leu Asp Gly Ile Ile
        370                 375                 380 aac aag atc cac cct ggc gac gcc atg gac aaa aac ctg tac gac ctg       1200
Asn Lys Ile His Pro Gly Asp Ala Met Asp Lys Asn Leu Tyr Asp Leu
385                 390                 395                 400 ccg ccg gaa gaa gaa gcc gag atc cca aaa gtg gcc ggc tcg ctg gac       1248
Pro Pro Glu Glu Glu Ala Glu Ile Pro Lys Val Ala Gly Ser Leu Asp
                405                 410                 415 gag gcg atg gcc gcg ctg aac gaa gac cgc gag ttc ctg acc cgc ggc       1296
Glu Ala Met Ala Ala Leu Asn Glu Asp Arg Glu Phe Leu Thr Arg Gly
                420                 425                 430 ggc gtg ttc acc gac gat gcg atc gat gcc tac atc gaa ctg cgc aaa       1344
Gly Val Phe Thr Asp Asp Ala Ile Asp Ala Tyr Ile Glu Leu Arg Lys
        435                 440                 445 gaa gag atg gac cgc gtt cgc atg acg cca cac ccg gtc gag ttc gaa       1392
Glu Glu Met Asp Arg Val Arg Met Thr Pro His Pro Val Glu Phe Glu
450                 455                 460 ctg tac tac agc gtc taa                                                1410
Leu Tyr Tyr Ser Val  *
465

<210> SEQ ID NO 2
<211> LENGTH: 469
<212> TYPE: PRT
<213> ORGANISM: Serratia marcescens

<400> SEQUENCE: 2

Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
                20                  25                  30

Thr Ile Pro Ala His Gln Val Asn Ala Asp Phe Phe Glu Glu Gly Lys
        35                  40                  45

Met Phe Asp Gly Ser Ser Ile Gly Gly Trp Lys Gly Ile Asn Glu Ser
50                  55                  60

Asp Met Val Leu Met Pro Asp Ala Ser Thr Ala Val Leu Asp Pro Phe
65                  70                  75                  80

Phe Glu Glu Pro Thr Leu Ile Ile Arg Cys Asp Ile Leu Glu Pro Gly
                85                  90                  95
```

Thr Met Gln Gly Tyr Asp Arg Asp Pro Arg Ser Ile Ser Lys Arg Ala
            100                 105                 110

Glu Asp Phe Leu Arg Ser Ser Gly Ile Ala Asp Thr Val Leu Phe Gly
        115                 120                 125

Pro Glu Pro Glu Phe Phe Leu Phe Asp Asp Ile Arg Phe Gly Ser Ser
130                 135                 140

Ile Arg Gly Ser His Val Ala Ile Asp Asp Ile Glu Gly Ala Trp Asn
145                 150                 155                 160

Ser Gly Thr Lys Tyr Asp Gly Gly Asn Lys Gly His Arg Pro Ala Val
                165                 170                 175

Lys Gly Gly Tyr Phe Pro Val Pro Pro Val Asp Ser Ser Gln Asp Leu
                180                 185                 190

Arg Ser Thr Met Cys Leu Thr Met Glu Glu Met Gly Leu Val Val Glu
            195                 200                 205

Ala His His His Glu Val Ala Thr Ala Gly Gln Asn Glu Val Ala Thr
        210                 215                 220

Arg Phe Asn Thr Met Thr Lys Lys Ala Asp Glu Ile Gln Ile Tyr Lys
225                 230                 235                 240

Tyr Val Val His Asn Val Ala His Ala Phe Gly Lys Thr Ala Thr Phe
                245                 250                 255

Met Pro Lys Pro Met Phe Gly Asp Asn Gly Ser Gly Met His Cys His
            260                 265                 270

Met Ser Leu Ser Lys Asn Gly Thr Asn Leu Phe Ala Gly Asp Lys Tyr
        275                 280                 285

Gly Gly Leu Ser Glu Thr Ala Leu Phe Tyr Ile Gly Gly Ile Ile Lys
        290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Ala Ser Pro
            340                 345                 350

Lys Ala Arg Arg Ile Glu Ala Arg Phe Pro Asp Pro Ala Ala Asn Pro
        355                 360                 365

Tyr Leu Cys Phe Ala Ala Leu Leu Met Ala Gly Leu Asp Gly Ile Ile
        370                 375                 380

Asn Lys Ile His Pro Gly Asp Ala Met Asp Lys Asn Leu Tyr Asp Leu
385                 390                 395                 400

Pro Pro Glu Glu Glu Ala Glu Ile Pro Lys Val Ala Gly Ser Leu Asp
                405                 410                 415

Glu Ala Met Ala Ala Leu Asn Glu Asp Arg Glu Phe Leu Thr Arg Gly
            420                 425                 430

Gly Val Phe Thr Asp Asp Ala Ile Asp Ala Tyr Ile Glu Leu Arg Lys
        435                 440                 445

Glu Glu Met Asp Arg Val Arg Met Thr Pro His Pro Val Glu Phe Glu
        450                 455                 460

Leu Tyr Tyr Ser Val
465

<210> SEQ ID NO 3
<211> LENGTH: 1410
<212> TYPE: DNA
<213> ORGANISM: Artificial Sequence
<220> FEATURE:
<223> OTHER INFORMATION: ags1 variant nucleotide sequence (ags1m1)

<221> NAME/KEY: CDS
<222> LOCATION: (1)...(1410)

<400> SEQUENCE: 3

```
atg tcc gct gaa cac gtt ttg acg atg ctg aat gag cat gaa gtg aaa        48
Met Ser Ala Glu His Val Leu Thr Met Leu Asn Glu His Glu Val Lys
 1               5                  10                  15 ttc gta gac ctg cgt ttc act gac acc aag ggt aag gaa cag cac gtg        96
Phe Val Asp Leu Arg Phe Thr Asp Thr Lys Gly Lys Glu Gln His Val
             20                  25                  30 act atc ccg gct cac cag ata aac gcc gac ttc ttc gaa gaa ggt aaa       144
Thr Ile Pro Ala His Gln Ile Asn Ala Asp Phe Phe Glu Glu Gly Lys
         35                  40                  45 atg ttt gac ggc tcc tct atc ggt ggt tgg aag ggc atc aac gaa tct       192
Met Phe Asp Gly Ser Ser Ile Gly Gly Trp Lys Gly Ile Asn Glu Ser
     50                  55                  60 gac atg gtg ctg atg ccg gac gcc agc acg gcg gtt ctg gat ccg ttc       240
Asp Met Val Leu Met Pro Asp Ala Ser Thr Ala Val Leu Asp Pro Phe
 65                  70                  75                  80 ttc gaa gaa cct acg ctg atc att cgc tgt gac att ctc gag ccg ggc       288
Phe Glu Glu Pro Thr Leu Ile Ile Arg Cys Asp Ile Leu Glu Pro Gly
                 85                  90                  95 acc atg caa ggc tac gat cgc gac ccg cgt tcc atc tcc aaa cgc gcc       336
Thr Met Gln Gly Tyr Asp Arg Asp Pro Arg Ser Ile Ser Lys Arg Ala
            100                 105                 110 gaa gac ttc ctg cgc tcc tcc ggc atc gcg gac acc gtg ctg ttc ggg       384
Glu Asp Phe Leu Arg Ser Ser Gly Ile Ala Asp Thr Val Leu Phe Gly
        115                 120                 125 cca gag cct gag ttc ttc ctg ttc gac gac atc cgc ttc ggc agc agc       432
Pro Glu Pro Glu Phe Phe Leu Phe Asp Asp Ile Arg Phe Gly Ser Ser
    130                 135                 140 atc cgc ggt tcc cac gtg gcg atc gac gat atc gaa ggc gcc tgg aac       480
Ile Arg Gly Ser His Val Ala Ile Asp Asp Ile Glu Gly Ala Trp Asn
145                 150                 155                 160 tcc ggc aca aaa tac gac ggc ggc aac aaa ggc cac cgt ccg gcg gtg       528
Ser Gly Thr Lys Tyr Asp Gly Gly Asn Lys Gly His Arg Pro Ala Val
                165                 170                 175 aaa ggc ggt tac ttc ccg gtt cca ccg gtc gac tct tcg cag gat ctg       576
Lys Gly Gly Tyr Phe Pro Val Pro Pro Val Asp Ser Ser Gln Asp Leu
            180                 185                 190 cgt tcc acc atg tgt ctg acc atg gaa gag atg ggc ctg gtg gtt gaa       624
Arg Ser Thr Met Cys Leu Thr Met Glu Glu Met Gly Leu Val Val Glu
        195                 200                 205 gcg cac cac cac gaa atg gcg acc gcc ggt cag aac gaa gtg gca acc       672
Ala His His His Glu Met Ala Thr Ala Gly Gln Asn Glu Val Ala Thr
    210                 215                 220 cgc ttc aac acc atg acc aag aaa gcc gac gaa att cag atc tat aag       720
Arg Phe Asn Thr Met Thr Lys Lys Ala Asp Glu Ile Gln Ile Tyr Lys
225                 230                 235                 240 tac gtg gtg cac aac gtg gcg cac gcc ttc ggt aaa acc gcg acc ttc       768
Tyr Val Val His Asn Val Ala His Ala Phe Gly Lys Thr Ala Thr Phe
                245                 250                 255 atg ccg aag ccc atg ttc ggc gac aac ggt tcc ggc atg cac tgc cac       816
Met Pro Lys Pro Met Phe Gly Asp Asn Gly Ser Gly Met His Cys His
            260                 265                 270 atg tcg ctg tcc aag aac ggc acc aac ctg ttc gcc ggc gac aaa tac       864
Met Ser Leu Ser Lys Asn Gly Thr Asn Leu Phe Ala Gly Asp Lys Tyr
        275                 280                 285 ggc ggc ctg tct gaa acc gca ctg ttc tac atc ggc ggt atc atc aag       912
Gly Gly Leu Ser Glu Thr Ala Leu Phe Tyr Ile Gly Gly Ile Ile Lys
    290                 295                 300
```

```
cac gcc aag gcg atc aac gcg ctg gcc aac ccg acc acc aac tcg tac       960
His Ala Lys Ala Ile Asn Ala Leu Ala Asn Pro Thr Thr Asn Ser Tyr
305                 310                 315                 320 aaa cgt ctg gtg cca ggc tac gaa gcg ccg gtg atg ctg gct tac tcc      1008
Lys Arg Leu Val Pro Gly Tyr Glu Ala Pro Val Met Leu Ala Tyr Ser
                325                 330                 335 gcc cgt aac cgc tcc gcg tcc atc cgt atc ccg gtg gtc gcc agc ccg      1056
Ala Arg Asn Arg Ser Ala Ser Ile Arg Ile Pro Val Val Ala Ser Pro
            340                 345                 350 aaa gcg cgc cgc atc gaa gcc cgc ttc ccg gat ccg gcg gct aac cca      1104
Lys Ala Arg Arg Ile Glu Ala Arg Phe Pro Asp Pro Ala Ala Asn Pro
        355                 360                 365 tac ctg tgc ttc gcc gca ctg ctg atg gcc ggc ctg gac ggc atc atc      1152
Tyr Leu Cys Phe Ala Ala Leu Leu Met Ala Gly Leu Asp Gly Ile Ile
    370                 375                 380 aac aag atc cac cct ggc gac gcc atg gac aaa aac ctg tac gac ctg      1200
Asn Lys Ile His Pro Gly Asp Ala Met Asp Lys Asn Leu Tyr Asp Leu
385                 390                 395                 400 ccg ccg gaa gaa gaa gcc gag atc cca aaa gtg gcc ggc tcg ctg gac      1248
Pro Pro Glu Glu Glu Ala Glu Ile Pro Lys Val Ala Gly Ser Leu Asp
                405                 410                 415 gag gcg atg gcc gcg ctg aac gaa gac cgc gag ttc ctg acc cgc ggc      1296
Glu Ala Met Ala Ala Leu Asn Glu Asp Arg Glu Phe Leu Thr Arg Gly
            420                 425                 430 ggc gtg ttc acc gac gat gcg atc gat gcc tac atc gaa ctg cgc aaa      1344
Gly Val Phe Thr Asp Asp Ala Ile Asp Ala Tyr Ile Glu Leu Arg Lys
        435                 440                 445 gaa gag atg gac cgc gtt cgc atg acg cca cac ccg gtc gag ttc gaa      1392
Glu Glu Met Asp Arg Val Arg Met Thr Pro His Pro Val Glu Phe Glu
    450                 455                 460 ctg tac tac agc gtc taa                                               1410
Leu Tyr Tyr Ser Val  *
465
```

<210> SEQ ID NO 4
<211> LENGTH: 469
<212> TYPE: PRT
<213> ORGANISM: Artificial Sequence
<220> FEATURE:
<223> OTHER INFORMATION: AGS1 variant amino acid sequence (AGS1M1)

<400> SEQUENCE: 4

```
Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
            20                  25                  30

Thr Ile Pro Ala His Gln Ile Asn Ala Asp Phe Phe Glu Gly Lys
        35                  40                  45

Met Phe Asp Gly Ser Ser Ile Gly Gly Trp Lys Gly Ile Asn Glu Ser
    50                  55                  60

Asp Met Val Leu Met Pro Asp Ala Ser Thr Ala Val Leu Asp Pro Phe
65                  70                  75                  80

Phe Glu Glu Pro Thr Leu Ile Ile Arg Cys Asp Ile Leu Glu Pro Gly
                85                  90                  95

Thr Met Gln Gly Tyr Asp Arg Asp Pro Arg Ser Ile Ser Lys Arg Ala
            100                 105                 110

Glu Asp Phe Leu Arg Ser Ser Gly Ile Ala Asp Thr Val Leu Phe Gly
        115                 120                 125

Pro Glu Pro Glu Phe Phe Leu Phe Asp Asp Ile Arg Phe Gly Ser Ser
```

-continued

```
                    130                 135                 140
Ile Arg Gly Ser His Val Ala Ile Asp Asp Ile Glu Gly Ala Trp Asn
145                 150                 155                 160

Ser Gly Thr Lys Tyr Asp Gly Asn Lys Gly His Arg Pro Ala Val
                165                 170                 175

Lys Gly Gly Tyr Phe Pro Val Pro Val Asp Ser Ser Gln Asp Leu
                    180                 185                 190

Arg Ser Thr Met Cys Leu Thr Met Glu Glu Met Gly Leu Val Val Glu
                    195                 200                 205

Ala His His Glu Met Ala Thr Ala Gly Gln Asn Glu Val Ala Thr
            210                 215                 220

Arg Phe Asn Thr Met Thr Lys Lys Ala Asp Glu Ile Gln Ile Tyr Lys
225                 230                 235                 240

Tyr Val Val His Asn Val Ala His Ala Phe Gly Lys Thr Ala Thr Phe
                    245                 250                 255

Met Pro Lys Pro Met Phe Gly Asp Asn Gly Ser Gly Met His Cys His
                260                 265                 270

Met Ser Leu Ser Lys Asn Gly Thr Asn Leu Phe Ala Gly Asp Lys Tyr
                    275                 280                 285

Gly Gly Leu Ser Glu Thr Ala Leu Phe Tyr Ile Gly Gly Ile Ile Lys
                290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                    325                 330                 335

Ala Arg Asn Arg Ser Ala Ser Ile Arg Ile Pro Val Val Ala Ser Pro
                340                 345                 350

Lys Ala Arg Arg Ile Glu Ala Arg Phe Pro Asp Pro Ala Ala Asn Pro
                355                 360                 365

Tyr Leu Cys Phe Ala Ala Leu Leu Met Ala Gly Leu Asp Gly Ile Ile
                370                 375                 380

Asn Lys Ile His Pro Gly Asp Ala Met Asp Lys Asn Leu Tyr Asp Leu
385                 390                 395                 400

Pro Pro Glu Glu Glu Ala Glu Ile Pro Lys Val Ala Gly Ser Leu Asp
                    405                 410                 415

Glu Ala Met Ala Ala Leu Asn Glu Asp Arg Glu Phe Leu Thr Arg Gly
                420                 425                 430

Gly Val Phe Thr Asp Asp Ala Ile Asp Ala Tyr Ile Glu Leu Arg Lys
                435                 440                 445

Glu Glu Met Asp Arg Val Arg Met Thr Pro His Pro Val Glu Phe Glu
450                 455                 460

Leu Tyr Tyr Ser Val
465
```

<210> SEQ ID NO 5
<211> LENGTH: 1410
<212> TYPE: DNA
<213> ORGANISM: Artificial Sequence
<220> FEATURE:
<223> OTHER INFORMATION: ags1 variant nucleotide sequence (ags1m2)
<221> NAME/KEY: CDS
<222> LOCATION: (1)...(1410)

<400> SEQUENCE: 5

```
atg tcc gct gaa cac gtt ttg acg atg ctg aat gag cat gaa gtg aaa    48
Met Ser Ala Glu His Val Leu Thr Met Leu Asn Glu His Glu Val Lys
 1               5                  10                  15
```

```
ttc gta gac ctg cgt ttc act gac acc aag ggt aag gaa cag cac gtg        96
Phe Val Asp Leu Arg Phe Thr Asp Thr Lys Gly Lys Glu Gln His Val
         20                  25                  30 act atc ccg gct cac cag gta aac gcc gac ttc ttc gaa gaa ggt aaa       144
Thr Ile Pro Ala His Gln Val Asn Ala Asp Phe Phe Glu Glu Gly Lys
             35                  40                  45 atg ttt gac ggc tcc tct atc ggt ggt tgg aag ggc atc aac gaa tct       192
Met Phe Asp Gly Ser Ser Ile Gly Gly Trp Lys Gly Ile Asn Glu Ser
 50                  55                  60 gac atg gtg ctg atg ccg gac gcc agc acg gcg gtt ctg gat ccg ttc       240
Asp Met Val Leu Met Pro Asp Ala Ser Thr Ala Val Leu Asp Pro Phe
 65                  70                  75                  80 tcc gaa gaa cct acg ctg atc att cgc tgt gac att ctc gag ccg ggc       288
Ser Glu Glu Pro Thr Leu Ile Ile Arg Cys Asp Ile Leu Glu Pro Gly
                 85                  90                  95 acc atg caa ggc tac gat cgc gac ccg cgt tcc atc tcc aaa cgc gcc       336
Thr Met Gln Gly Tyr Asp Arg Asp Pro Arg Ser Ile Ser Lys Arg Ala
            100                 105                 110 gaa gac ttc ctg cgc tcc tcc ggc atc gcg gac acc gtg ctg ttc ggg       384
Glu Asp Phe Leu Arg Ser Ser Gly Ile Ala Asp Thr Val Leu Phe Gly
                115                 120                 125 cca gag cct gag ttc ttc ctg ttc gac gac atc cgc ttc ggc agc agc       432
Pro Glu Pro Glu Phe Phe Leu Phe Asp Asp Ile Arg Phe Gly Ser Ser
130                 135                 140 atc cgc ggt tcc cac gtg gcg atc gac gat atc gaa ggc gcc tgg aac       480
Ile Arg Gly Ser His Val Ala Ile Asp Asp Ile Glu Gly Ala Trp Asn
145                 150                 155                 160 tcc ggc aca aaa tac gac ggc ggc aac aaa ggc cac cgt ccg gcg gtg       528
Ser Gly Thr Lys Tyr Asp Gly Gly Asn Lys Gly His Arg Pro Ala Val
                165                 170                 175 aaa ggc ggt tac ttc ccg gtt cca tcg gtc gac tct tcg cag gat ctg       576
Lys Gly Gly Tyr Phe Pro Val Pro Ser Val Asp Ser Ser Gln Asp Leu
            180                 185                 190 cgt tcc acc atg tgt ctg acc atg gaa gag atg ggc ctg gtg gtt gaa       624
Arg Ser Thr Met Cys Leu Thr Met Glu Glu Met Gly Leu Val Val Glu
        195                 200                 205 gcg cac cac cac gaa gtg gcg acc gcc agt cag aac gaa gtg gca acc       672
Ala His His His Glu Val Ala Thr Ala Ser Gln Asn Glu Val Ala Thr
210                 215                 220 cgc ttc aac acc atg acc aag aaa gcc gac gaa att cag atc tat aag       720
Arg Phe Asn Thr Met Thr Lys Lys Ala Asp Glu Ile Gln Ile Tyr Lys
225                 230                 235                 240 tac gtg gtg cac aac gtg gca cac gcc ttc ggt aaa acc gcg acc ttc       768
Tyr Val Val His Asn Val Ala His Ala Phe Gly Lys Thr Ala Thr Phe
                245                 250                 255 atg ccg aag ccc atg ttc ggc gac aac ggt tcc ggc atg cac tgc cac       816
Met Pro Lys Pro Met Phe Gly Asp Asn Gly Ser Gly Met His Cys His
            260                 265                 270 atg tcg ctg tcc aag aac ggc acc aac ctg ttc gcc ggc gac aaa tac       864
Met Ser Leu Ser Lys Asn Gly Thr Asn Leu Phe Ala Gly Asp Lys Tyr
        275                 280                 285 ggc ggc ctg tct gaa acc gca ctg ttc tac atc ggc ggt atc aac aag       912
Gly Gly Leu Ser Glu Thr Ala Leu Phe Tyr Ile Gly Gly Ile Asn Lys
    290                 295                 300 cac gcc aag gcg atc aac gcg ctg gcc aac ccg acc acc aac tcg tac       960
His Ala Lys Ala Ile Asn Ala Leu Ala Asn Pro Thr Thr Asn Ser Tyr
305                 310                 315                 320 aaa cgt ctg gtg cca ggc tac gaa gcg ccg gtg atg ctg gct tac tcc      1008
Lys Arg Leu Val Pro Gly Tyr Glu Ala Pro Val Met Leu Ala Tyr Ser
                325                 330                 335
```

```
gcc cgt aac cgc tcc gcg tcc atc cgt atc ccg gtg gtc gcc agc ccg    1056
Ala Arg Asn Arg Ser Ala Ser Ile Arg Ile Pro Val Val Ala Ser Pro
        340                 345                 350 aaa gcg cgc cgc atc gaa gcc cgc ttc ccg gat ccg gcg gct aac cca    1104
Lys Ala Arg Arg Ile Glu Ala Arg Phe Pro Asp Pro Ala Ala Asn Pro
            355                 360                 365 tac ctg tgc ttc gcc gca ctg ctg atg gcc ggc ctg gac ggc atc atc    1152
Tyr Leu Cys Phe Ala Ala Leu Leu Met Ala Gly Leu Asp Gly Ile Ile
370                 375                 380 aac aag atc cac cct ggc gac gcc atg gac aaa aac ctg tac gac ctg    1200
Asn Lys Ile His Pro Gly Asp Ala Met Asp Lys Asn Leu Tyr Asp Leu
385                 390                 395                 400 ccg ccg gaa gaa gaa gcc gag atc cca aaa gtg gcc ggc tcg ctg gac    1248
Pro Pro Glu Glu Glu Ala Glu Ile Pro Lys Val Ala Gly Ser Leu Asp
                405                 410                 415 gag gcg atg gcc gcg ctg aac gaa gac cgc gag ttc ctg acc cgc ggc    1296
Glu Ala Met Ala Ala Leu Asn Glu Asp Arg Glu Phe Leu Thr Arg Gly
            420                 425                 430 ggc gtg ttc act gac gat gcg atc gat gcc tac atc gaa ctg cgc aaa    1344
Gly Val Phe Thr Asp Asp Ala Ile Asp Ala Tyr Ile Glu Leu Arg Lys
        435                 440                 445 gaa gag atg gac cgc gtt cgc atg acg cca cac ccg gtc gag ttc gaa    1392
Glu Glu Met Asp Arg Val Arg Met Thr Pro His Pro Val Glu Phe Glu
450                 455                 460 ctg tac tac agc gtc taa                                            1410
Leu Tyr Tyr Ser Val *
465

<210> SEQ ID NO 6
<211> LENGTH: 469
<212> TYPE: PRT
<213> ORGANISM: Artificial Sequence
<220> FEATURE:
<223> OTHER INFORMATION: AGS1 variant amino acid sequence (AGS1M2)

<400> SEQUENCE: 6

Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
                20                  25                  30

Thr Ile Pro Ala His Gln Val Asn Ala Asp Phe Phe Glu Glu Gly Lys
            35                  40                  45

Met Phe Asp Gly Ser Ser Ile Gly Gly Trp Lys Gly Ile Asn Glu Ser
        50                  55                  60

Asp Met Val Leu Met Pro Asp Ala Ser Thr Ala Val Leu Asp Pro Phe
65                  70                  75                  80

Ser Glu Glu Pro Thr Leu Ile Ile Arg Cys Asp Ile Leu Glu Pro Gly
                85                  90                  95

Thr Met Gln Gly Tyr Asp Arg Asp Pro Arg Ser Ile Ser Lys Arg Ala
            100                 105                 110

Glu Asp Phe Leu Arg Ser Ser Gly Ile Ala Asp Thr Val Leu Phe Gly
        115                 120                 125

Pro Glu Pro Glu Phe Phe Leu Phe Asp Asp Ile Arg Phe Gly Ser Ser
    130                 135                 140

Ile Arg Gly Ser His Val Ala Ile Asp Asp Ile Glu Gly Ala Trp Asn
145                 150                 155                 160

Ser Gly Thr Lys Tyr Asp Gly Gly Asn Lys Gly His Arg Pro Ala Val
                165                 170                 175
```

```
Lys Gly Gly Tyr Phe Pro Val Pro Ser Val Asp Ser Ser Gln Asp Leu
            180                 185                 190
Arg Ser Thr Met Cys Leu Thr Met Glu Glu Met Gly Leu Val Val Glu
        195                 200                 205
Ala His His Glu Val Ala Thr Ala Ser Gln Asn Glu Val Ala Thr
210                 215                 220
Arg Phe Asn Thr Met Thr Lys Lys Ala Asp Glu Ile Gln Ile Tyr Lys
225                 230                 235                 240
Tyr Val Val His Asn Val Ala His Ala Phe Gly Lys Thr Ala Thr Phe
                245                 250                 255
Met Pro Lys Pro Met Phe Gly Asp Asn Gly Ser Gly Met His Cys His
            260                 265                 270
Met Ser Leu Ser Lys Asn Gly Thr Asn Leu Phe Ala Gly Asp Lys Tyr
        275                 280                 285
Gly Gly Leu Ser Glu Thr Ala Leu Phe Tyr Ile Gly Ile Asn Lys
290                 295                 300
His Ala Lys Ala Ile Asn Ala Leu Ala Asn Pro Thr Thr Asn Ser Tyr
305                 310                 315                 320
Lys Arg Leu Val Pro Gly Tyr Glu Ala Pro Val Met Leu Ala Tyr Ser
                325                 330                 335
Ala Arg Asn Arg Ser Ala Ser Ile Arg Ile Pro Val Val Ala Ser Pro
            340                 345                 350
Lys Ala Arg Arg Ile Glu Ala Arg Phe Pro Asp Pro Ala Ala Asn Pro
        355                 360                 365
Tyr Leu Cys Phe Ala Ala Leu Leu Met Ala Gly Leu Asp Gly Ile Ile
370                 375                 380
Asn Lys Ile His Pro Gly Asp Ala Met Asp Lys Asn Leu Tyr Asp Leu
385                 390                 395                 400
Pro Pro Glu Glu Glu Ala Glu Ile Pro Lys Val Ala Gly Ser Leu Asp
                405                 410                 415
Glu Ala Met Ala Ala Leu Asn Glu Asp Arg Glu Phe Leu Thr Arg Gly
            420                 425                 430
Gly Val Phe Thr Asp Asp Ala Ile Asp Ala Tyr Ile Glu Leu Arg Lys
        435                 440                 445
Glu Glu Met Asp Arg Val Arg Met Thr Pro His Pro Val Glu Phe Glu
450                 455                 460
Leu Tyr Tyr Ser Val
465

<210> SEQ ID NO 7
<211> LENGTH: 1410
<212> TYPE: DNA
<213> ORGANISM: Artificial Sequence
<220> FEATURE:
<223> OTHER INFORMATION: ags1 variant nucleotide sequence (ags1m3)
<221> NAME/KEY: CDS
<222> LOCATION: (1)...(1410)

<400> SEQUENCE: 7 atg tcc gct gaa cac gtt ttg acg atg ctg aat gag cat gag gtg aaa      48
Met Ser Ala Glu His Val Leu Thr Met Leu Asn Glu His Glu Val Lys
 1               5                  10                  15 ttc gta gac ctg cgt ttc act gac acc aag ggt aag gaa cag cac gtg      96
Phe Val Asp Leu Arg Phe Thr Asp Thr Lys Gly Lys Glu Gln His Val
             20                  25                  30 act atc ccg gct cac cag gta aac gcc gac ttc ttc gaa gaa ggt aaa     144
Thr Ile Pro Ala His Gln Val Asn Ala Asp Phe Phe Glu Glu Gly Lys
         35                  40                  45
```

```
atg ttt gac ggc tcc tct atc ggt ggt tgg aag ggc atc aac gaa tct    192
Met Phe Asp Gly Ser Ser Ile Gly Gly Trp Lys Gly Ile Asn Glu Ser
 50              55                  60 gac atg gtg ctg atg ccg gac gcc agc acg gcg gtt ctg gat ccg ttc    240
Asp Met Val Leu Met Pro Asp Ala Ser Thr Ala Val Leu Asp Pro Phe
 65              70                  75                  80 ttc gac gaa cct acg ctg atc att cgc tgt gac att ctc gag ccg ggc    288
Phe Asp Glu Pro Thr Leu Ile Ile Arg Cys Asp Ile Leu Glu Pro Gly
                 85                  90                  95 acc atg caa ggc tac gat cgc gac ccg cgt tcc atc tcc aaa cgc gcc    336
Thr Met Gln Gly Tyr Asp Arg Asp Pro Arg Ser Ile Ser Lys Arg Ala
            100                 105                 110 gaa gac ttc ctg cgc tcc tcc ggc atc gcg gac acc gtg ctg ttc ggg    384
Glu Asp Phe Leu Arg Ser Ser Gly Ile Ala Asp Thr Val Leu Phe Gly
        115                 120                 125 cca gag cct gag ttc ttc ctg ttc gac gac atc cgc ttc ggc agc agc    432
Pro Glu Pro Glu Phe Phe Leu Phe Asp Asp Ile Arg Phe Gly Ser Ser
130                 135                 140 atc cgc ggt tcc cac gtg gcg atc gac gat atc gaa ggc gcc tgg aac    480
Ile Arg Gly Ser His Val Ala Ile Asp Asp Ile Glu Gly Ala Trp Asn
145                 150                 155                 160 tcc ggc aca aaa tac gac ggc ggc aac aaa ggc cac cgt ccg gcg gtg    528
Ser Gly Thr Lys Tyr Asp Gly Gly Asn Lys Gly His Arg Pro Ala Val
                165                 170                 175 aaa ggc ggt tac ttc ccg gtt cca ccg gtc gac tct tcg cag gat ctg    576
Lys Gly Gly Tyr Phe Pro Val Pro Pro Val Asp Ser Ser Gln Asp Leu
            180                 185                 190 cgt tcc acc atg tgt ctg acc atg gaa gag atg ggc ctg gtg gtt gaa    624
Arg Ser Thr Met Cys Leu Thr Met Glu Glu Met Gly Leu Val Val Glu
        195                 200                 205 gcg cac cac cac gaa gcg gcg acc gcc ggt cag aac gaa gtg gca acc    672
Ala His His His Glu Ala Ala Thr Ala Gly Gln Asn Glu Val Ala Thr
210                 215                 220 cgc ttc aac acc atg acc aag aaa gcc gac gaa att cag atc tat aag    720
Arg Phe Asn Thr Met Thr Lys Lys Ala Asp Glu Ile Gln Ile Tyr Lys
225                 230                 235                 240 tac gtg gtg cac aac gtg gcg cac gcc ttc ggt aaa acc gcg acc ttc    768
Tyr Val Val His Asn Val Ala His Ala Phe Gly Lys Thr Ala Thr Phe
                245                 250                 255 atg ccg aag ccc atg ttc ggc gac aac ggt tcc ggc atg cac tgc cac    816
Met Pro Lys Pro Met Phe Gly Asp Asn Gly Ser Gly Met His Cys His
            260                 265                 270 atg tcg ctg tcc aag aac ggc acc aac ctg ttc gcc ggc gac aaa tac    864
Met Ser Leu Ser Lys Asn Gly Thr Asn Leu Phe Ala Gly Asp Lys Tyr
        275                 280                 285 ggc ggc ctg tct gaa acc gca ctg ttc tac atc ggc ggt atc atc aag    912
Gly Gly Leu Ser Glu Thr Ala Leu Phe Tyr Ile Gly Gly Ile Ile Lys
290                 295                 300 cac gcc aag gcg atc aac gcg ctg gcc aac ccg acc acc aac tcg tac    960
His Ala Lys Ala Ile Asn Ala Leu Ala Asn Pro Thr Thr Asn Ser Tyr
305                 310                 315                 320 aaa cgt ctg gtg cca ggc tac gaa gcg ccg gtg atg ctg gct tac tcc   1008
Lys Arg Leu Val Pro Gly Tyr Glu Ala Pro Val Met Leu Ala Tyr Ser
                325                 330                 335 gcc cgt aac cgc tcc gcg tcc atc cgt atc ccg gtg gtc gcc agc ccg   1056
Ala Arg Asn Arg Ser Ala Ser Ile Arg Ile Pro Val Val Ala Ser Pro
            340                 345                 350 aaa gcg cgc cgc atc gaa gcc cgc ttc ccg gat ccg gcg gct aac cca   1104
Lys Ala Arg Arg Ile Glu Ala Arg Phe Pro Asp Pro Ala Ala Asn Pro
        355                 360                 365
```

```
tac ctg tgc ttc gcc gca ctg ctg atg gcc ggc ctg gac ggc atc atc      1152
Tyr Leu Cys Phe Ala Ala Leu Leu Met Ala Gly Leu Asp Gly Ile Ile
    370                 375                 380 aac aag atc cac cct ggc gac gcc atg gac aaa aac ctg tac gac ctg      1200
Asn Lys Ile His Pro Gly Asp Ala Met Asp Lys Asn Leu Tyr Asp Leu
385                 390                 395                 400 ccg ccg gaa gaa gaa gcc gag atc cca aaa gtg gcc ggc tcg ctg gac      1248
Pro Pro Glu Glu Glu Ala Glu Ile Pro Lys Val Ala Gly Ser Leu Asp
                405                 410                 415 gag gcg atg gcc gcg ctg aac gaa gac cgc gag ttc ctg acc cgc ggc      1296
Glu Ala Met Ala Ala Leu Asn Glu Asp Arg Glu Phe Leu Thr Arg Gly
            420                 425                 430 ggc gtg ttc acc gac gat gcg atc gat gcc tac atc gaa ctg cgc aaa      1344
Gly Val Phe Thr Asp Asp Ala Ile Asp Ala Tyr Ile Glu Leu Arg Lys
        435                 440                 445 gaa gag atg gac cgc gtt cgc atg acg cca cac ccg gtc gag ttc gaa      1392
Glu Glu Met Asp Arg Val Arg Met Thr Pro His Pro Val Glu Phe Glu
    450                 455                 460 ctg tac tac agc gtc taa                                              1410
Leu Tyr Tyr Ser Val *
465
```

<210> SEQ ID NO 8
<211> LENGTH: 469
<212> TYPE: PRT
<213> ORGANISM: Artificial Sequence
<220> FEATURE:
<223> OTHER INFORMATION: AGS1 variant amino acid sequence (AGS1M3)

<400> SEQUENCE: 8

```
Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
                20                  25                  30

Thr Ile Pro Ala His Gln Val Asn Ala Asp Phe Phe Glu Glu Gly Lys
            35                  40                  45

Met Phe Asp Gly Ser Ser Ile Gly Gly Trp Lys Gly Ile Asn Glu Ser
    50                  55                  60

Asp Met Val Leu Met Pro Asp Ala Ser Thr Ala Val Leu Asp Pro Phe
65                  70                  75                  80

Phe Asp Glu Pro Thr Leu Ile Ile Arg Cys Asp Ile Leu Glu Pro Gly
                85                  90                  95

Thr Met Gln Gly Tyr Asp Arg Asp Pro Arg Ser Ile Ser Lys Arg Ala
            100                 105                 110

Glu Asp Phe Leu Arg Ser Ser Gly Ile Ala Asp Thr Val Leu Phe Gly
    115                 120                 125

Pro Glu Pro Glu Phe Phe Leu Phe Asp Asp Ile Arg Phe Gly Ser Ser
130                 135                 140

Ile Arg Gly Ser His Val Ala Ile Asp Asp Ile Glu Gly Ala Trp Asn
145                 150                 155                 160

Ser Gly Thr Lys Tyr Asp Gly Gly Asn Lys Gly His Arg Pro Ala Val
                165                 170                 175

Lys Gly Gly Tyr Phe Pro Val Pro Val Asp Ser Ser Gln Asp Leu
            180                 185                 190

Arg Ser Thr Met Cys Leu Thr Met Glu Glu Met Gly Leu Val Val Glu
    195                 200                 205

Ala His His His Glu Ala Ala Thr Ala Gly Gln Asn Glu Val Ala Thr
210                 215                 220
```

```
Arg Phe Asn Thr Met Thr Lys Lys Ala Asp Glu Ile Gln Ile Tyr Lys
225                 230                 235                 240

Tyr Val Val His Asn Val Ala His Ala Phe Gly Lys Thr Ala Thr Phe
            245                 250                 255

Met Pro Lys Pro Met Phe Gly Asp Asn Gly Ser Gly Met His Cys His
        260                 265                 270

Met Ser Leu Ser Lys Asn Gly Thr Asn Leu Phe Ala Gly Asp Lys Tyr
    275                 280                 285

Gly Gly Leu Ser Glu Thr Ala Leu Phe Tyr Ile Gly Ile Ile Lys
290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
            325                 330                 335

Ala Arg Asn Arg Ser Ala Ser Ile Arg Ile Pro Val Val Ala Ser Pro
        340                 345                 350

Lys Ala Arg Arg Ile Glu Ala Arg Phe Pro Asp Pro Ala Ala Asn Pro
    355                 360                 365

Tyr Leu Cys Phe Ala Ala Leu Leu Met Ala Gly Leu Asp Gly Ile Ile
370                 375                 380

Asn Lys Ile His Pro Gly Asp Ala Met Asp Lys Asn Leu Tyr Asp Leu
385                 390                 395                 400

Pro Pro Glu Glu Glu Ala Glu Ile Pro Lys Val Ala Gly Ser Leu Asp
            405                 410                 415

Glu Ala Met Ala Ala Leu Asn Glu Asp Arg Glu Phe Leu Thr Arg Gly
        420                 425                 430

Gly Val Phe Thr Asp Asp Ala Ile Asp Ala Tyr Ile Glu Leu Arg Lys
    435                 440                 445

Glu Glu Met Asp Arg Val Arg Met Thr Pro His Pro Val Glu Phe Glu
450                 455                 460

Leu Tyr Tyr Ser Val
465

<210> SEQ ID NO 9
<211> LENGTH: 1410
<212> TYPE: DNA
<213> ORGANISM: Artificial Sequence
<220> FEATURE:
<223> OTHER INFORMATION: ags1 variant nucleotide sequence (ags1m4)
<221> NAME/KEY: CDS
<222> LOCATION: (1)...(1410)

<400> SEQUENCE: 9 atg tcc gct gaa cac gtt ttg acg atg ctg aat gag cat gaa gtg aaa        48
Met Ser Ala Glu His Val Leu Thr Met Leu Asn Glu His Glu Val Lys
1               5                   10                  15 ttc gta gac ctg cgt ttc act gac acc aag ggt aag gaa cag cac gtg        96
Phe Val Asp Leu Arg Phe Thr Asp Thr Lys Gly Lys Glu Gln His Val
            20                  25                  30 act atc ccg gct cac cag gta aac gcc gac ttc ttc gaa gaa ggt aaa       144
Thr Ile Pro Ala His Gln Val Asn Ala Asp Phe Phe Glu Glu Gly Lys
        35                  40                  45 atg ttt gac ggc tcc tct atc ggt ggt tgg aag ggc atc aac gaa tct       192
Met Phe Asp Gly Ser Ser Ile Gly Gly Trp Lys Gly Ile Asn Glu Ser
    50                  55                  60 gac atg gtg ctg atg ccg gac gcc agc acg gcg gtt ctg gat ccg ttc       240
Asp Met Val Leu Met Pro Asp Ala Ser Thr Ala Val Leu Asp Pro Phe
65                  70                  75                  80
```

```
ttc gaa gaa cct acg ctg atc att cgc tgt gac att ctc gag ccg ggc       288
Phe Glu Glu Pro Thr Leu Ile Ile Arg Cys Asp Ile Leu Glu Pro Gly
                85                  90                  95 acc atg cag ggc tac gat cgc gac ccg cgt tcc atc tcc aaa cgc gcc       336
Thr Met Gln Gly Tyr Asp Arg Asp Pro Arg Ser Ile Ser Lys Arg Ala
            100                 105                 110 gaa gac ttc ctg cgc tcc tcc ggc atc gcg gac acc gtg ctg ttc ggg       384
Glu Asp Phe Leu Arg Ser Ser Gly Ile Ala Asp Thr Val Leu Phe Gly
        115                 120                 125 cca gag cct gag ttc ttc ctg ttc gac gac atc cgc ttc ggc agc agc       432
Pro Glu Pro Glu Phe Phe Leu Phe Asp Asp Ile Arg Phe Gly Ser Ser
    130                 135                 140 atc cgc ggt tcc cac gtg acg atc gac gat atc gaa ggc gcc tgg aac       480
Ile Arg Gly Ser His Val Thr Ile Asp Asp Ile Glu Gly Ala Trp Asn
145                 150                 155                 160 tcc ggc aca aaa tac gac ggc ggc aac aaa ggc cac cgt ccg gcg gtg       528
Ser Gly Thr Lys Tyr Asp Gly Gly Asn Lys Gly His Arg Pro Ala Val
                165                 170                 175 aaa ggc ggt tac ttc ccg gtt cca ccg gtc gac tct tcg cag gat ctg       576
Lys Gly Gly Tyr Phe Pro Val Pro Pro Val Asp Ser Ser Gln Asp Leu
            180                 185                 190 cgt tcc acc atg tgt ctg acc atg gaa gag atg ggc ctg gtg gtt gaa       624
Arg Ser Thr Met Cys Leu Thr Met Glu Glu Met Gly Leu Val Val Glu
        195                 200                 205 gcg cac cac cac gaa atg gcg acc gcc ggt cag aac gaa gtg gca acc       672
Ala His His His Glu Met Ala Thr Ala Gly Gln Asn Glu Val Ala Thr
    210                 215                 220 cgc ttc aac acc atg acc aag aaa gcc gac gaa att cag atc tat aag       720
Arg Phe Asn Thr Met Thr Lys Lys Ala Asp Glu Ile Gln Ile Tyr Lys
225                 230                 235                 240 tac gtg gtg cac aac gtg gcg cac gcc ttc ggt aaa acc gcg acc ttc       768
Tyr Val Val His Asn Val Ala His Ala Phe Gly Lys Thr Ala Thr Phe
                245                 250                 255 atg ccg aag ccc atg ttc ggc gac aac ggt tcc ggc atg cac tgc cac       816
Met Pro Lys Pro Met Phe Gly Asp Asn Gly Ser Gly Met His Cys His
            260                 265                 270 atg tcg ctg tac aag aac ggc acc aac ctg ttc gcc ggc gac aaa tac       864
Met Ser Leu Tyr Lys Asn Gly Thr Asn Leu Phe Ala Gly Asp Lys Tyr
        275                 280                 285 ggc ggc ctg tct gaa acc gca ctg ttc tac atc ggc ggt atc atc aag       912
Gly Gly Leu Ser Glu Thr Ala Leu Phe Tyr Ile Gly Gly Ile Ile Lys
    290                 295                 300 cac gcc aag gcg atc aac gcg ctg gcc aac ccg acc acc aac tcg tac       960
His Ala Lys Ala Ile Asn Ala Leu Ala Asn Pro Thr Thr Asn Ser Tyr
305                 310                 315                 320 aaa cgt ctg gtg cca ggc tac gaa gcg ccg gtg atg ctg gct tac tcc      1008
Lys Arg Leu Val Pro Gly Tyr Glu Ala Pro Val Met Leu Ala Tyr Ser
                325                 330                 335 gcc cgt aac cgc tcc gcg tcc atc cgt atc ccg gtg gtc gcc agc ccg      1056
Ala Arg Asn Arg Ser Ala Ser Ile Arg Ile Pro Val Val Ala Ser Pro
            340                 345                 350 aaa gcg cgc cgc atc gaa gcc cgc ttc ccg gat ccg gcg gct aac cca      1104
Lys Ala Arg Arg Ile Glu Ala Arg Phe Pro Asp Pro Ala Ala Asn Pro
        355                 360                 365 tac ctg tgc ttc gcc gca ctg ctg atg gcc ggc ctg gac ggc atc atc      1152
Tyr Leu Cys Phe Ala Ala Leu Leu Met Ala Gly Leu Asp Gly Ile Ile
    370                 375                 380 aac aag atc cac cct ggc gac gcc atg gac aaa aac ctg tac gac ctg      1200
Asn Lys Ile His Pro Gly Asp Ala Met Asp Lys Asn Leu Tyr Asp Leu
385                 390                 395                 400
```

```
ccg ccg gaa gaa gaa gcc gag atc cca aaa gtg gcc ggc tcg ctg gac    1248
Pro Pro Glu Glu Glu Ala Glu Ile Pro Lys Val Ala Gly Ser Leu Asp
            405                 410                 415 gag gcg atg gcc gcg ctg aac gaa gac cgc gag ttc ctg acc cgc ggc    1296
Glu Ala Met Ala Ala Leu Asn Glu Asp Arg Glu Phe Leu Thr Arg Gly
        420                 425                 430 ggc gtg ttc acc gac gat gcg atc gat gcc tac atc gaa ctg cgc aaa    1344
Gly Val Phe Thr Asp Asp Ala Ile Asp Ala Tyr Ile Glu Leu Arg Lys
    435                 440                 445 gaa gag atg gac cgc gtt cgc atg acg cca cac ccg gtc gag ttc gaa    1392
Glu Glu Met Asp Arg Val Arg Met Thr Pro His Pro Val Glu Phe Glu
450                 455                 460 ctg tac tac agc gtc taa                                            1410
Leu Tyr Tyr Ser Val *
465

<210> SEQ ID NO 10
<211> LENGTH: 469
<212> TYPE: PRT
<213> ORGANISM: Artificial Sequence
<220> FEATURE:
<223> OTHER INFORMATION: AGS1 variant amino acid sequence (AGS1M4)

<400> SEQUENCE: 10

Met Ser Ala Glu His Val Leu Thr Met Leu Asn Glu His Glu Val Lys
 1               5                  10                  15

Phe Val Asp Leu Arg Phe Thr Asp Thr Lys Gly Lys Glu Gln His Val
            20                  25                  30

Thr Ile Pro Ala His Gln Val Asn Ala Asp Phe Phe Glu Glu Gly Lys
        35                  40                  45

Met Phe Asp Gly Ser Ser Ile Gly Gly Trp Lys Gly Ile Asn Glu Ser
    50                  55                  60

Asp Met Val Leu Met Pro Asp Ala Ser Thr Ala Val Leu Asp Pro Phe
65                  70                  75                  80

Phe Glu Glu Pro Thr Leu Ile Ile Arg Cys Asp Ile Leu Glu Pro Gly
                85                  90                  95

Thr Met Gln Gly Tyr Asp Arg Asp Pro Arg Ser Ile Ser Lys Arg Ala
            100                 105                 110

Glu Asp Phe Leu Arg Ser Ser Gly Ile Ala Asp Thr Val Leu Phe Gly
        115                 120                 125

Pro Glu Pro Glu Phe Phe Leu Phe Asp Asp Ile Arg Phe Gly Ser Ser
    130                 135                 140

Ile Arg Gly Ser His Val Thr Ile Asp Asp Ile Glu Gly Ala Trp Asn
145                 150                 155                 160

Ser Gly Thr Lys Tyr Asp Gly Gly Asn Lys Gly His Arg Pro Ala Val
                165                 170                 175

Lys Gly Gly Tyr Phe Pro Val Pro Pro Val Asp Ser Ser Gln Asp Leu
            180                 185                 190

Arg Ser Thr Met Cys Leu Thr Met Glu Glu Met Gly Leu Val Val Glu
        195                 200                 205

Ala His His His Glu Met Ala Thr Ala Gly Gln Asn Glu Val Ala Thr
    210                 215                 220

Arg Phe Asn Thr Met Thr Lys Lys Ala Asp Glu Ile Gln Ile Tyr Lys
225                 230                 235                 240

Tyr Val Val His Asn Val Ala His Ala Phe Gly Lys Thr Ala Thr Phe
                245                 250                 255

Met Pro Lys Pro Met Phe Gly Asp Asn Gly Ser Gly Met His Cys His
```

```
                        260                 265                 270
Met Ser Leu Tyr Lys Asn Gly Thr Asn Leu Phe Ala Gly Asp Lys Tyr
        275                 280                 285

Gly Gly Leu Ser Glu Thr Ala Leu Phe Tyr Ile Gly Ile Ile Lys
        290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Ala Ser Pro
            340                 345                 350

Lys Ala Arg Arg Ile Glu Ala Arg Phe Pro Asp Pro Ala Ala Asn Pro
        355                 360                 365

Tyr Leu Cys Phe Ala Ala Leu Leu Met Ala Gly Leu Asp Gly Ile Ile
    370                 375                 380

Asn Lys Ile His Pro Gly Asp Ala Met Asp Lys Asn Leu Tyr Asp Leu
385                 390                 395                 400

Pro Pro Glu Glu Ala Glu Ile Pro Lys Val Ala Gly Ser Leu Asp
                405                 410                 415

Glu Ala Met Ala Ala Leu Asn Glu Asp Arg Glu Phe Leu Thr Arg Gly
            420                 425                 430

Gly Val Phe Thr Asp Asp Ala Ile Asp Ala Tyr Ile Glu Leu Arg Lys
        435                 440                 445

Glu Glu Met Asp Arg Val Arg Met Thr Pro His Pro Val Glu Phe Glu
    450                 455                 460

Leu Tyr Tyr Ser Val
465

<210> SEQ ID NO 11
<211> LENGTH: 1410
<212> TYPE: DNA
<213> ORGANISM: Artificial Sequence
<220> FEATURE:
<223> OTHER INFORMATION: ags1 variant nucleotide sequence (ags1m6)
<221> NAME/KEY: CDS
<222> LOCATION: (1)...(1410)

<400> SEQUENCE: 11 atg tcc gct gaa cac gtt ttg acg atg ctg aat gag cat gaa gtg aaa         48
Met Ser Ala Glu His Val Leu Thr Met Leu Asn Glu His Glu Val Lys
1               5                   10                  15 ttc gta gac ctg cgt ttc act gac acc aag ggt aag gaa cag cac gtg         96
Phe Val Asp Leu Arg Phe Thr Asp Thr Lys Gly Lys Glu Gln His Val
            20                  25                  30 act atc ccg gct cac cag gta aac gcc gac ttc ttc gaa gaa ggt aaa        144
Thr Ile Pro Ala His Gln Val Asn Ala Asp Phe Phe Glu Glu Gly Lys
        35                  40                  45 atg ttt gac ggc tcc tct atc ggt ggt tgg aag ggc atc aac gaa tct        192
Met Phe Asp Gly Ser Ser Ile Gly Gly Trp Lys Gly Ile Asn Glu Ser
    50                  55                  60 gac atg gtg ctg atg ccg gac gcc agc acg gcg gtt ctg gat ccg ttc        240
Asp Met Val Leu Met Pro Asp Ala Ser Thr Ala Val Leu Asp Pro Phe
65                  70                  75                  80 ttc gaa gaa cct acg ctg atc att cgc tgt gac att ctc gag ccg ggc        288
Phe Glu Glu Pro Thr Leu Ile Ile Arg Cys Asp Ile Leu Glu Pro Gly
                85                  90                  95 acc atg caa ggc tac gat cgc gac ccg cgt tcc atc tcc aaa cgc gcc        336
Thr Met Gln Gly Tyr Asp Arg Asp Pro Arg Ser Ile Ser Lys Arg Ala
            100                 105                 110
```

```
gaa gac ttc ctg cgc tcc tcc ggc atc gcg gac acc gtg ctg ttc ggg        384
Glu Asp Phe Leu Arg Ser Ser Gly Ile Ala Asp Thr Val Leu Phe Gly
        115                 120                 125 cca gag cct gag ttc ttc ctg ttc gac gac atc cgc ttc ggc agc agc        432
Pro Glu Pro Glu Phe Phe Leu Phe Asp Asp Ile Arg Phe Gly Ser Ser
130                 135                 140 atc cgc ggt tcc cac gtg gcg atc gac gat atc gaa ggc gcc tgg aac        480
Ile Arg Gly Ser His Val Ala Ile Asp Asp Ile Glu Gly Ala Trp Asn
145                 150                 155                 160 tcc ggc aca aaa tac gac ggc ggc aac aaa ggc cac cgt ccg gcg gtg        528
Ser Gly Thr Lys Tyr Asp Gly Gly Asn Lys Gly His Arg Pro Ala Val
        165                 170                 175 aaa ggc ggt tac ttc ccg gtt cca ccg gtc gac tct tcg cag gat ctg        576
Lys Gly Gly Tyr Phe Pro Val Pro Pro Val Asp Ser Ser Gln Asp Leu
        180                 185                 190 cgt tcc acc atg tgt ctg acc atg gaa gag atg ggc ctg gtg gtt gaa        624
Arg Ser Thr Met Cys Leu Thr Met Glu Glu Met Gly Leu Val Val Glu
        195                 200                 205 gcg cac cac cac gaa gtg gcg acc gcc ggt cag aac gaa atg gca acc        672
Ala His His His Glu Val Ala Thr Ala Gly Gln Asn Glu Met Ala Thr
210                 215                 220 cgc ttc aac acc atg acc aag aaa gcc gac gaa att cag atc tat aag        720
Arg Phe Asn Thr Met Thr Lys Lys Ala Asp Glu Ile Gln Ile Tyr Lys
225                 230                 235                 240 tac gtg gtg cac aac gtg gcg cac gcc ttc ggt aaa acc gcg acc ttc        768
Tyr Val Val His Asn Val Ala His Ala Phe Gly Lys Thr Ala Thr Phe
                245                 250                 255 atg ccg aag ccc atg ttc ggc gtc aac ggt tcc ggc atg cac tgc cac        816
Met Pro Lys Pro Met Phe Gly Val Asn Gly Ser Gly Met His Cys His
        260                 265                 270 atg tcg ctg tcc aag aac ggc acc aac ctg ttc gcc ggc gac aaa tac        864
Met Ser Leu Ser Lys Asn Gly Thr Asn Leu Phe Ala Gly Asp Lys Tyr
        275                 280                 285 ggc ggc ctg tct gaa acc gca ctg ttc tac atc ggc ggt atc atc aag        912
Gly Gly Leu Ser Glu Thr Ala Leu Phe Tyr Ile Gly Gly Ile Ile Lys
290                 295                 300 cac gcc aag gcg atc aac gcg ctg gcc aac cca acc acc aac tcg tac        960
His Ala Lys Ala Ile Asn Ala Leu Ala Asn Pro Thr Thr Asn Ser Tyr
305                 310                 315                 320 aaa cgt ctg gtg cca ggc tac gaa gcg ccg gtg atg ctg gct tac tcc       1008
Lys Arg Leu Val Pro Gly Tyr Glu Ala Pro Val Met Leu Ala Tyr Ser
                325                 330                 335 gcc cgt aac cgc tcc gcg tcc atc agt atc ccg gtg gtc gcc agc ccg       1056
Ala Arg Asn Arg Ser Ala Ser Ile Ser Ile Pro Val Val Ala Ser Pro
                340                 345                 350 aaa gcg cgc cgc atc gaa gcc cgc ttc ccg gat ccg gcg gct aac cca       1104
Lys Ala Arg Arg Ile Glu Ala Arg Phe Pro Asp Pro Ala Ala Asn Pro
        355                 360                 365 tac ctg tgc ttc gcc gca ctg ctg atg gcc ggc ctg gac ggc atc atc       1152
Tyr Leu Cys Phe Ala Ala Leu Leu Met Ala Gly Leu Asp Gly Ile Ile
        370                 375                 380 aac aag atc cac cct ggc gac gcc atg gac aaa aac ctg tac gac ctg       1200
Asn Lys Ile His Pro Gly Asp Ala Met Asp Lys Asn Leu Tyr Asp Leu
385                 390                 395                 400 ccg ccg gaa gaa gaa gcc gag atc cca aaa gtg gcc ggc tcg ctg gac       1248
Pro Pro Glu Glu Glu Ala Glu Ile Pro Lys Val Ala Gly Ser Leu Asp
                405                 410                 415 gag gcg atg gcc gcg ctg aac gaa gac cgc gag ttc ctg acc cgc ggc       1296
Glu Ala Met Ala Ala Leu Asn Glu Asp Arg Glu Phe Leu Thr Arg Gly
                420                 425                 430
```

-continued

```
ggc gtg ttc acc gac gat gcg atc gat gcc tac atc gaa ctg cgc aaa    1344
Gly Val Phe Thr Asp Asp Ala Ile Asp Ala Tyr Ile Glu Leu Arg Lys
        435                 440                 445 gaa gag atg gac cgc gtt cgc atg acg cca cac ccg gtc gag ttc gaa    1392
Glu Glu Met Asp Arg Val Arg Met Thr Pro His Pro Val Glu Phe Glu
    450                 455                 460 ctg tac tac agc gtc taa                                            1410
Leu Tyr Tyr Ser Val *
465
```

<210> SEQ ID NO 12
<211> LENGTH: 469
<212> TYPE: PRT
<213> ORGANISM: Artificial Sequence
<220> FEATURE:
<223> OTHER INFORMATION: AGS1 variant amino acid sequence (AGS1M6)

<400> SEQUENCE: 12

```
Met Ser Ala Glu His Val Leu Thr Met Leu Asn Glu His Glu Val Lys
  1               5                  10                  15

Phe Val Asp Leu Arg Phe Thr Asp Thr Lys Gly Lys Glu Gln His Val
             20                  25                  30

Thr Ile Pro Ala His Gln Val Asn Ala Asp Phe Phe Glu Glu Gly Lys
         35                  40                  45

Met Phe Asp Gly Ser Ser Ile Gly Gly Trp Lys Gly Ile Asn Glu Ser
     50                  55                  60

Asp Met Val Leu Met Pro Asp Ala Ser Thr Ala Val Leu Asp Pro Phe
 65                  70                  75                  80

Phe Glu Glu Pro Thr Leu Ile Ile Arg Cys Asp Ile Leu Glu Pro Gly
                 85                  90                  95

Thr Met Gln Gly Tyr Asp Arg Asp Pro Arg Ser Ile Ser Lys Arg Ala
            100                 105                 110

Glu Asp Phe Leu Arg Ser Ser Gly Ile Ala Asp Thr Val Leu Phe Gly
        115                 120                 125

Pro Glu Pro Glu Phe Phe Leu Phe Asp Asp Ile Arg Phe Gly Ser Ser
    130                 135                 140

Ile Arg Gly Ser His Val Ala Ile Asp Asp Ile Glu Gly Ala Trp Asn
145                 150                 155                 160

Ser Gly Thr Lys Tyr Asp Gly Gly Asn Lys Gly His Arg Pro Ala Val
                165                 170                 175

Lys Gly Gly Tyr Phe Pro Val Pro Pro Val Asp Ser Ser Gln Asp Leu
            180                 185                 190

Arg Ser Thr Met Cys Leu Thr Met Glu Glu Met Gly Leu Val Val Glu
        195                 200                 205

Ala His His His Glu Val Ala Thr Ala Gly Gln Asn Glu Met Ala Thr
    210                 215                 220

Arg Phe Asn Thr Met Thr Lys Lys Ala Asp Glu Ile Gln Ile Tyr Lys
225                 230                 235                 240

Tyr Val Val His Asn Val Ala His Ala Phe Gly Lys Thr Ala Thr Phe
                245                 250                 255

Met Pro Lys Pro Met Phe Gly Val Asn Gly Ser Gly Met His Cys His
            260                 265                 270

Met Ser Leu Ser Lys Asn Gly Thr Asn Leu Phe Ala Gly Asp Lys Tyr
        275                 280                 285

Gly Gly Leu Ser Glu Thr Ala Leu Phe Tyr Ile Gly Gly Ile Ile Lys
    290                 295                 300
```

```
His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
            325                 330                 335

Ala Arg Asn Arg Ser Ala Ser Ile Ser Ile Pro Val Ala Ser Pro
        340                 345                 350

Lys Ala Arg Arg Ile Glu Ala Arg Phe Pro Asp Pro Ala Ala Asn Pro
    355                 360                 365

Tyr Leu Cys Phe Ala Ala Leu Leu Met Ala Gly Leu Asp Gly Ile Ile
370                 375                 380

Asn Lys Ile His Pro Gly Asp Ala Met Asp Lys Asn Leu Tyr Asp Leu
385                 390                 395                 400

Pro Pro Glu Glu Glu Ala Glu Ile Pro Lys Val Ala Gly Ser Leu Asp
                405                 410                 415

Glu Ala Met Ala Ala Leu Asn Glu Asp Arg Glu Phe Leu Thr Arg Gly
            420                 425                 430

Gly Val Phe Thr Asp Asp Ala Ile Asp Ala Tyr Ile Glu Leu Arg Lys
        435                 440                 445

Glu Glu Met Asp Arg Val Arg Met Thr Pro His Pro Val Glu Phe Glu
    450                 455                 460

Leu Tyr Tyr Ser Val
465

<210> SEQ ID NO 13
<211> LENGTH: 1410
<212> TYPE: DNA
<213> ORGANISM: Artificial Sequence
<220> FEATURE:
<223> OTHER INFORMATION: ags1 variant nucleotide sequence (ags1m7)
<221> NAME/KEY: CDS
<222> LOCATION: (1)...(1410)

<400> SEQUENCE: 13 atg tcc gct gaa cac gtt ttg acg atg ctg aat gag cat gaa gtg aaa      48
Met Ser Ala Glu His Val Leu Thr Met Leu Asn Glu His Glu Val Lys
1               5                   10                  15 ttc gta gac ctg cgt ttc act gac acc aag ggt aag gaa cag cac gtg      96
Phe Val Asp Leu Arg Phe Thr Asp Thr Lys Gly Lys Glu Gln His Val
            20                  25                  30 act atc ccg gct cac cag gta aac gcc gac ttc ttc gaa gaa ggt aaa     144
Thr Ile Pro Ala His Gln Val Asn Ala Asp Phe Phe Glu Glu Gly Lys
        35                  40                  45 atg ttt gac ggc tcc tct atc ggt ggt tgg aag ggc atc aac gaa tct     192
Met Phe Asp Gly Ser Ser Ile Gly Gly Trp Lys Gly Ile Asn Glu Ser
    50                  55                  60 gac atg gtg ctg atg ccg gac gcc agc acg gcg gtt ctg gat ccg ttc     240
Asp Met Val Leu Met Pro Asp Ala Ser Thr Ala Val Leu Asp Pro Phe
65                  70                  75                  80 ttc gaa gaa cct acg ctg atc att cgc tgt gac att ctc gag ccg ggc     288
Phe Glu Glu Pro Thr Leu Ile Ile Arg Cys Asp Ile Leu Glu Pro Gly
                85                  90                  95 acc atg caa ggc tac gat cgc gac ccg cgt tcc atc tcc aaa cgc gcc     336
Thr Met Gln Gly Tyr Asp Arg Asp Pro Arg Ser Ile Ser Lys Arg Ala
            100                 105                 110 gaa gac ttc ctg cgc tcc tcc ggc atc gcg gac acc gtg ctg ttc ggg     384
Glu Asp Phe Leu Arg Ser Ser Gly Ile Ala Asp Thr Val Leu Phe Gly
        115                 120                 125 cca gag cct gag ttc ttc ctg ttc gac gac atc cgc ttc ggt agc agc     432
Pro Glu Pro Glu Phe Phe Leu Phe Asp Asp Ile Arg Phe Gly Ser Ser
    130                 135                 140
```

| | |
|---|---|
| atc cgc ggt tcc cat gtg gcg atc gac gat atc gaa ggc gcc tgg aac<br>Ile Arg Gly Ser His Val Ala Ile Asp Asp Ile Glu Gly Ala Trp Asn<br>145                        150                  155               160 | 480 |
| tcc ggc aca aaa tac gac ggc tgc aac aaa ggc cac cgt ccg gcg gtg<br>Ser Gly Thr Lys Tyr Asp Gly Cys Asn Lys Gly His Arg Pro Ala Val<br>                 165                 170                 175 | 528 |
| aaa ggc ggt tac ttc ccg gtt cca ccg gtc gac tct tcg cag gat ctg<br>Lys Gly Gly Tyr Phe Pro Val Pro Pro Val Asp Ser Ser Gln Asp Leu<br>             180                 185                 190 | 576 |
| cgt tcc acc atg tgt ctg acc atg gaa gag atg ggc ctg gtg gtt gaa<br>Arg Ser Thr Met Cys Leu Thr Met Glu Glu Met Gly Leu Val Val Glu<br>       195            200                 205 | 624 |
| gcg cac cac cac gaa atg gcg acc gcc ggt cag aac gaa gtg gca acc<br>Ala His His His Glu Met Ala Thr Ala Gly Gln Asn Glu Val Ala Thr<br>210                       215                220 | 672 |
| cgc ttc aac acc atg acc aag aaa gcc gac gaa att cag atc tat aag<br>Arg Phe Asn Thr Met Thr Lys Lys Ala Asp Glu Ile Gln Ile Tyr Lys<br>225                       230                 235              240 | 720 |
| tac gtg gtg cac aac gtg gcg cac gcc ttc ggt aaa acc gcg acc ttc<br>Tyr Val Val His Asn Val Ala His Ala Phe Gly Lys Thr Ala Thr Phe<br>                 245                 250               255 | 768 |
| atg ccg aag ccc atg ttc ggc gac aac ggt tcc ggc atg cac tgc cac<br>Met Pro Lys Pro Met Phe Gly Asp Asn Gly Ser Gly Met His Cys His<br>             260                 265                 270 | 816 |
| atg tcg ctg tcc aag aac ggc acc aac ctg ttc gcc ggc gac aaa tac<br>Met Ser Leu Ser Lys Asn Gly Thr Asn Leu Phe Ala Gly Asp Lys Tyr<br>       275            280                 285 | 864 |
| ggc ggc ctg tct gaa acc gca ctg ttc tac atc ggc ggt atc atc aag<br>Gly Gly Leu Ser Glu Thr Ala Leu Phe Tyr Ile Gly Gly Ile Ile Lys<br>290                       295                300 | 912 |
| cac gcc aag gcg atc aac gcg ctg gcc aac ccg acc acc aac tcg tac<br>His Ala Lys Ala Ile Asn Ala Leu Ala Asn Pro Thr Thr Asn Ser Tyr<br>305                       310                315              320 | 960 |
| aaa cgt ctg gtg cca ggc tac gaa gcg cct gtg atg ctg gct tac tcc<br>Lys Arg Leu Val Pro Gly Tyr Glu Ala Pro Val Met Leu Ala Tyr Ser<br>                 325                 330               335 | 1008 |
| gcc cgt aac cgc tcc gcg tcc atc cgt atc ccg gtg gtc gcc agc ccg<br>Ala Arg Asn Arg Ser Ala Ser Ile Arg Ile Pro Val Val Ala Ser Pro<br>             340                 345                 350 | 1056 |
| aaa gcg cgc cgc atc gaa gcc cgc ttc ccg gat ccg gcg gct aac cca<br>Lys Ala Arg Arg Ile Glu Ala Arg Phe Pro Asp Pro Ala Ala Asn Pro<br>       355            360                 365 | 1104 |
| tac ctg tgc ttc gcc gca ctg ctg atg gcc ggc ctg gac ggc atc atc<br>Tyr Leu Cys Phe Ala Ala Leu Leu Met Ala Gly Leu Asp Gly Ile Ile<br>370                       375                380 | 1152 |
| aac aag atc cac cct ggc gac gcc atg gac aga aac ctg tac gac ctg<br>Asn Lys Ile His Pro Gly Asp Ala Met Asp Arg Asn Leu Tyr Asp Leu<br>385                       390                395              400 | 1200 |
| ccg ccg gaa gaa gaa gcc gag atc cca aaa gtg gcc ggc tcg ctg gac<br>Pro Pro Glu Glu Glu Ala Glu Ile Pro Lys Val Ala Gly Ser Leu Asp<br>                 405                 410               415 | 1248 |
| gag gcg atg gcc gcg ctg aac gaa gac cgc gag ttc ctg acc cgc ggc<br>Glu Ala Met Ala Ala Leu Asn Glu Asp Arg Glu Phe Leu Thr Arg Gly<br>             420                 425                 430 | 1296 |
| ggc gtg ttc acc gac gat gcg atc gat gcc tac atc gaa ctg cgc aaa<br>Gly Val Phe Thr Asp Asp Ala Ile Asp Ala Tyr Ile Glu Leu Arg Lys<br>       435            440                 445 | 1344 |
| gaa gag atg gac cgc gtt cgc atg acg cca cac ccg gtc gag ttc gaa<br>Glu Glu Met Asp Arg Val Arg Met Thr Pro His Pro Val Glu Phe Glu<br>450                       455                460 | 1392 |

```
ctg tac tac agc gtc taa                                    1410
Leu Tyr Tyr Ser Val  *
465

<210> SEQ ID NO 14
<211> LENGTH: 469
<212> TYPE: PRT
<213> ORGANISM: Artificial Sequence
<220> FEATURE:
<223> OTHER INFORMATION: AGS1 variant amino acid sequence (AGS1M7)

<400> SEQUENCE: 14

Met Ser Ala Glu His Val Leu Thr Met Leu Asn Glu His Glu Val Lys
 1               5                  10                  15

Phe Val Asp Leu Arg Phe Thr Asp Thr Lys Gly Lys Glu Gln His Val
            20                  25                  30

Thr Ile Pro Ala His Gln Val Asn Ala Asp Phe Phe Glu Glu Gly Lys
        35                  40                  45

Met Phe Asp Gly Ser Ser Ile Gly Gly Trp Lys Gly Ile Asn Glu Ser
 50                  55                  60

Asp Met Val Leu Met Pro Asp Ala Ser Thr Ala Val Leu Asp Pro Phe
 65                  70                  75                  80

Phe Glu Glu Pro Thr Leu Ile Ile Arg Cys Asp Ile Leu Glu Pro Gly
                85                  90                  95

Thr Met Gln Gly Tyr Asp Arg Asp Pro Arg Ser Ile Ser Lys Arg Ala
            100                 105                 110

Glu Asp Phe Leu Arg Ser Ser Gly Ile Ala Asp Thr Val Leu Phe Gly
        115                 120                 125

Pro Glu Pro Glu Phe Phe Leu Phe Asp Asp Ile Arg Phe Gly Ser Ser
130                 135                 140

Ile Arg Gly Ser His Val Ala Ile Asp Asp Ile Glu Gly Ala Trp Asn
145                 150                 155                 160

Ser Gly Thr Lys Tyr Asp Gly Cys Asn Lys Gly His Arg Pro Ala Val
                165                 170                 175

Lys Gly Gly Tyr Phe Pro Val Pro Pro Val Asp Ser Ser Gln Asp Leu
            180                 185                 190

Arg Ser Thr Met Cys Leu Thr Met Glu Glu Met Gly Leu Val Val Glu
        195                 200                 205

Ala His His His Glu Met Ala Thr Ala Gly Gln Asn Glu Val Ala Thr
    210                 215                 220

Arg Phe Asn Thr Met Thr Lys Lys Ala Asp Glu Ile Gln Ile Tyr Lys
225                 230                 235                 240

Tyr Val Val His Asn Val Ala His Ala Phe Gly Lys Thr Ala Thr Phe
                245                 250                 255

Met Pro Lys Pro Met Phe Gly Asp Asn Gly Ser Gly Met His Cys His
            260                 265                 270

Met Ser Leu Ser Lys Asn Gly Thr Asn Leu Phe Ala Gly Asp Lys Tyr
        275                 280                 285

Gly Gly Leu Ser Glu Thr Ala Leu Phe Tyr Ile Gly Gly Ile Ile Lys
    290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Ala Ser Pro
            340                 345                 350
```

```
Lys Ala Arg Arg Ile Glu Ala Arg Phe Pro Asp Pro Ala Ala Asn Pro
            355                 360                 365

Tyr Leu Cys Phe Ala Ala Leu Leu Met Ala Gly Leu Asp Gly Ile Ile
370                 375                 380

Asn Lys Ile His Pro Gly Asp Ala Met Asp Arg Asn Leu Tyr Asp Leu
385                 390                 395                 400

Pro Pro Glu Glu Glu Ala Glu Ile Pro Lys Val Ala Gly Ser Leu Asp
            405                 410                 415

Glu Ala Met Ala Ala Leu Asn Glu Asp Arg Glu Phe Leu Thr Arg Gly
            420                 425                 430

Gly Val Phe Thr Asp Asp Ala Ile Asp Ala Tyr Ile Glu Leu Arg Lys
            435                 440                 445

Glu Glu Met Asp Arg Val Arg Met Thr Pro His Pro Val Glu Phe Glu
            450                 455                 460

Leu Tyr Tyr Ser Val
465

<210> SEQ ID NO 15
<211> LENGTH: 1410
<212> TYPE: DNA
<213> ORGANISM: Artificial Sequence
<220> FEATURE:
<223> OTHER INFORMATION: ags1 variant nucleotide sequence (ags1m8)
<221> NAME/KEY: CDS
<222> LOCATION: (1)...(1410)

<400> SEQUENCE: 15 atg tcc gct gaa cac gtt ttg acg atg ctg aat gag cat gaa gtg aaa     48
Met Ser Ala Glu His Val Leu Thr Met Leu Asn Glu His Glu Val Lys
1               5                   10                  15 ttc gta gac ctg cgt ttc act gac acc aag ggt aag gaa cag cac gtg     96
Phe Val Asp Leu Arg Phe Thr Asp Thr Lys Gly Lys Glu Gln His Val
                20                  25                  30 act atc ccg gct cac cag gta aac gcc gac ttc ttc gaa gaa ggt aaa    144
Thr Ile Pro Ala His Gln Val Asn Ala Asp Phe Phe Glu Glu Gly Lys
            35                  40                  45 atg ttt gac ggc tcc tct atc ggt ggt tgg aag ggc atc aac gaa tct    192
Met Phe Asp Gly Ser Ser Ile Gly Gly Trp Lys Gly Ile Asn Glu Ser
    50                  55                  60 gac atg gtg ctg atg ccg gac gcc agc acg gcg gtt ctg gat ccg ttc    240
Asp Met Val Leu Met Pro Asp Ala Ser Thr Ala Val Leu Asp Pro Phe
65                  70                  75                  80 ttc gaa gaa cct acg ctg atc att cgc tgt gac att ctc gag ccg ggc    288
Phe Glu Glu Pro Thr Leu Ile Ile Arg Cys Asp Ile Leu Glu Pro Gly
                85                  90                  95 acc atg caa ggc tac gat cgc gac ccg cgt tcc atc tcc aaa cgc gcc    336
Thr Met Gln Gly Tyr Asp Arg Asp Pro Arg Ser Ile Ser Lys Arg Ala
            100                 105                 110 gaa gac ttc ctg cgc tcc tcc ggc atc gcg gac acc gtg ctg ttc ggg    384
Glu Asp Phe Leu Arg Ser Ser Gly Ile Ala Asp Thr Val Leu Phe Gly
        115                 120                 125 cca gag cct gag ttc ttc ctg ttc gac gac atc cgc ttc ggc agc agc    432
Pro Glu Pro Glu Phe Phe Leu Phe Asp Asp Ile Arg Phe Gly Ser Ser
    130                 135                 140 atc cgc ggt tcc cac gtg gcg atc gac gat atc gaa ggc gcc tgg aac    480
Ile Arg Gly Ser His Val Ala Ile Asp Asp Ile Glu Gly Ala Trp Asn
145                 150                 155                 160 tcc ggc aca aaa tac gac ggc ggc aac aaa ggc cac cgt ccg gcg gtg    528
Ser Gly Thr Lys Tyr Asp Gly Gly Asn Lys Gly His Arg Pro Ala Val
                165                 170                 175
```

| | | |
|---|---|---|
| aaa ggc ggt tac ttc ccg gtt cca ccg gtc gac tct tcg cag gat ctg<br>Lys Gly Gly Tyr Phe Pro Val Pro Pro Val Asp Ser Ser Gln Asp Leu<br>180 185 190 | | 576 |
| cgt tcc acc atg tgt ctg acc atg gaa gag atg ggc ctg gtg gtt gaa<br>Arg Ser Thr Met Cys Leu Thr Met Glu Glu Met Gly Leu Val Val Glu<br>195 200 205 | | 624 |
| gcg cac cac cac gaa gtg gcg acc gcc ggt cag aac gaa gtg gca acc<br>Ala His His His Glu Val Ala Thr Ala Gly Gln Asn Glu Val Ala Thr<br>210 215 220 | | 672 |
| cgc ttc aac acc atg acc aag aaa gcc gac gaa att cag atc tat aag<br>Arg Phe Asn Thr Met Thr Lys Lys Ala Asp Glu Ile Gln Ile Tyr Lys<br>225 230 235 240 | | 720 |
| tac gtg gtg cac aac gtg gcg cac gcc ttc ggt aaa acc gcg acc ttc<br>Tyr Val Val His Asn Val Ala His Ala Phe Gly Lys Thr Ala Thr Phe<br>245 250 255 | | 768 |
| atg ccg aag ccc atg ttc ggc gac aac ggt tcc ggc atg cac tgc cac<br>Met Pro Lys Pro Met Phe Gly Asp Asn Gly Ser Gly Met His Cys His<br>260 265 270 | | 816 |
| atg tcg ctg tcc aag aac ggc acc aac ctg ttc gcc ggc gac aaa tac<br>Met Ser Leu Ser Lys Asn Gly Thr Asn Leu Phe Ala Gly Asp Lys Tyr<br>275 280 285 | | 864 |
| ggc ggc ctg tct gaa acc gca ctg ttc tac atc ggc ggt atc atc aag<br>Gly Gly Leu Ser Glu Thr Ala Leu Phe Tyr Ile Gly Gly Ile Ile Lys<br>290 295 300 | | 912 |
| cac gcc aag gcg atc aac gcg ctg gcc aac ccg acc acc aac tcg tac<br>His Ala Lys Ala Ile Asn Ala Leu Ala Asn Pro Thr Thr Asn Ser Tyr<br>305 310 315 320 | | 960 |
| aaa cgt ctg gtg cca ggc tac gaa gcg ccg gtg atg ctg gct tac tcc<br>Lys Arg Leu Val Pro Gly Tyr Glu Ala Pro Val Met Leu Ala Tyr Ser<br>325 330 335 | | 1008 |
| gcc cgt aac cgc tcc gcg tcc atc agt atc ccg gtg gtc gcc agc ccg<br>Ala Arg Asn Arg Ser Ala Ser Ile Ser Ile Pro Val Val Ala Ser Pro<br>340 345 350 | | 1056 |
| aaa gcg cgc cgc atc gaa gcc cgc ttc ccg gat ccg gcg gct aac cca<br>Lys Ala Arg Arg Ile Glu Ala Arg Phe Pro Asp Pro Ala Ala Asn Pro<br>355 360 365 | | 1104 |
| tac ctg tgc ttc gcc gca ctg ctg atg gcc ggc ctg gac ggc atc atc<br>Tyr Leu Cys Phe Ala Ala Leu Leu Met Ala Gly Leu Asp Gly Ile Ile<br>370 375 380 | | 1152 |
| aac aag atc cac cct ggc gac gcc atg gac aaa aac ctg tac gac ctg<br>Asn Lys Ile His Pro Gly Asp Ala Met Asp Lys Asn Leu Tyr Asp Leu<br>385 390 395 400 | | 1200 |
| ccg ccg gaa gaa gaa gcc gag atc cca aaa gtg gcc ggc tcg ctg gac<br>Pro Pro Glu Glu Glu Ala Glu Ile Pro Lys Val Ala Gly Ser Leu Asp<br>405 410 415 | | 1248 |
| gag gcg atg gcc gcg ctg aac gaa gac cgc gag ttc ctg acc cgc ggc<br>Glu Ala Met Ala Ala Leu Asn Glu Asp Arg Glu Phe Leu Thr Arg Gly<br>420 425 430 | | 1296 |
| ggc gtg ttc acc gac gat gcg atc gat gcc tac atc gaa ctg tgc aaa<br>Gly Val Phe Thr Asp Asp Ala Ile Asp Ala Tyr Ile Glu Leu Cys Lys<br>435 440 445 | | 1344 |
| gaa gag atg gac cgc gtt cgc atg acg cca cac ccg gtc gag ttc gaa<br>Glu Glu Met Asp Arg Val Arg Met Thr Pro His Pro Val Glu Phe Glu<br>450 455 460 | | 1392 |
| ctg tac tac agc gtc taa<br>Leu Tyr Tyr Ser Val *<br>465 | | 1410 |

<210> SEQ ID NO 16
<211> LENGTH: 469

```
<212> TYPE: PRT
<213> ORGANISM: Artificial Sequence
<220> FEATURE:
<223> OTHER INFORMATION: AGS1 variant amino acid sequence (AGS1M8)

<400> SEQUENCE: 16

Met Ser Ala Glu His Val Leu Thr Met Leu Asn Glu His Glu Val Lys
 1               5                  10                  15

Phe Val Asp Leu Arg Phe Thr Asp Thr Lys Gly Lys Glu Gln His Val
                20                  25                  30

Thr Ile Pro Ala His Gln Val Asn Ala Asp Phe Phe Glu Glu Gly Lys
            35                  40                  45

Met Phe Asp Gly Ser Ser Ile Gly Gly Trp Lys Gly Ile Asn Glu Ser
 50                  55                  60

Asp Met Val Leu Met Pro Asp Ala Ser Thr Ala Val Leu Asp Pro Phe
 65                  70                  75                  80

Phe Glu Glu Pro Thr Leu Ile Ile Arg Cys Asp Ile Leu Glu Pro Gly
                85                  90                  95

Thr Met Gln Gly Tyr Asp Arg Asp Pro Arg Ser Ile Ser Lys Arg Ala
            100                 105                 110

Glu Asp Phe Leu Arg Ser Ser Gly Ile Ala Asp Thr Val Leu Phe Gly
            115                 120                 125

Pro Glu Pro Glu Phe Phe Leu Phe Asp Asp Ile Arg Phe Gly Ser Ser
130                 135                 140

Ile Arg Gly Ser His Val Ala Ile Asp Asp Ile Glu Gly Ala Trp Asn
145                 150                 155                 160

Ser Gly Thr Lys Tyr Asp Gly Gly Asn Lys Gly His Arg Pro Ala Val
                165                 170                 175

Lys Gly Gly Tyr Phe Pro Val Pro Pro Val Asp Ser Ser Gln Asp Leu
            180                 185                 190

Arg Ser Thr Met Cys Leu Thr Met Glu Glu Met Gly Leu Val Val Glu
            195                 200                 205

Ala His His His Glu Val Ala Thr Ala Gly Gln Asn Glu Val Ala Thr
210                 215                 220

Arg Phe Asn Thr Met Thr Lys Lys Ala Asp Glu Ile Gln Ile Tyr Lys
225                 230                 235                 240

Tyr Val Val His Asn Val Ala His Ala Phe Gly Lys Thr Ala Thr Phe
                245                 250                 255

Met Pro Lys Pro Met Phe Gly Asp Asn Gly Ser Gly Met His Cys His
            260                 265                 270

Met Ser Leu Ser Lys Asn Gly Thr Asn Leu Phe Ala Gly Asp Lys Tyr
            275                 280                 285

Gly Gly Leu Ser Glu Thr Ala Leu Phe Tyr Ile Gly Gly Ile Ile Lys
290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Ser Ile Pro Val Val Ala Ser Pro
            340                 345                 350

Lys Ala Arg Arg Ile Glu Ala Arg Phe Pro Asp Pro Ala Ala Asn Pro
            355                 360                 365

Tyr Leu Cys Phe Ala Ala Leu Leu Met Ala Gly Leu Asp Gly Ile Ile
370                 375                 380

Asn Lys Ile His Pro Gly Asp Ala Met Asp Lys Asn Leu Tyr Asp Leu
```

```
385                 390                 395                 400
Pro Pro Glu Glu Glu Ala Glu Ile Pro Lys Val Ala Gly Ser Leu Asp
            405                 410                 415

Glu Ala Met Ala Ala Leu Asn Glu Asp Arg Glu Phe Leu Thr Arg Gly
        420                 425                 430

Gly Val Phe Thr Asp Asp Ala Ile Asp Ala Tyr Ile Glu Leu Cys Lys
            435                 440                 445

Glu Glu Met Asp Arg Val Arg Met Thr Pro His Pro Val Glu Phe Glu
        450                 455                 460

Leu Tyr Tyr Ser Val
465

<210> SEQ ID NO 17
<211> LENGTH: 1410
<212> TYPE: DNA
<213> ORGANISM: Artificial Sequence
<220> FEATURE:
<223> OTHER INFORMATION: ags1 variant nucleotide sequence (ags1m9)
<221> NAME/KEY: CDS
<222> LOCATION: (1)...(1410)

<400> SEQUENCE: 17 atg acc gct gaa cac gtt ttg acg atg ctg aat gag cat gaa gtg aaa      48
Met Thr Ala Glu His Val Leu Thr Met Leu Asn Glu His Glu Val Lys
 1               5                  10                  15 ttc gta gac ctg cgt ttc act gac acc aag ggt aag gaa cag cac gtg      96
Phe Val Asp Leu Arg Phe Thr Asp Thr Lys Gly Lys Glu Gln His Val
                20                  25                  30 act atc ccg gct cac cag gta aac gcc gac ttc ttc gaa gaa ggt aaa     144
Thr Ile Pro Ala His Gln Val Asn Ala Asp Phe Phe Glu Glu Gly Lys
            35                  40                  45 atg ttt gac ggc tcc tct atc ggt ggt tgg aag ggc atc aac gaa tct     192
Met Phe Asp Gly Ser Ser Ile Gly Gly Trp Lys Gly Ile Asn Glu Ser
        50                  55                  60 gac atg gtg ctg atg ccg gac gtc agc acg gcg gtt ctg gat ccg ttc     240
Asp Met Val Leu Met Pro Asp Val Ser Thr Ala Val Leu Asp Pro Phe
    65                  70                  75                  80 ttc gaa gaa cct acg ctg atc att cgc tgt gac att ctc gag ccg ggc     288
Phe Glu Glu Pro Thr Leu Ile Ile Arg Cys Asp Ile Leu Glu Pro Gly
                85                  90                  95 acc atg caa ggc tac gat cgc gac ccg cgt tcc atc tcc aaa cgc gcc     336
Thr Met Gln Gly Tyr Asp Arg Asp Pro Arg Ser Ile Ser Lys Arg Ala
               100                 105                 110 gaa gac ttc ctg cgc tcc tcc ggc atc gcg gac acc gtg ctg ttc ggg     384
Glu Asp Phe Leu Arg Ser Ser Gly Ile Ala Asp Thr Val Leu Phe Gly
            115                 120                 125 cca gag cct gag ttc ttc ctg ttc gac gac atc cgc ttc ggc agc agc     432
Pro Glu Pro Glu Phe Phe Leu Phe Asp Asp Ile Arg Phe Gly Ser Ser
        130                 135                 140 atc cgc ggt tcc cac gtg gcg atc gac gat atc gaa ggc gcc tgg aac     480
Ile Arg Gly Ser His Val Ala Ile Asp Asp Ile Glu Gly Ala Trp Asn
145                 150                 155                 160 tcc ggc aca aaa tac gac ggc ggc aac aaa ggc cac cgt ccg gcg gtg     528
Ser Gly Thr Lys Tyr Asp Gly Gly Asn Lys Gly His Arg Pro Ala Val
                165                 170                 175 aaa ggc ggt tac ttc ccg gtt cca ccg gtc gac tct tcg cag gat ctg     576
Lys Gly Gly Tyr Phe Pro Val Pro Pro Val Asp Ser Ser Gln Asp Leu
            180                 185                 190 cgt tcc acc atg tgt ctg acc atg gaa gag atg ggc ctg gtg gtt gaa     624
Arg Ser Thr Met Cys Leu Thr Met Glu Glu Met Gly Leu Val Val Glu
        195                 200                 205
```

```
gcg cac cac cac gaa gtg gcg acc gcc ggt cag aac gaa gtg gca acc      672
Ala His His His Glu Val Ala Thr Ala Gly Gln Asn Glu Val Ala Thr
    210                 215                 220 cgc ttc aac acc atg acc aag aaa gcc gac gaa att cag atc tat aag      720
Arg Phe Asn Thr Met Thr Lys Lys Ala Asp Glu Ile Gln Ile Tyr Lys
225                 230                 235                 240 tac gtg gtg cac aac gtg gcg cac gcc ttc ggt aaa acc gcg acc ttc      768
Tyr Val Val His Asn Val Ala His Ala Phe Gly Lys Thr Ala Thr Phe
                245                 250                 255 atg ccg aag ccc atg ttc ggc gac aac ggt tcc ggc atg cac tgc cac      816
Met Pro Lys Pro Met Phe Gly Asp Asn Gly Ser Gly Met His Cys His
            260                 265                 270 atg tcg ctg tcc aag aac ggc acc aac ctg ttc gcc ggc gac aaa tac      864
Met Ser Leu Ser Lys Asn Gly Thr Asn Leu Phe Ala Gly Asp Lys Tyr
        275                 280                 285 ggc ggc ctg tct gaa acc gca ctg ttc tac atc ggc ggt atc atc aag      912
Gly Gly Leu Ser Glu Thr Ala Leu Phe Tyr Ile Gly Gly Ile Ile Lys
    290                 295                 300 cac gcc aag gcg atc aac gcg ctg gcc aac ccg acc acc aac tcg tac      960
His Ala Lys Ala Ile Asn Ala Leu Ala Asn Pro Thr Thr Asn Ser Tyr
305                 310                 315                 320 aaa cgt ctg gtg cca ggc tac gaa gcg ccg gtg atg ctg gct tac tcc     1008
Lys Arg Leu Val Pro Gly Tyr Glu Ala Pro Val Met Leu Ala Tyr Ser
                325                 330                 335 gcc cgt aac cgc tcc gcg tcc atc cgt atc ccg gtg gtc gcc agc ccg     1056
Ala Arg Asn Arg Ser Ala Ser Ile Arg Ile Pro Val Val Ala Ser Pro
            340                 345                 350 aaa gcg cgc cgc atc gaa gcc cgc ttc ccg gat ccg gcg gct aac cca     1104
Lys Ala Arg Arg Ile Glu Ala Arg Phe Pro Asp Pro Ala Ala Asn Pro
        355                 360                 365 tac ctg tgc ttc gcc gca ctg ctg atg gcc ggc ctg gac ggc atc atc     1152
Tyr Leu Cys Phe Ala Ala Leu Leu Met Ala Gly Leu Asp Gly Ile Ile
    370                 375                 380 aac aag atc cac cct ggc gac gcc atg gac aaa aac ctg tac gac ctg     1200
Asn Lys Ile His Pro Gly Asp Ala Met Asp Lys Asn Leu Tyr Asp Leu
385                 390                 395                 400 ccg ccg gaa gaa gaa gcc gag atc cca aaa gtg gcc ggc tcg ctg gac     1248
Pro Pro Glu Glu Glu Ala Glu Ile Pro Lys Val Ala Gly Ser Leu Asp
                405                 410                 415 gag gcg atg gcc gcg ctg aac gaa gac cgc gag ttc ctg acc cgc ggc     1296
Glu Ala Met Ala Ala Leu Asn Glu Asp Arg Glu Phe Leu Thr Arg Gly
            420                 425                 430 ggc gtg ttc acc gac gat gcg atc gat gcc tac atc gaa ctg cgc aaa     1344
Gly Val Phe Thr Asp Asp Ala Ile Asp Ala Tyr Ile Glu Leu Arg Lys
        435                 440                 445 gaa gag atg gac cgc gtt cgc atg acg cca cac ccg gtc gag ttc gaa     1392
Glu Glu Met Asp Arg Val Arg Met Thr Pro His Pro Val Glu Phe Glu
    450                 455                 460 ctg tac tac agc gtc taa                                              1410
Leu Tyr Tyr Ser Val  *
465

<210> SEQ ID NO 18
<211> LENGTH: 469
<212> TYPE: PRT
<213> ORGANISM: Artificial Sequence
<220> FEATURE:
<223> OTHER INFORMATION: AGS1 variant amino acid sequence (AGS1M9)

<400> SEQUENCE: 18

Met Thr Ala Glu His Val Leu Thr Met Leu Asn Glu His Glu Val Lys
```

-continued

```
               1               5                  10                 15
Phe Val Asp Leu Arg Phe Thr Asp Thr Lys Gly Lys Glu Gln His Val
                    20                  25                  30
Thr Ile Pro Ala His Gln Val Asn Ala Asp Phe Phe Glu Glu Gly Lys
                35                  40                  45
Met Phe Asp Gly Ser Ser Ile Gly Gly Trp Lys Gly Ile Asn Glu Ser
 50                  55                  60
Asp Met Val Leu Met Pro Asp Val Ser Thr Ala Val Leu Asp Pro Phe
 65                  70                  75                  80
Phe Glu Glu Pro Thr Leu Ile Ile Arg Cys Asp Ile Leu Glu Pro Gly
                    85                  90                  95
Thr Met Gln Gly Tyr Asp Arg Asp Pro Arg Ser Ile Ser Lys Arg Ala
                100                 105                 110
Glu Asp Phe Leu Arg Ser Ser Gly Ile Ala Asp Thr Val Leu Phe Gly
                115                 120                 125
Pro Glu Pro Glu Phe Phe Leu Phe Asp Asp Ile Arg Phe Gly Ser Ser
                130                 135                 140
Ile Arg Gly Ser His Val Ala Ile Asp Asp Ile Glu Gly Ala Trp Asn
145                 150                 155                 160
Ser Gly Thr Lys Tyr Asp Gly Gly Asn Lys Gly His Arg Pro Ala Val
                165                 170                 175
Lys Gly Gly Tyr Phe Pro Val Pro Pro Val Asp Ser Ser Gln Asp Leu
                180                 185                 190
Arg Ser Thr Met Cys Leu Thr Met Glu Glu Met Gly Leu Val Val Glu
                195                 200                 205
Ala His His His Glu Val Ala Thr Ala Gly Gln Asn Glu Val Ala Thr
                210                 215                 220
Arg Phe Asn Thr Met Thr Lys Lys Ala Asp Glu Ile Gln Ile Tyr Lys
225                 230                 235                 240
Tyr Val Val His Asn Val Ala His Ala Phe Gly Lys Thr Ala Thr Phe
                245                 250                 255
Met Pro Lys Pro Met Phe Gly Asp Asn Gly Ser Gly Met His Cys His
                260                 265                 270
Met Ser Leu Ser Lys Asn Gly Thr Asn Leu Phe Ala Gly Asp Lys Tyr
                275                 280                 285
Gly Gly Leu Ser Glu Thr Ala Leu Phe Tyr Ile Gly Gly Ile Ile Lys
                290                 295                 300
His Ala Lys Ala Ile Asn Ala Leu Ala Asn Pro Thr Thr Asn Ser Tyr
305                 310                 315                 320
Lys Arg Leu Val Pro Gly Tyr Glu Ala Pro Val Met Leu Ala Tyr Ser
                325                 330                 335
Ala Arg Asn Arg Ser Ala Ser Ile Arg Ile Pro Val Val Ala Ser Pro
                340                 345                 350
Lys Ala Arg Arg Ile Glu Ala Arg Phe Pro Asp Pro Ala Ala Asn Pro
                355                 360                 365
Tyr Leu Cys Phe Ala Ala Leu Leu Met Ala Gly Leu Asp Gly Ile Ile
                370                 375                 380
Asn Lys Ile His Pro Gly Asp Ala Met Asp Lys Asn Leu Tyr Asp Leu
385                 390                 395                 400
Pro Pro Glu Glu Glu Ala Glu Ile Pro Lys Val Ala Gly Ser Leu Asp
                405                 410                 415
Glu Ala Met Ala Ala Leu Asn Glu Asp Arg Glu Phe Leu Thr Arg Gly
                420                 425                 430
```

```
Gly Val Phe Thr Asp Asp Ala Ile Asp Ala Tyr Ile Glu Leu Arg Lys
        435                 440                 445

Glu Glu Met Asp Arg Val Arg Met Thr Pro His Pro Val Glu Phe Glu
    450                 455                 460

Leu Tyr Tyr Ser Val
465

<210> SEQ ID NO 19
<211> LENGTH: 1410
<212> TYPE: DNA
<213> ORGANISM: Artificial Sequence
<220> FEATURE:
<223> OTHER INFORMATION: ags1 variant nucleotide sequence (ags1m10)
<221> NAME/KEY: CDS
<222> LOCATION: (1)...(1410)

<400> SEQUENCE: 19 atg tcc gct gaa cac gtt ttg acg atg ctg aat gag cat gaa gtg aaa     48
Met Ser Ala Glu His Val Leu Thr Met Leu Asn Glu His Glu Val Lys
 1               5                  10                  15 ttc gta gac ctg cgt ttc act gac acc aag ggt aag gaa cag cac gtg     96
Phe Val Asp Leu Arg Phe Thr Asp Thr Lys Gly Lys Glu Gln His Val
            20                  25                  30 act atc ccg gct cac cag gta aac gcc gac ttc ttc gaa gaa ggt aaa    144
Thr Ile Pro Ala His Gln Val Asn Ala Asp Phe Phe Glu Glu Gly Lys
        35                  40                  45 atg ttt gac ggc tcc tct atc ggt ggt tgg aag ggc atc aac gaa tct    192
Met Phe Asp Gly Ser Ser Ile Gly Gly Trp Lys Gly Ile Asn Glu Ser
    50                  55                  60 gac atg gtg ctg atg ccg gac gcc agc acg gcg gtt ctg gat ccg ttc    240
Asp Met Val Leu Met Pro Asp Ala Ser Thr Ala Val Leu Asp Pro Phe
65                  70                  75                  80 ttc gaa gaa cct acg ctg atc att cgc tgt gac att ctc gag ccg ggc    288
Phe Glu Glu Pro Thr Leu Ile Ile Arg Cys Asp Ile Leu Glu Pro Gly
                85                  90                  95 acc atg caa ggc tac gat cgc gac ccg cgt tcc atc tcc aaa cgc gcc    336
Thr Met Gln Gly Tyr Asp Arg Asp Pro Arg Ser Ile Ser Lys Arg Ala
           100                 105                 110 gaa gac ttc ctg cgc tcc tcc ggc atc gcg gac acc gtg ctg ttc ggg    384
Glu Asp Phe Leu Arg Ser Ser Gly Ile Ala Asp Thr Val Leu Phe Gly
       115                 120                 125 cca gag cct gag ttc ttc ctg ttc gac gac atc cgc ttc ggc agc agc    432
Pro Glu Pro Glu Phe Phe Leu Phe Asp Asp Ile Arg Phe Gly Ser Ser
   130                 135                 140 atc cgc ggt tcc cac atg gcg atc gac gat atc gaa ggc gcc tgg aac    480
Ile Arg Gly Ser His Met Ala Ile Asp Asp Ile Glu Gly Ala Trp Asn
145                 150                 155                 160 tcc ggc aca aaa tac gac ggc ggc aac aaa ggc cac cgt ccg gcg gtg    528
Ser Gly Thr Lys Tyr Asp Gly Gly Asn Lys Gly His Arg Pro Ala Val
                165                 170                 175 aaa ggc ggt tac ttc ccg gtt cca ccg gtc gac tct tcg cag gat ctg    576
Lys Gly Gly Tyr Phe Pro Val Pro Pro Val Asp Ser Ser Gln Asp Leu
            180                 185                 190 cgt tcc acc atg tgt ctg acc atg gaa gag atg ggc ctg gtg gtt gaa    624
Arg Ser Thr Met Cys Leu Thr Met Glu Glu Met Gly Leu Val Val Glu
        195                 200                 205 gcg cac cac cac gaa gtg gcg acc gcc ggt cag aac gaa gtg gca acc    672
Ala His His His Glu Val Ala Thr Ala Gly Gln Asn Glu Val Ala Thr
    210                 215                 220 cgc ttc aac acc atg acc aag aaa gcc gac gaa att cag atc tat aag    720
Arg Phe Asn Thr Met Thr Lys Lys Ala Asp Glu Ile Gln Ile Tyr Lys
225                 230                 235                 240
```

```
tac gtg gtg cac aac gtg gcg cac gcc ttc ggt aaa acc gcg acc ttc         768
Tyr Val Val His Asn Val Ala His Ala Phe Gly Lys Thr Ala Thr Phe
                    245                 250                 255 atg ccg aag ccc atg ttc ggc gac aac ggt tcc ggc atg cac tgc cac         816
Met Pro Lys Pro Met Phe Gly Asp Asn Gly Ser Gly Met His Cys His
            260                 265                 270 atg tcg ctg tcc aag aac ggc acc aac ctg ttc gcc ggc gac aaa tac         864
Met Ser Leu Ser Lys Asn Gly Thr Asn Leu Phe Ala Gly Asp Lys Tyr
        275                 280                 285 ggc ggc ctg tct gaa acc gca ctg ttc tac atc ggc ggt atc atc aag         912
Gly Gly Leu Ser Glu Thr Ala Leu Phe Tyr Ile Gly Gly Ile Ile Lys
    290                 295                 300 cac gcc aag gcg atc aac gcg ctg gcc aac ccg acc acc aac tcg tac         960
His Ala Lys Ala Ile Asn Ala Leu Ala Asn Pro Thr Thr Asn Ser Tyr
305                 310                 315                 320 aaa cgt ctg gtg cca ggc tac gaa gcg ccg gtg atg ctg gct tac tcc        1008
Lys Arg Leu Val Pro Gly Tyr Glu Ala Pro Val Met Leu Ala Tyr Ser
                    325                 330                 335 gcc cgt aac cgc tcc gcg tcc atc cgt atc ccg gtg gtc gcc agc ccg        1056
Ala Arg Asn Arg Ser Ala Ser Ile Arg Ile Pro Val Val Ala Ser Pro
                340                 345                 350 aaa gcg cgc cgc atc gaa gcc cgc ttc ccg gat ccg gcg gct aac cca        1104
Lys Ala Arg Arg Ile Glu Ala Arg Phe Pro Asp Pro Ala Ala Asn Pro
            355                 360                 365 tac ctg tgc ttc gcc gca ctg ctg atg gcc ggc ctg gac ggc atc atc        1152
Tyr Leu Cys Phe Ala Ala Leu Leu Met Ala Gly Leu Asp Gly Ile Ile
        370                 375                 380 aac aag atc cac cct ggc gac gcc atg gac aaa aac ctg tat gac ctg        1200
Asn Lys Ile His Pro Gly Asp Ala Met Asp Lys Asn Leu Tyr Asp Leu
385                 390                 395                 400 ccg ccg gaa gaa gaa gcc gag atc cca aaa gtg gcc ggc tcg ctg gac        1248
Pro Pro Glu Glu Glu Ala Glu Ile Pro Lys Val Ala Gly Ser Leu Asp
                    405                 410                 415 gag gcg atg gcc gcg ctg aac gaa gac cgc gag ttc ctg acc cgc ggc        1296
Glu Ala Met Ala Ala Leu Asn Glu Asp Arg Glu Phe Leu Thr Arg Gly
                420                 425                 430 ggc gtg ttc acc gac gat gcg atc gat gcc tac atc gaa ctg cgc aaa        1344
Gly Val Phe Thr Asp Asp Ala Ile Asp Ala Tyr Ile Glu Leu Arg Lys
            435                 440                 445 gaa gag atg gac cgc gtt cgc atg acg cca cac ccg gtc gag ttc gaa        1392
Glu Glu Met Asp Arg Val Arg Met Thr Pro His Pro Val Glu Phe Glu
        450                 455                 460 ctg tac tac agc gtc taa                                                1410
Leu Tyr Tyr Ser Val  *
465

<210> SEQ ID NO 20
<211> LENGTH: 469
<212> TYPE: PRT
<213> ORGANISM: Artificial Sequence
<220> FEATURE:
<223> OTHER INFORMATION: AGS1 variant amino acid sequence (AGS1M10)

<400> SEQUENCE: 20

Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
                20                  25                  30

Thr Ile Pro Ala His Gln Val Asn Ala Asp Phe Phe Glu Glu Gly Lys
        35                  40                  45
```

```
Met Phe Asp Gly Ser Ser Ile Gly Gly Trp Lys Gly Ile Asn Glu Ser
    50                  55                  60

Asp Met Val Leu Met Pro Asp Ala Ser Thr Ala Val Leu Asp Pro Phe
65                  70                  75                  80

Phe Glu Glu Pro Thr Leu Ile Ile Arg Cys Asp Ile Leu Glu Pro Gly
                    85                  90                  95

Thr Met Gln Gly Tyr Asp Arg Asp Pro Arg Ser Ile Ser Lys Arg Ala
                100                 105                 110

Glu Asp Phe Leu Arg Ser Ser Gly Ile Ala Asp Thr Val Leu Phe Gly
            115                 120                 125

Pro Glu Pro Glu Phe Phe Leu Phe Asp Asp Ile Arg Phe Gly Ser Ser
    130                 135                 140

Ile Arg Gly Ser His Met Ala Ile Asp Asp Ile Glu Gly Ala Trp Asn
145                 150                 155                 160

Ser Gly Thr Lys Tyr Asp Gly Gly Asn Lys Gly His Arg Pro Ala Val
                165                 170                 175

Lys Gly Gly Tyr Phe Pro Val Pro Pro Val Asp Ser Ser Gln Asp Leu
                180                 185                 190

Arg Ser Thr Met Cys Leu Thr Met Glu Glu Met Gly Leu Val Val Glu
            195                 200                 205

Ala His His His Glu Val Ala Thr Ala Gly Gln Asn Glu Val Ala Thr
    210                 215                 220

Arg Phe Asn Thr Met Thr Lys Lys Ala Asp Glu Ile Gln Ile Tyr Lys
225                 230                 235                 240

Tyr Val Val His Asn Val Ala His Ala Phe Gly Lys Thr Ala Thr Phe
                245                 250                 255

Met Pro Lys Pro Met Phe Gly Asp Asn Gly Ser Gly Met His Cys His
                260                 265                 270

Met Ser Leu Ser Lys Asn Gly Thr Asn Leu Phe Ala Gly Asp Lys Tyr
            275                 280                 285

Gly Gly Leu Ser Glu Thr Ala Leu Phe Tyr Ile Gly Gly Ile Ile Lys
    290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Ala Ser Pro
                340                 345                 350

Lys Ala Arg Arg Ile Glu Ala Arg Phe Pro Asp Pro Ala Ala Asn Pro
            355                 360                 365

Tyr Leu Cys Phe Ala Ala Leu Leu Met Ala Gly Leu Asp Gly Ile Ile
    370                 375                 380

Asn Lys Ile His Pro Gly Asp Ala Met Asp Lys Asn Leu Tyr Asp Leu
385                 390                 395                 400

Pro Pro Glu Glu Glu Ala Glu Ile Pro Lys Val Ala Gly Ser Leu Asp
                405                 410                 415

Glu Ala Met Ala Ala Leu Asn Glu Asp Arg Glu Phe Leu Thr Arg Gly
            420                 425                 430

Gly Val Phe Thr Asp Asp Ala Ile Asp Ala Tyr Ile Glu Leu Arg Lys
    435                 440                 445

Glu Glu Met Asp Arg Val Arg Met Thr Pro His Pro Val Glu Phe Glu
    450                 455                 460

Leu Tyr Tyr Ser Val
465
```

<210> SEQ ID NO 21
<211> LENGTH: 1410
<212> TYPE: DNA
<213> ORGANISM: Artificial Sequence
<220> FEATURE:
<223> OTHER INFORMATION: ags1 variant nucleotide sequence (ags1m11)
<221> NAME/KEY: CDS
<222> LOCATION: (1)...(1410)

<400> SEQUENCE: 21

| | | | | | | | | | | | | | | | | |
|---|---|---|---|---|---|---|---|---|---|---|---|---|---|---|---|---|
| atg | tcc | gct | gaa | cac | gtt | ttg | acg | atg | ctc | aat | gag | cat | gaa | gtg | aaa | 48 |
| Met | Ser | Ala | Glu | His | Val | Leu | Thr | Met | Leu | Asn | Glu | His | Glu | Val | Lys | |
| 1 | | | | 5 | | | | | 10 | | | | | 15 | | |
| ttc | gta | gac | ctg | cgt | ttc | act | gac | acc | aag | ggt | aag | gaa | cag | cac | gtg | 96 |
| Phe | Val | Asp | Leu | Arg | Phe | Thr | Asp | Thr | Lys | Gly | Lys | Glu | Gln | His | Val | |
| | | | 20 | | | | | 25 | | | | | 30 | | | |
| act | atc | ccg | gct | cac | cag | gta | aac | gcc | gac | ttc | ttc | gaa | gaa | ggt | aaa | 144 |
| Thr | Ile | Pro | Ala | His | Gln | Val | Asn | Ala | Asp | Phe | Phe | Glu | Glu | Gly | Lys | |
| | 35 | | | | | 40 | | | | | 45 | | | | | |
| atg | ttt | gac | ggc | tcc | tct | atc | gct | ggt | tgg | aag | ggc | atc | aac | gaa | tct | 192 |
| Met | Phe | Asp | Gly | Ser | Ser | Ile | Ala | Gly | Trp | Lys | Gly | Ile | Asn | Glu | Ser | |
| 50 | | | | | 55 | | | | | 60 | | | | | | |
| gac | atg | gtg | ctg | atg | ccg | gac | gcc | agc | acg | gcg | gtt | ctg | gat | ccg | ttc | 240 |
| Asp | Met | Val | Leu | Met | Pro | Asp | Ala | Ser | Thr | Ala | Val | Leu | Asp | Pro | Phe | |
| 65 | | | | | 70 | | | | | 75 | | | | | 80 | |
| ttc | gaa | gaa | cct | acg | ctg | atc | att | cgc | tgt | gac | att | ctc | gag | ccg | ggc | 288 |
| Phe | Glu | Glu | Pro | Thr | Leu | Ile | Ile | Arg | Cys | Asp | Ile | Leu | Glu | Pro | Gly | |
| | | | | 85 | | | | | 90 | | | | | 95 | | |
| acc | atg | caa | ggc | tac | gat | cgc | gac | ccg | cgt | tcc | atc | tcc | aaa | cgc | gcc | 336 |
| Thr | Met | Gln | Gly | Tyr | Asp | Arg | Asp | Pro | Arg | Ser | Ile | Ser | Lys | Arg | Ala | |
| | | | 100 | | | | | 105 | | | | | 110 | | | |
| gaa | gac | ttc | ctg | cgc | tcc | tcc | ggc | atc | gcg | gac | acc | gtg | ctg | ttc | ggg | 384 |
| Glu | Asp | Phe | Leu | Arg | Ser | Ser | Gly | Ile | Ala | Asp | Thr | Val | Leu | Phe | Gly | |
| | 115 | | | | | 120 | | | | | 125 | | | | | |
| cca | gag | cct | gag | ttc | ttc | ctg | ttc | gac | gac | atc | cgc | ttc | ggc | agc | agc | 432 |
| Pro | Glu | Pro | Glu | Phe | Phe | Leu | Phe | Asp | Asp | Ile | Arg | Phe | Gly | Ser | Ser | |
| 130 | | | | | 135 | | | | | 140 | | | | | | |
| atc | cgc | ggt | tcc | cac | gtg | gcg | atc | gac | gat | atc | gaa | ggc | gcc | tgg | aac | 480 |
| Ile | Arg | Gly | Ser | His | Val | Ala | Ile | Asp | Asp | Ile | Glu | Gly | Ala | Trp | Asn | |
| 145 | | | | | 150 | | | | | 155 | | | | | 160 | |
| tcc | ggc | aca | aaa | tac | gac | ggc | ggc | aac | aaa | ggc | cac | cgt | ccg | gcg | gtg | 528 |
| Ser | Gly | Thr | Lys | Tyr | Asp | Gly | Gly | Asn | Lys | Gly | His | Arg | Pro | Ala | Val | |
| | | | | 165 | | | | | 170 | | | | | 175 | | |
| aaa | ggc | ggt | tac | ttc | ccg | gtt | cca | ccg | gtc | gac | tct | tcg | cag | gat | ctg | 576 |
| Lys | Gly | Gly | Tyr | Phe | Pro | Val | Pro | Pro | Val | Asp | Ser | Ser | Gln | Asp | Leu | |
| | | | 180 | | | | | 185 | | | | | 190 | | | |
| cgt | tcc | acc | atg | tgt | ctg | acc | atg | gaa | gag | atg | ggc | ctg | gtg | gtt | gaa | 624 |
| Arg | Ser | Thr | Met | Cys | Leu | Thr | Met | Glu | Glu | Met | Gly | Leu | Val | Val | Glu | |
| | 195 | | | | | 200 | | | | | 205 | | | | | |
| gcg | cac | cac | cac | gaa | gag | gcg | acc | gcc | ggt | cag | aac | gaa | gtg | gca | acc | 672 |
| Ala | His | His | His | Glu | Glu | Ala | Thr | Ala | Gly | Gln | Asn | Glu | Val | Ala | Thr | |
| 210 | | | | | 215 | | | | | 220 | | | | | | |
| cgc | ttc | aac | acc | atg | acc | aag | aaa | gcc | gac | gaa | att | cag | atc | tat | aag | 720 |
| Arg | Phe | Asn | Thr | Met | Thr | Lys | Lys | Ala | Asp | Glu | Ile | Gln | Ile | Tyr | Lys | |
| 225 | | | | | 230 | | | | | 235 | | | | | 240 | |
| tac | gtg | gtg | cac | aac | gtg | gcg | cac | gcc | ttc | ggt | aaa | acc | gcg | acc | ttc | 768 |
| Tyr | Val | Val | His | Asn | Val | Ala | His | Ala | Phe | Gly | Lys | Thr | Ala | Thr | Phe | |
| | | | | 245 | | | | | 250 | | | | | 255 | | |
| atg | ccg | aag | ccc | atg | ttc | ggc | gac | aac | ggt | tcc | ggc | atg | cac | tgc | cac | 816 |
| Met | Pro | Lys | Pro | Met | Phe | Gly | Asp | Asn | Gly | Ser | Gly | Met | His | Cys | His | |
| | | | 260 | | | | | 265 | | | | | 270 | | | |

```
atg tcg ctg tcc aag aac ggc acc aac ctg ttc gcc ggc gac aaa tac      864
Met Ser Leu Ser Lys Asn Gly Thr Asn Leu Phe Ala Gly Asp Lys Tyr
    275                 280                 285 ggc ggc cta tct gaa acc gca ctg ttc tac atc ggc ggt atc att aag      912
Gly Gly Leu Ser Glu Thr Ala Leu Phe Tyr Ile Gly Gly Ile Ile Lys
290                 295                 300 cac gcc aag gcg atc aac gcg ctg gcc aac ccg acc acc aac tcg tac      960
His Ala Lys Ala Ile Asn Ala Leu Ala Asn Pro Thr Thr Asn Ser Tyr
305                 310                 315                 320 aaa cgt ctg gtg cca ggc tac gaa gcg ccg gtg atg ctg gct tac tcc     1008
Lys Arg Leu Val Pro Gly Tyr Glu Ala Pro Val Met Leu Ala Tyr Ser
            325                 330                 335 gcc cgt aac cgc tcc gcg tcc atc cgt atc ccg gtg gtc gcc agc ccg     1056
Ala Arg Asn Arg Ser Ala Ser Ile Arg Ile Pro Val Val Ala Ser Pro
        340                 345                 350 aaa gcg cgc cgc atc gaa gcc cgc ttc ccg gat ccg gcg gct aac cca     1104
Lys Ala Arg Arg Ile Glu Ala Arg Phe Pro Asp Pro Ala Ala Asn Pro
    355                 360                 365 tac ctg tgc ttc gcc gca ctg ctg atg gcc ggc ctg gac ggc atc atc     1152
Tyr Leu Cys Phe Ala Ala Leu Leu Met Ala Gly Leu Asp Gly Ile Ile
370                 375                 380 aac aag atc cac cct ggc gac gcc atg gat aaa aac ctg tac gac ctg     1200
Asn Lys Ile His Pro Gly Asp Ala Met Asp Lys Asn Leu Tyr Asp Leu
385                 390                 395                 400 ccg ccg gaa gaa gaa gcc gag atc cca aaa gtg gcc ggc tcg ctg gac     1248
Pro Pro Glu Glu Glu Ala Glu Ile Pro Lys Val Ala Gly Ser Leu Asp
            405                 410                 415 gag gcg atg gcc gcg ctg aac gaa gac cgc gag ttc ctg acc cgc ggc     1296
Glu Ala Met Ala Ala Leu Asn Glu Asp Arg Glu Phe Leu Thr Arg Gly
        420                 425                 430 ggc gtg ttc acc gac gat gcg atc gat gcc tac atc gaa ctg cgc aaa     1344
Gly Val Phe Thr Asp Asp Ala Ile Asp Ala Tyr Ile Glu Leu Arg Lys
    435                 440                 445 gaa gag atg gac cgc gtt cgc atg acg cca cat ccg gtc gag ttc gaa     1392
Glu Glu Met Asp Arg Val Arg Met Thr Pro His Pro Val Glu Phe Glu
450                 455                 460 ctg tac tac agc gtc taa                                             1410
Leu Tyr Tyr Ser Val  *
465

<210> SEQ ID NO 22
<211> LENGTH: 469
<212> TYPE: PRT
<213> ORGANISM: Artificial Sequence
<220> FEATURE:
<223> OTHER INFORMATION: AGS1 variant amino acid sequence (AGS1M11)

<400> SEQUENCE: 22

Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
            20                  25                  30

Thr Ile Pro Ala His Gln Val Asn Ala Asp Phe Phe Glu Glu Gly Lys
        35                  40                  45

Met Phe Asp Gly Ser Ser Ile Ala Gly Trp Lys Gly Ile Asn Glu Ser
    50                  55                  60

Asp Met Val Leu Met Pro Asp Ala Ser Thr Ala Val Leu Asp Pro Phe
65                  70                  75                  80

Phe Glu Glu Pro Thr Leu Ile Ile Arg Cys Asp Ile Leu Glu Pro Gly
                85                  90                  95
```

Thr Met Gln Gly Tyr Asp Arg Asp Pro Arg Ser Ile Ser Lys Arg Ala
            100                 105                 110

Glu Asp Phe Leu Arg Ser Ser Gly Ile Ala Asp Thr Val Leu Phe Gly
        115                 120                 125

Pro Glu Pro Glu Phe Phe Leu Phe Asp Asp Ile Arg Phe Gly Ser Ser
130                 135                 140

Ile Arg Gly Ser His Val Ala Ile Asp Asp Ile Glu Gly Ala Trp Asn
145                 150                 155                 160

Ser Gly Thr Lys Tyr Asp Gly Gly Asn Lys Gly His Arg Pro Ala Val
                165                 170                 175

Lys Gly Gly Tyr Phe Pro Val Pro Pro Val Asp Ser Ser Gln Asp Leu
            180                 185                 190

Arg Ser Thr Met Cys Leu Thr Met Glu Glu Met Gly Leu Val Val Glu
            195                 200                 205

Ala His His His Glu Glu Ala Thr Ala Gly Gln Asn Glu Val Ala Thr
        210                 215                 220

Arg Phe Asn Thr Met Thr Lys Lys Ala Asp Glu Ile Gln Ile Tyr Lys
225                 230                 235                 240

Tyr Val Val His Asn Val Ala His Ala Phe Gly Lys Thr Ala Thr Phe
                245                 250                 255

Met Pro Lys Pro Met Phe Gly Asp Asn Gly Ser Gly Met His Cys His
            260                 265                 270

Met Ser Leu Ser Lys Asn Gly Thr Asn Leu Phe Ala Gly Asp Lys Tyr
        275                 280                 285

Gly Gly Leu Ser Glu Thr Ala Leu Phe Tyr Ile Gly Gly Ile Ile Lys
        290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Ala Ser Pro
            340                 345                 350

Lys Ala Arg Arg Ile Glu Ala Arg Phe Pro Asp Pro Ala Ala Asn Pro
        355                 360                 365

Tyr Leu Cys Phe Ala Ala Leu Leu Met Ala Gly Leu Asp Gly Ile Ile
        370                 375                 380

Asn Lys Ile His Pro Gly Asp Ala Met Asp Lys Asn Leu Tyr Asp Leu
385                 390                 395                 400

Pro Pro Glu Glu Glu Ala Glu Ile Pro Lys Val Ala Gly Ser Leu Asp
                405                 410                 415

Glu Ala Met Ala Ala Leu Asn Glu Asp Arg Glu Phe Leu Thr Arg Gly
            420                 425                 430

Gly Val Phe Thr Asp Asp Ala Ile Asp Ala Tyr Ile Glu Leu Arg Lys
        435                 440                 445

Glu Glu Met Asp Arg Val Arg Met Thr Pro His Pro Val Glu Phe Glu
        450                 455                 460

Leu Tyr Tyr Ser Val
465

<210> SEQ ID NO 23
<211> LENGTH: 1410
<212> TYPE: DNA
<213> ORGANISM: Artificial Sequence
<220> FEATURE:
<223> OTHER INFORMATION: ags1 variant nucleotide sequence (ags1m12)

<221> NAME/KEY: CDS
<222> LOCATION: (1)...(1410)

<400> SEQUENCE: 23

| | | | | | | | | | | | | | | | | |
|---|---|---|---|---|---|---|---|---|---|---|---|---|---|---|---|---|
| atg | tcc | gct | gaa | cac | gtt | ttg | acg | atg | ctg | aat | gag | cat | gaa | gtg | aaa | 48 |
| Met | Ser | Ala | Glu | His | Val | Leu | Thr | Met | Leu | Asn | Glu | His | Glu | Val | Lys | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttc | gta | gac | ctg | cgt | ttc | act | gac | acc | aag | ggt | aag | gaa | cag | cac | gtg | 96 |
| Phe | Val | Asp | Leu | Arg | Phe | Thr | Asp | Thr | Lys | Gly | Lys | Glu | Gln | His | Val | |
| | | | 20 | | | | | 25 | | | | | 30 | | | |

| | | | | | | | | | | | | | | | | |
|---|---|---|---|---|---|---|---|---|---|---|---|---|---|---|---|---|
| act | atc | ccg | gct | cac | cag | gta | aac | gcc | gac | ttc | ttc | gaa | gaa | ggt | aaa | 144 |
| Thr | Ile | Pro | Ala | His | Gln | Val | Asn | Ala | Asp | Phe | Phe | Glu | Glu | Gly | Lys | |
| | | 35 | | | | | 40 | | | | | 45 | | | | |

| | | | | | | | | | | | | | | | | |
|---|---|---|---|---|---|---|---|---|---|---|---|---|---|---|---|---|
| atg | ttt | gac | ggc | tcc | tct | atc | ggt | ggt | tgg | aag | ggc | atc | aac | gaa | tct | 192 |
| Met | Phe | Asp | Gly | Ser | Ser | Ile | Gly | Gly | Trp | Lys | Gly | Ile | Asn | Glu | Ser | |
| 50 | | | | | 55 | | | | | 60 | | | | | | |

| | | | | | | | | | | | | | | | | |
|---|---|---|---|---|---|---|---|---|---|---|---|---|---|---|---|---|
| gac | atg | gtg | ctg | atg | ccg | gac | gcc | agc | acg | gcg | gtt | ctg | gat | ccg | ttc | 240 |
| Asp | Met | Val | Leu | Met | Pro | Asp | Ala | Ser | Thr | Ala | Val | Leu | Asp | Pro | Phe | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| ttc | gaa | gaa | cct | acg | ctg | atc | att | cgc | tgt | gac | att | ctc | gag | ccg | ggc | 288 |
| Phe | Glu | Glu | Pro | Thr | Leu | Ile | Ile | Arg | Cys | Asp | Ile | Leu | Glu | Pro | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| acc | atg | caa | ggc | tac | gat | cgc | gac | ccg | cgt | tcc | atc | tcc | aaa | cgc | gcc | 336 |
| Thr | Met | Gln | Gly | Tyr | Asp | Arg | Asp | Pro | Arg | Ser | Ile | Ser | Lys | Arg | Ala | |
| | | | 100 | | | | | 105 | | | | | 110 | | | |

| | | | | | | | | | | | | | | | | |
|---|---|---|---|---|---|---|---|---|---|---|---|---|---|---|---|---|
| gaa | gac | ttc | ctg | cgc | tcc | tcc | ggc | atc | gcg | gac | acc | gtg | ctg | ttc | ggg | 384 |
| Glu | Asp | Phe | Leu | Arg | Ser | Ser | Gly | Ile | Ala | Asp | Thr | Val | Leu | Phe | Gly | |
| | | | 115 | | | | | 120 | | | | | 125 | | | |

| | | | | | | | | | | | | | | | | |
|---|---|---|---|---|---|---|---|---|---|---|---|---|---|---|---|---|
| cca | gag | cct | gag | ttc | ttc | ctg | ttc | gac | gac | atc | cgc | ttc | ggc | agc | agc | 432 |
| Pro | Glu | Pro | Glu | Phe | Phe | Leu | Phe | Asp | Asp | Ile | Arg | Phe | Gly | Ser | Ser | |
| | 130 | | | | | 135 | | | | | 140 | | | | | |

| | | | | | | | | | | | | | | | | |
|---|---|---|---|---|---|---|---|---|---|---|---|---|---|---|---|---|
| atc | cgc | ggt | tcc | cac | gtg | gcg | atc | gac | gat | atc | gaa | ggc | gcc | tgg | aac | 480 |
| Ile | Arg | Gly | Ser | His | Val | Ala | Ile | Asp | Asp | Ile | Glu | Gly | Ala | Trp | Asn | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tcc | ggc | aca | aaa | tac | gat | ggc | ggc | aac | aaa | ggc | cac | cgt | ccg | gcg | gtg | 528 |
| Ser | Gly | Thr | Lys | Tyr | Asp | Gly | Gly | Asn | Lys | Gly | His | Arg | Pro | Ala | Val | |
| | | | 165 | | | | | 170 | | | | | 175 | | | |

| | | | | | | | | | | | | | | | | |
|---|---|---|---|---|---|---|---|---|---|---|---|---|---|---|---|---|
| aaa | ggc | ggt | tac | ttc | ccg | gtt | cca | ccg | gtc | gac | tct | tcg | cag | gat | ctg | 576 |
| Lys | Gly | Gly | Tyr | Phe | Pro | Val | Pro | Pro | Val | Asp | Ser | Ser | Gln | Asp | Leu | |
| | | | 180 | | | | | 185 | | | | | 190 | | | |

| | | | | | | | | | | | | | | | | |
|---|---|---|---|---|---|---|---|---|---|---|---|---|---|---|---|---|
| cgt | tcc | acc | atg | tgt | ctg | acc | atg | gaa | gag | atg | ggc | ctg | gtg | att | gaa | 624 |
| Arg | Ser | Thr | Met | Cys | Leu | Thr | Met | Glu | Glu | Met | Gly | Leu | Val | Ile | Glu | |
| | | | 195 | | | | | 200 | | | | | 205 | | | |

| | | | | | | | | | | | | | | | | |
|---|---|---|---|---|---|---|---|---|---|---|---|---|---|---|---|---|
| gcg | cac | cac | cac | gaa | atg | gcg | acc | gcc | ggt | cag | aac | gaa | gtg | gca | acc | 672 |
| Ala | His | His | His | Glu | Met | Ala | Thr | Ala | Gly | Gln | Asn | Glu | Val | Ala | Thr | |
| | 210 | | | | | 215 | | | | | 220 | | | | | |

| | | | | | | | | | | | | | | | | |
|---|---|---|---|---|---|---|---|---|---|---|---|---|---|---|---|---|
| cgc | ttc | aac | acc | atg | acc | aag | aaa | gcc | gac | gaa | att | cag | atc | tat | aag | 720 |
| Arg | Phe | Asn | Thr | Met | Thr | Lys | Lys | Ala | Asp | Glu | Ile | Gln | Ile | Tyr | Lys | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| tac | gtg | gtg | cac | aac | gtg | gcg | cac | gcc | ttc | ggt | aaa | acc | gcg | acc | ttc | 768 |
| Tyr | Val | Val | His | Asn | Val | Ala | His | Ala | Phe | Gly | Lys | Thr | Ala | Thr | Phe | |
| | | | | 245 | | | | | 250 | | | | | 255 | | |

| | | | | | | | | | | | | | | | | |
|---|---|---|---|---|---|---|---|---|---|---|---|---|---|---|---|---|
| atg | ccg | aag | ccc | atg | ttc | ggc | gac | aac | ggt | tcc | ggc | atg | cac | tgc | cac | 816 |
| Met | Pro | Lys | Pro | Met | Phe | Gly | Asp | Asn | Gly | Ser | Gly | Met | His | Cys | His | |
| | | 260 | | | | | 265 | | | | | 270 | | | | |

| | | | | | | | | | | | | | | | | |
|---|---|---|---|---|---|---|---|---|---|---|---|---|---|---|---|---|
| atg | tcg | ctg | tcc | aag | aac | ggc | acc | aac | ctg | ttc | gcc | ggc | gac | aaa | tac | 864 |
| Met | Ser | Leu | Ser | Lys | Asn | Gly | Thr | Asn | Leu | Phe | Ala | Gly | Asp | Lys | Tyr | |
| | | 275 | | | | | 280 | | | | | 285 | | | | |

| | | | | | | | | | | | | | | | | |
|---|---|---|---|---|---|---|---|---|---|---|---|---|---|---|---|---|
| ggc | ggc | ctg | tct | gaa | acc | gca | ctg | ttc | tac | atc | ggc | ggt | atc | atc | aag | 912 |
| Gly | Gly | Leu | Ser | Glu | Thr | Ala | Leu | Phe | Tyr | Ile | Gly | Gly | Ile | Ile | Lys | |
| | | 290 | | | | | 295 | | | | | 300 | | | | |

| | | | | | | | | | | | | | | | | |
|---|---|---|---|---|---|---|---|---|---|---|---|---|---|---|---|---|
| cac | gcc | aag | gcg | atc | aac | gcg | ctg | gcc | aac | ccg | acc | acc | aac | tcg | tac | 960 |
| His | Ala | Lys | Ala | Ile | Asn | Ala | Leu | Ala | Asn | Pro | Thr | Thr | Asn | Ser | Tyr | |
| 305 | | | | 310 | | | | | 315 | | | | | 320 | | |
| aaa | cgt | ctg | gtg | cca | ggc | tac | gaa | gcg | ccg | gtg | atg | ctg | gct | tac | tcc | 1008 |
| Lys | Arg | Leu | Val | Pro | Gly | Tyr | Glu | Ala | Pro | Val | Met | Leu | Ala | Tyr | Ser | |
| | | | | 325 | | | | | 330 | | | | | 335 | | |
| gcc | cgt | aac | cgc | tcc | gcg | tcc | atc | cgt | atc | ccg | gtg | gtc | gcc | agc | ccg | 1056 |
| Ala | Arg | Asn | Arg | Ser | Ala | Ser | Ile | Arg | Ile | Pro | Val | Val | Ala | Ser | Pro | |
| | | | 340 | | | | | 345 | | | | | 350 | | | |
| aaa | gcg | cgc | cgc | atc | gaa | gcc | cgc | ttc | ccg | gat | ccg | gcg | gct | aac | cca | 1104 |
| Lys | Ala | Arg | Arg | Ile | Glu | Ala | Arg | Phe | Pro | Asp | Pro | Ala | Ala | Asn | Pro | |
| | | 355 | | | | | 360 | | | | | 365 | | | | |
| tac | ctg | tgc | ttc | gcc | gca | ctg | ctg | atg | gcc | ggc | ctg | gac | ggc | atc | atc | 1152 |
| Tyr | Leu | Cys | Phe | Ala | Ala | Leu | Leu | Met | Ala | Gly | Leu | Asp | Gly | Ile | Ile | |
| | 370 | | | | | 375 | | | | | 380 | | | | | |
| aac | aag | atc | cac | cct | ggc | gac | gcc | atg | gac | aaa | aac | ctg | tac | gac | ctg | 1200 |
| Asn | Lys | Ile | His | Pro | Gly | Asp | Ala | Met | Asp | Lys | Asn | Leu | Tyr | Asp | Leu | |
| 385 | | | | 390 | | | | | 395 | | | | | 400 | | |
| ccg | ccg | gaa | gaa | gaa | gcc | gag | atc | cca | aaa | gtg | gcc | ggc | tcg | ctg | gac | 1248 |
| Pro | Pro | Glu | Glu | Glu | Ala | Glu | Ile | Pro | Lys | Val | Ala | Gly | Ser | Leu | Asp | |
| | | | | 405 | | | | | 410 | | | | | 415 | | |
| gag | gcg | atg | gcc | gcg | ctg | aac | gaa | gac | cgc | gag | ttc | ctg | acc | cgc | ggc | 1296 |
| Glu | Ala | Met | Ala | Ala | Leu | Asn | Glu | Asp | Arg | Glu | Phe | Leu | Thr | Arg | Gly | |
| | | | 420 | | | | | 425 | | | | | 430 | | | |
| ggc | gtg | ttc | acc | gac | gat | gcg | atc | gat | gcc | tac | atc | gaa | ctg | cgc | aaa | 1344 |
| Gly | Val | Phe | Thr | Asp | Asp | Ala | Ile | Asp | Ala | Tyr | Ile | Glu | Leu | Arg | Lys | |
| | | 435 | | | | | 440 | | | | | 445 | | | | |
| gaa | gag | atg | gac | cgc | gtt | cgc | atg | acg | cca | cac | ccg | gtc | gag | ttc | gaa | 1392 |
| Glu | Glu | Met | Asp | Arg | Val | Arg | Met | Thr | Pro | His | Pro | Val | Glu | Phe | Glu | |
| | 450 | | | | | 455 | | | | | 460 | | | | | |
| ctg | tac | tac | agc | gtc | taa | | | | | | | | | | | 1410 |
| Leu | Tyr | Tyr | Ser | Val | * | | | | | | | | | | | |
| 465 | | | | | | | | | | | | | | | | |

<210> SEQ ID NO 24
<211> LENGTH: 469
<212> TYPE: PRT
<213> ORGANISM: Artificial Sequence
<220> FEATURE:
<223> OTHER INFORMATION: AGS1 variant amino acid sequence (AGS1M12)

<400> SEQUENCE: 24

Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
            20                  25                  30

Thr Ile Pro Ala His Gln Val Asn Ala Asp Phe Phe Glu Glu Gly Lys
        35                  40                  45

Met Phe Asp Gly Ser Ser Ile Gly Gly Trp Lys Gly Ile Asn Glu Ser
    50                  55                  60

Asp Met Val Leu Met Pro Asp Ala Ser Thr Ala Val Leu Asp Pro Phe
65                  70                  75                  80

Phe Glu Glu Pro Thr Leu Ile Ile Arg Cys Asp Ile Leu Glu Pro Gly
                85                  90                  95

Thr Met Gln Gly Tyr Asp Arg Asp Pro Arg Ser Ile Ser Lys Arg Ala
            100                 105                 110

Glu Asp Phe Leu Arg Ser Ser Gly Ile Ala Asp Thr Val Leu Phe Gly
        115                 120                 125

Pro Glu Pro Glu Phe Phe Leu Phe Asp Asp Ile Arg Phe Gly Ser Ser

```
                130                 135                 140
Ile Arg Gly Ser His Val Ala Ile Asp Asp Ile Glu Gly Ala Trp Asn
145                 150                 155                 160

Ser Gly Thr Lys Tyr Asp Gly Asn Lys Gly His Arg Pro Ala Val
                165                 170                 175

Lys Gly Gly Tyr Phe Pro Val Pro Val Asp Ser Ser Gln Asp Leu
                180                 185                 190

Arg Ser Thr Met Cys Leu Thr Met Glu Glu Met Gly Leu Val Ile Glu
                195                 200                 205

Ala His His Glu Met Ala Thr Ala Gly Gln Asn Glu Val Ala Thr
210                 215                 220

Arg Phe Asn Thr Met Thr Lys Lys Ala Asp Glu Ile Gln Ile Tyr Lys
225                 230                 235                 240

Tyr Val Val His Asn Val Ala His Ala Phe Gly Lys Thr Ala Thr Phe
                245                 250                 255

Met Pro Lys Pro Met Phe Gly Asp Asn Gly Ser Gly Met His Cys His
                260                 265                 270

Met Ser Leu Ser Lys Asn Gly Thr Asn Leu Phe Ala Gly Asp Lys Tyr
                275                 280                 285

Gly Gly Leu Ser Glu Thr Ala Leu Phe Tyr Ile Gly Ile Ile Lys
                290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Ala Ser Pro
                340                 345                 350

Lys Ala Arg Arg Ile Glu Ala Arg Phe Pro Asp Pro Ala Ala Asn Pro
                355                 360                 365

Tyr Leu Cys Phe Ala Ala Leu Leu Met Ala Gly Leu Asp Gly Ile Ile
                370                 375                 380

Asn Lys Ile His Pro Gly Asp Ala Met Asp Lys Asn Leu Tyr Asp Leu
385                 390                 395                 400

Pro Pro Glu Glu Glu Ala Glu Ile Pro Lys Val Ala Gly Ser Leu Asp
                405                 410                 415

Glu Ala Met Ala Ala Leu Asn Glu Asp Arg Gly Phe Leu Thr Arg Gly
                420                 425                 430

Gly Val Phe Thr Asp Asp Ala Ile Asp Ala Tyr Ile Glu Leu Arg Lys
                435                 440                 445

Glu Glu Met Asp Arg Val Arg Met Thr Pro His Pro Val Glu Phe Glu
450                 455                 460

Leu Tyr Tyr Ser Val
465

<210> SEQ ID NO 25
<211> LENGTH: 1410
<212> TYPE: DNA
<213> ORGANISM: Artificial Sequence
<220> FEATURE:
<223> OTHER INFORMATION: ags1 variant nucleotide sequence (ags1m13)
<221> NAME/KEY: CDS
<222> LOCATION: (1)...(1410)

<400> SEQUENCE: 25 atg tcc gct gaa cac gtt ttg acg atg ctg aat gag cat gaa gtg aaa       48
Met Ser Ala Glu His Val Leu Thr Met Leu Asn Glu His Glu Val Lys
 1               5                  10                  15
```

| | | |
|---|---|---|
| ttc gta gac ctg cgt ttc act gac acc aag ggt aag gaa cag cac gtg<br>Phe Val Asp Leu Arg Phe Thr Asp Thr Lys Gly Lys Glu Gln His Val<br>20 25 30 | 96 | |
| act atc ccg gct cac cag gta aac gcc gac ttc ttc gaa gaa ggt aaa<br>Thr Ile Pro Ala His Gln Val Asn Ala Asp Phe Phe Glu Glu Gly Lys<br>35 40 45 | 144 | |
| atg ttt gac ggc tcc tct atc ggt ggt tgg aag ggc atc aac gaa tct<br>Met Phe Asp Gly Ser Ser Ile Gly Gly Trp Lys Gly Ile Asn Glu Ser<br>50 55 60 | 192 | |
| gac atg gtg ctg atg ccg gac gcc agc acg gcg gtt ctg gat ccg ttc<br>Asp Met Val Leu Met Pro Asp Ala Ser Thr Ala Val Leu Asp Pro Phe<br>65 70 75 80 | 240 | |
| ttc gaa gaa cct acg ctg atc att cgc tgt gac att ctc gag ccg ggc<br>Phe Glu Glu Pro Thr Leu Ile Ile Arg Cys Asp Ile Leu Glu Pro Gly<br>85 90 95 | 288 | |
| acc atg caa ggc tac aat cgc gac ccg cgt tcc atc tcc aaa cgc gcc<br>Thr Met Gln Gly Tyr Asn Arg Asp Pro Arg Ser Ile Ser Lys Arg Ala<br>100 105 110 | 336 | |
| gaa gac ttc ctg cgc tcc tcc ggc atc gcg gac acc atg ctg ttc ggg<br>Glu Asp Phe Leu Arg Ser Ser Gly Ile Ala Asp Thr Met Leu Phe Gly<br>115 120 125 | 384 | |
| cca gag cct gag ttc ttc ctg ttc gac gac atc cgc ttc ggc agc agc<br>Pro Glu Pro Glu Phe Phe Leu Phe Asp Asp Ile Arg Phe Gly Ser Ser<br>130 135 140 | 432 | |
| atc cgc ggt tcc cac gtg gcg atc gac gat atc gaa ggc gcc tgg aac<br>Ile Arg Gly Ser His Val Ala Ile Asp Asp Ile Glu Gly Ala Trp Asn<br>145 150 155 160 | 480 | |
| tcc ggc aca aaa tac gac ggc ggc aac aaa ggc cac cgt ccg gcg gtg<br>Ser Gly Thr Lys Tyr Asp Gly Gly Asn Lys Gly His Arg Pro Ala Val<br>165 170 175 | 528 | |
| aaa ggc ggt tac ttc ccg gtt cca ccg gtc gac tct tcg cag gat ctg<br>Lys Gly Gly Tyr Phe Pro Val Pro Pro Val Asp Ser Ser Gln Asp Leu<br>180 185 190 | 576 | |
| cgt tcc acc atg tgt ctg acc atg gaa gag atg ggc ctg gtg gtt gaa<br>Arg Ser Thr Met Cys Leu Thr Met Glu Glu Met Gly Leu Val Val Glu<br>195 200 205 | 624 | |
| gcg cac cac cac gaa atg gcg acc gcc ggt cag aac gaa gtg gca acc<br>Ala His His His Glu Met Ala Thr Ala Gly Gln Asn Glu Val Ala Thr<br>210 215 220 | 672 | |
| cgc ttc aac acc atg acc aag aaa gcc gac gaa att cag atc tat aag<br>Arg Phe Asn Thr Met Thr Lys Lys Ala Asp Glu Ile Gln Ile Tyr Lys<br>225 230 235 240 | 720 | |
| tac gtg gtg cac aac gtg gcg cac gcc ttc ggt aaa acc gcg acc ttc<br>Tyr Val Val His Asn Val Ala His Ala Phe Gly Lys Thr Ala Thr Phe<br>245 250 255 | 768 | |
| atg ccg aag ccc atg ttc ggc gac aac ggt tcc ggc atg cac tgc cac<br>Met Pro Lys Pro Met Phe Gly Asp Asn Gly Ser Gly Met His Cys His<br>260 265 270 | 816 | |
| atg tcg ctg tcc aag aac ggc acc aac ctg ttc gcc ggc gac aaa tac<br>Met Ser Leu Ser Lys Asn Gly Thr Asn Leu Phe Ala Gly Asp Lys Tyr<br>275 280 285 | 864 | |
| ggc ggc ctg tct gaa acc gca ctg ttc tac atc ggc ggt atc atc aag<br>Gly Gly Leu Ser Glu Thr Ala Leu Phe Tyr Ile Gly Gly Ile Ile Lys<br>290 295 300 | 912 | |
| cac gcc aag gcg atc aac gcg ctg gcc aac ccg acc acc aac tcg tac<br>His Ala Lys Ala Ile Asn Ala Leu Ala Asn Pro Thr Thr Asn Ser Tyr<br>305 310 315 320 | 960 | |
| aaa cgt ctg gtg cca ggc tac gaa gcg ccg gtg atg ctg gct tac tcc<br>Lys Arg Leu Val Pro Gly Tyr Glu Ala Pro Val Met Leu Ala Tyr Ser<br>325 330 335 | 1008 | |

```
gcc cgt aac cgc tcc gcg tcc atc cgt atc ccg gtg gtc gcc agc ccg    1056
Ala Arg Asn Arg Ser Ala Ser Ile Arg Ile Pro Val Val Ala Ser Pro
            340                 345                 350 aaa gcg cgc cgc atc gaa gcc cgc ttc ccg gat ccg gcg gct aac cca    1104
Lys Ala Arg Arg Ile Glu Ala Arg Phe Pro Asp Pro Ala Ala Asn Pro
        355                 360                 365 tac ctg tgc ttc gcc gca ctg ctg atg gcc ggc ctg gac ggc atc atc    1152
Tyr Leu Cys Phe Ala Ala Leu Leu Met Ala Gly Leu Asp Gly Ile Ile
370                 375                 380 aac aag atc cac cct ggc gac gcc atg gac aaa aac ctg tac gac ctg    1200
Asn Lys Ile His Pro Gly Asp Ala Met Asp Lys Asn Leu Tyr Asp Leu
385                 390                 395                 400 ccg ccg gaa gaa gaa gcc gag atc cca aaa gtg gcc ggc tcg ctg gac    1248
Pro Pro Glu Glu Glu Ala Glu Ile Pro Lys Val Ala Gly Ser Leu Asp
                405                 410                 415 gag gcg atg gcc gcg ctg aac gaa gac cgc gag ttc ctg acc cgc ggc    1296
Glu Ala Met Ala Ala Leu Asn Glu Asp Arg Glu Phe Leu Thr Arg Gly
            420                 425                 430 ggc gtg ttc acc gac gat gcg atc gat gcc tac atc gaa ctg cgt aaa    1344
Gly Val Phe Thr Asp Asp Ala Ile Asp Ala Tyr Ile Glu Leu Arg Lys
        435                 440                 445 gaa gag atg gac cgc gtt cgc atg acg cca cac ccg gtc gag ttc gaa    1392
Glu Glu Met Asp Arg Val Arg Met Thr Pro His Pro Val Glu Phe Glu
450                 455                 460 ctg tac tac agc gtc taa                                             1410
Leu Tyr Tyr Ser Val *
465

<210> SEQ ID NO 26
<211> LENGTH: 469
<212> TYPE: PRT
<213> ORGANISM: Artificial Sequence
<220> FEATURE:
<223> OTHER INFORMATION: AGS1 variant amino acid sequence (AGS1M13)

<400> SEQUENCE: 26

Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
            20                  25                  30

Thr Ile Pro Ala His Gln Val Asn Ala Asp Phe Phe Glu Glu Gly Lys
        35                  40                  45

Met Phe Asp Gly Ser Ser Ile Gly Gly Trp Lys Gly Ile Asn Glu Ser
    50                  55                  60

Asp Met Val Leu Met Pro Asp Ala Ser Thr Ala Val Leu Asp Pro Phe
65                  70                  75                  80

Phe Glu Glu Pro Thr Leu Ile Ile Arg Cys Asp Ile Leu Glu Pro Gly
                85                  90                  95

Thr Met Gln Gly Tyr Asn Arg Asp Pro Arg Ser Ile Ser Lys Arg Ala
            100                 105                 110

Glu Asp Phe Leu Arg Ser Ser Gly Ile Ala Asp Thr Met Leu Phe Gly
        115                 120                 125

Pro Glu Pro Glu Phe Phe Leu Phe Asp Asp Ile Arg Phe Gly Ser Ser
    130                 135                 140

Ile Arg Gly Ser His Val Ala Ile Asp Asp Ile Glu Gly Ala Trp Asn
145                 150                 155                 160

Ser Gly Thr Lys Tyr Asp Gly Gly Asn Lys Gly His Arg Pro Ala Val
                165                 170                 175
```

```
Lys Gly Gly Tyr Phe Pro Val Pro Val Asp Ser Ser Gln Asp Leu
            180                 185                 190

Arg Ser Thr Met Cys Leu Thr Met Glu Glu Met Gly Leu Val Val Glu
        195                 200                 205

Ala His His His Glu Met Ala Thr Ala Gly Gln Asn Glu Val Ala Thr
210                 215                 220

Arg Phe Asn Thr Met Thr Lys Lys Ala Asp Glu Ile Gln Ile Tyr Lys
225                 230                 235                 240

Tyr Val Val His Asn Val Ala His Ala Phe Gly Lys Thr Ala Thr Phe
                245                 250                 255

Met Pro Lys Pro Met Phe Gly Asp Asn Gly Ser Gly Met His Cys His
            260                 265                 270

Met Ser Leu Ser Lys Asn Gly Thr Asn Leu Phe Ala Gly Asp Lys Tyr
        275                 280                 285

Gly Gly Leu Ser Glu Thr Ala Leu Phe Tyr Ile Gly Ile Ile Lys
    290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Ala Ser Pro
            340                 345                 350

Lys Ala Arg Arg Ile Glu Ala Arg Phe Pro Asp Pro Ala Ala Asn Pro
        355                 360                 365

Tyr Leu Cys Phe Ala Ala Leu Leu Met Ala Gly Leu Asp Gly Ile Ile
    370                 375                 380

Asn Lys Ile His Pro Gly Asp Ala Met Asp Lys Asn Leu Tyr Asp Leu
385                 390                 395                 400

Pro Pro Glu Glu Glu Ala Glu Ile Pro Lys Val Ala Gly Ser Leu Asp
                405                 410                 415

Glu Ala Met Ala Ala Leu Asn Glu Asp Arg Glu Phe Leu Thr Arg Gly
            420                 425                 430

Gly Val Phe Thr Asp Asp Ala Ile Asp Ala Tyr Ile Glu Leu Arg Lys
        435                 440                 445

Glu Glu Met Asp Arg Val Arg Met Thr Pro His Pro Val Glu Phe Glu
    450                 455                 460

Leu Tyr Tyr Ser Val
465

<210> SEQ ID NO 27
<211> LENGTH: 1410
<212> TYPE: DNA
<213> ORGANISM: Artificial Sequence
<220> FEATURE:
<223> OTHER INFORMATION: ags1 variant nucleotide sequence (ags1m14)
<221> NAME/KEY: CDS
<222> LOCATION: (1)...(1410)

<400> SEQUENCE: 27 atg tcc gct gaa cac gtt ttg acg atg ctg aat gag cat gaa gtg aaa      48
Met Ser Ala Glu His Val Leu Thr Met Leu Asn Glu His Glu Val Lys
 1               5                  10                  15 ttc gta gac ctg cgt ttc act gac acc aag ggt aag gaa cag cac gtg      96
Phe Val Asp Leu Arg Phe Thr Asp Thr Lys Gly Lys Glu Gln His Val
            20                  25                  30 act atc ccg gct cac cag gta aac gcc gac ttc ttc gaa gaa ggt aaa     144
Thr Ile Pro Ala His Gln Val Asn Ala Asp Phe Phe Glu Glu Gly Lys
        35                  40                  45
```

```
atg ttt gac ggc tcc tct atc ggt ggt tgg aag ggc atc aac gaa tct      192
Met Phe Asp Gly Ser Ser Ile Gly Gly Trp Lys Gly Ile Asn Glu Ser
 50              55                  60 gac atg gtg ctg atg ccg gac gcc agc acg gcg gtt ctg gat ccg ttc      240
Asp Met Val Leu Met Pro Asp Ala Ser Thr Ala Val Leu Asp Pro Phe
 65              70                  75                  80 ttc gaa gaa cct acg ctg atc att cgc tgt gac att ctc gag ccg ggc      288
Phe Glu Glu Pro Thr Leu Ile Ile Arg Cys Asp Ile Leu Glu Pro Gly
             85                  90                  95 acc atg caa ggc tac gat cgc gac ccg cgt tcc atc tcc aaa cgc gcc      336
Thr Met Gln Gly Tyr Asp Arg Asp Pro Arg Ser Ile Ser Lys Arg Ala
            100                 105                 110 gaa gac ttc ctg cgc tcc tcc ggc atc gcg gac acc gtg ctg ttc ggg      384
Glu Asp Phe Leu Arg Ser Ser Gly Ile Ala Asp Thr Val Leu Phe Gly
            115                 120                 125 cca gag cct gag ttc ttc ctg ttc gac gac atc cgc ttc ggc agc agc      432
Pro Glu Pro Glu Phe Phe Leu Phe Asp Asp Ile Arg Phe Gly Ser Ser
130                 135                 140 atc cgc ggt tcc cac atg gcg atc gac gat atc gaa ggc gcc tgg aac      480
Ile Arg Gly Ser His Met Ala Ile Asp Asp Ile Glu Gly Ala Trp Asn
145                 150                 155                 160 tcc ggc aca aaa tac aac ggc ggc aac aaa ggc cac cgt ccg gcg gtg      528
Ser Gly Thr Lys Tyr Asn Gly Gly Asn Lys Gly His Arg Pro Ala Val
                165                 170                 175 aaa ggc ggt tac ttc ccg gtt cca ccg gtc gac tct tcg cag gat ctg      576
Lys Gly Gly Tyr Phe Pro Val Pro Pro Val Asp Ser Ser Gln Asp Leu
            180                 185                 190 cgt tcc acc atg tgt ctg acc atg gaa gag atg ggc ctg gtg gtt gaa      624
Arg Ser Thr Met Cys Leu Thr Met Glu Glu Met Gly Leu Val Val Glu
            195                 200                 205 gcg cac cac cac gaa atg gcg acc gcc ggt cag aac gaa gtg gca acc      672
Ala His His His Glu Met Ala Thr Ala Gly Gln Asn Glu Val Ala Thr
210                 215                 220 cgc ttc aac acc atg acc aag aaa gcc gac gaa att cag atc tat aag      720
Arg Phe Asn Thr Met Thr Lys Lys Ala Asp Glu Ile Gln Ile Tyr Lys
225                 230                 235                 240 tac gtg gtg cac aac gtg gcg cac gcc ttc ggt aaa acc gcg acc ttc      768
Tyr Val Val His Asn Val Ala His Ala Phe Gly Lys Thr Ala Thr Phe
                245                 250                 255 atg ccg aag ccc atg ttc ggc gac aac ggt tcc ggc atg cac tgc cac      816
Met Pro Lys Pro Met Phe Gly Asp Asn Gly Ser Gly Met His Cys His
            260                 265                 270 atg tcg ctg tcc aag aac ggc acc aac ctg ttc gcc ggc gac aaa tac      864
Met Ser Leu Ser Lys Asn Gly Thr Asn Leu Phe Ala Gly Asp Lys Tyr
            275                 280                 285 agc ggc ctg tct gaa acc gca ctg ttc tac atc ggc ggt atc atc aag      912
Ser Gly Leu Ser Glu Thr Ala Leu Phe Tyr Ile Gly Gly Ile Ile Lys
            290                 295                 300 cac gcc aag gcg atc aac gcg ctg gcc aac ccg acc acc aac tcg tac      960
His Ala Lys Ala Ile Asn Ala Leu Ala Asn Pro Thr Thr Asn Ser Tyr
305                 310                 315                 320 aaa cgt ctg gtg cca ggc tac gaa gcg ccg gtg atg ctg gct tac tcc     1008
Lys Arg Leu Val Pro Gly Tyr Glu Ala Pro Val Met Leu Ala Tyr Ser
                325                 330                 335 gcc cgt aac cgc tcc gcg tcc atc cgt atc ccg gtg gtc gcc agc ccg     1056
Ala Arg Asn Arg Ser Ala Ser Ile Arg Ile Pro Val Val Ala Ser Pro
            340                 345                 350 aaa gcg cgc cgc atc gaa gcc cgc ttc cct gat ccg gcg gct aac cca     1104
Lys Ala Arg Arg Ile Glu Ala Arg Phe Pro Asp Pro Ala Ala Asn Pro
            355                 360                 365
```

```
tat ctg tgc ttc gcc gca ctg ctg atg gcc ggc ctg gac ggc atc atc      1152
Tyr Leu Cys Phe Ala Ala Leu Leu Met Ala Gly Leu Asp Gly Ile Ile
370                 375                 380 aac aag atc cac cct ggc gac gcc atg gac aaa aac ctg tac gac ctg      1200
Asn Lys Ile His Pro Gly Asp Ala Met Asp Lys Asn Leu Tyr Asp Leu
385                 390                 395                 400 ccg ccg gaa gaa gaa gcc gag atc cca aaa gtg gcc ggc tcg ctg gac      1248
Pro Pro Glu Glu Glu Ala Glu Ile Pro Lys Val Ala Gly Ser Leu Asp
                405                 410                 415 gag gcg atg gtc gcg ctg aac gaa gac cgc gag ttc ctg acc cgc ggc      1296
Glu Ala Met Val Ala Leu Asn Glu Asp Arg Glu Phe Leu Thr Arg Gly
        420                 425                 430 ggc gtg ttc acc gac gat gcg atc gat gcc tac atc gaa ctg cgc aaa      1344
Gly Val Phe Thr Asp Asp Ala Ile Asp Ala Tyr Ile Glu Leu Arg Lys
            435                 440                 445 gaa gag atg gac cgc gtt cgc atg acg cca cac ccg gtc gag ttc gaa      1392
Glu Glu Met Asp Arg Val Arg Met Thr Pro His Pro Val Glu Phe Glu
450                 455                 460 ctg tac tac agc gtc taa                                              1410
Leu Tyr Tyr Ser Val *
465
```

<210> SEQ ID NO 28
<211> LENGTH: 469
<212> TYPE: PRT
<213> ORGANISM: Artificial Sequence
<220> FEATURE:
<223> OTHER INFORMATION: AGS1 variant amino acid sequence (AGS1M14)

<400> SEQUENCE: 28

```
Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
            20                  25                  30

Thr Ile Pro Ala His Gln Val Asn Ala Asp Phe Phe Glu Glu Gly Lys
        35                  40                  45

Met Phe Asp Gly Ser Ser Ile Gly Gly Trp Lys Gly Ile Asn Glu Ser
    50                  55                  60

Asp Met Val Leu Met Pro Asp Ala Ser Thr Ala Val Leu Asp Pro Phe
65                  70                  75                  80

Phe Glu Glu Pro Thr Leu Ile Ile Arg Cys Asp Ile Leu Glu Pro Gly
                85                  90                  95

Thr Met Gln Gly Tyr Asp Arg Asp Pro Arg Ser Ile Ser Lys Arg Ala
            100                 105                 110

Glu Asp Phe Leu Arg Ser Ser Gly Ile Ala Asp Thr Val Leu Phe Gly
        115                 120                 125

Pro Glu Pro Glu Phe Phe Leu Phe Asp Asp Ile Arg Phe Gly Ser Ser
    130                 135                 140

Ile Arg Gly Ser His Met Ala Ile Asp Asp Ile Glu Gly Ala Trp Asn
145                 150                 155                 160

Ser Gly Thr Lys Tyr Asn Gly Gly Asn Lys Gly His Arg Pro Ala Val
                165                 170                 175

Lys Gly Gly Tyr Phe Pro Val Pro Pro Val Asp Ser Ser Gln Asp Leu
            180                 185                 190

Arg Ser Thr Met Cys Leu Thr Met Glu Glu Met Gly Leu Val Val Glu
        195                 200                 205

Ala His His His Glu Met Ala Thr Ala Gly Gln Asn Glu Val Ala Thr
    210                 215                 220
```

-continued

```
Arg Phe Asn Thr Met Thr Lys Lys Ala Asp Glu Ile Gln Ile Tyr Lys
225                 230                 235                 240

Tyr Val Val His Asn Val Ala His Ala Phe Gly Lys Thr Ala Thr Phe
            245                 250                 255

Met Pro Lys Pro Met Phe Gly Asp Asn Gly Ser Gly Met His Cys His
        260                 265                 270

Met Ser Leu Ser Lys Asn Gly Thr Asn Leu Phe Ala Gly Asp Lys Tyr
    275                 280                 285

Ser Gly Leu Ser Glu Thr Ala Leu Phe Tyr Ile Gly Ile Ile Lys
290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
            325                 330                 335

Ala Arg Asn Arg Ser Ala Ser Ile Arg Ile Pro Val Val Ala Ser Pro
        340                 345                 350

Lys Ala Arg Arg Ile Glu Ala Arg Phe Pro Asp Pro Ala Ala Asn Pro
    355                 360                 365

Tyr Leu Cys Phe Ala Ala Leu Leu Met Ala Gly Leu Asp Gly Ile Ile
370                 375                 380

Asn Lys Ile His Pro Gly Asp Ala Met Asp Lys Asn Leu Tyr Asp Leu
385                 390                 395                 400

Pro Pro Glu Glu Glu Ala Glu Ile Pro Lys Val Ala Gly Ser Leu Asp
            405                 410                 415

Glu Ala Met Val Ala Leu Asn Glu Asp Arg Glu Phe Leu Thr Arg Gly
        420                 425                 430

Gly Val Phe Thr Asp Asp Ala Ile Asp Ala Tyr Ile Glu Leu Arg Lys
    435                 440                 445

Glu Glu Met Asp Arg Val Arg Met Thr Pro His Pro Val Glu Phe Glu
450                 455                 460

Leu Tyr Tyr Ser Val
465

<210> SEQ ID NO 29
<211> LENGTH: 1410
<212> TYPE: DNA
<213> ORGANISM: Artificial Sequence
<220> FEATURE:
<223> OTHER INFORMATION: ags1 variant nucleotide sequence (ags1m15)
<221> NAME/KEY: CDS
<222> LOCATION: (1)...(1410)

<400> SEQUENCE: 29 atg tcc gct gaa cac gtt ttg acg atg ctg aat gag cat gaa gtg aaa      48
Met Ser Ala Glu His Val Leu Thr Met Leu Asn Glu His Glu Val Lys
1               5                   10                  15 ttc gta gac ctg cgt ttc act gac acc aag ggt aag gaa cag cac gtg     96
Phe Val Asp Leu Arg Phe Thr Asp Thr Lys Gly Lys Glu Gln His Val
                20                  25                  30 act atc ccg gct cac cag gta aac gcc gac ttc ttc gaa gaa ggt aaa    144
Thr Ile Pro Ala His Gln Val Asn Ala Asp Phe Phe Glu Glu Gly Lys
            35                  40                  45 atg ttt gac ggc tcc gct atc ggt ggt tgg aag ggc atc aac gaa tct    192
Met Phe Asp Gly Ser Ala Ile Gly Gly Trp Lys Gly Ile Asn Glu Ser
        50                  55                  60 gac atg gtg ctg atg ccg gac gcc agc acg gcg gtt ctg gat ccg ttc    240
Asp Met Val Leu Met Pro Asp Ala Ser Thr Ala Val Leu Asp Pro Phe
65                  70                  75                  80
```

| | | | | | | | | | | | | | | | | |
|---|---|---|---|---|---|---|---|---|---|---|---|---|---|---|---|---|
| ttc | gaa | gaa | cct | acg | ctg | atc | att | cgc | tgt | gac | att | ctc | gag | ccg | ggc | 288 |
| Phe | Glu | Glu | Pro | Thr 85 | Leu | Ile | Ile | Arg | Cys 90 | Asp | Ile | Leu | Glu | Pro 95 | Gly | |
| acc | atg | caa | ggc | tac | gat | cgc | gac | ccg | cgt | tcc | atc | tcc | aaa | cgc | gcc | 336 |
| Thr | Met | Gln | Gly 100 | Tyr | Asp | Arg | Asp | Pro 105 | Arg | Ser | Ile | Ser | Lys 110 | Arg | Ala | |
| gaa | gat | ttc | ctg | cgc | tcc | tcc | ggc | atc | gcg | gac | acc | gtg | ctg | ttc | ggg | 384 |
| Glu | Asp | Phe | Leu 115 | Arg | Ser | Ser | Gly | Ile 120 | Ala | Asp | Thr | Val | Leu 125 | Phe | Gly | |
| cca | gag | cct | gag | ttc | ttc | ctg | ttc | gac | gac | atc | cgc | ttc | ggc | agc | agc | 432 |
| Pro | Glu 130 | Pro | Glu | Phe | Phe | Leu 135 | Phe | Asp | Asp | Ile | Arg 140 | Phe | Gly | Ser | Ser | |
| atc | cgc | ggt | tcc | cac | gta | gcg | atc | gac | gat | atc | gaa | ggc | gcc | tgg | aac | 480 |
| Ile 145 | Arg | Gly | Ser | His | Val 150 | Ala | Ile | Asp | Asp | Ile 155 | Glu | Gly | Ala | Trp | Asn 160 | |
| tcc | ggc | aca | aaa | tac | gac | ggc | ggc | aac | aaa | ggc | cac | gtc | ccg | gcg | gtg | 528 |
| Ser | Gly | Thr | Lys | Tyr 165 | Asp | Gly | Gly | Asn | Lys 170 | Gly | His | Arg | Pro | Ala 175 | Val | |
| aaa | ggc | ggt | tac | ttc | ccg | gtt | cca | ccg | gtc | gac | tct | tcg | cag | gat | ctg | 576 |
| Lys | Gly | Gly | Tyr 180 | Phe | Pro | Val | Pro | Pro 185 | Val | Asp | Ser | Ser | Gln 190 | Asp | Leu | |
| cgt | tcc | acc | atg | tgt | ctg | acc | atg | gaa | gag | atg | ggc | ctg | gtg | gtt | gaa | 624 |
| Arg | Ser | Thr | Met | Cys 195 | Leu | Thr | Met | Glu | Glu 200 | Met | Gly | Leu | Val | Val 205 | Glu | |
| gca | cac | cac | cac | gaa | gtg | gcg | acc | gcc | ggt | cag | aac | gaa | gtg | gca | acc | 672 |
| Ala | His 210 | His | His | Glu | Val | Ala 215 | Thr | Ala | Gly | Gln | Asn 220 | Glu | Val | Ala | Thr | |
| cgc | ttc | aac | acc | atg | acc | aag | aaa | gcc | gac | gaa | att | cag | atc | tat | aag | 720 |
| Arg 225 | Phe | Asn | Thr | Met | Thr 230 | Lys | Lys | Ala | Asp | Glu 235 | Ile | Gln | Ile | Tyr | Lys 240 | |
| tac | gtg | gtg | cac | aac | gtg | gcg | cac | gcc | ttc | ggt | aaa | acc | gcg | acc | ttc | 768 |
| Tyr | Val | Val | His | Asn 245 | Val | Ala | His | Ala | Phe 250 | Gly | Lys | Thr | Ala | Thr 255 | Phe | |
| atg | ccg | aag | ccc | atg | ttc | ggc | gac | aac | ggt | tcc | ggc | atg | cac | tgc | cac | 816 |
| Met | Pro | Lys | Pro 260 | Met | Phe | Gly | Asp | Asn 265 | Gly | Ser | Gly | Met | His 270 | Cys | His | |
| atg | tcg | ctg | tcc | aag | aac | ggc | acc | aac | ctg | ttc | gcc | ggc | gac | aaa | tac | 864 |
| Met | Ser | Leu 275 | Ser | Lys | Asn | Gly | Thr 280 | Asn | Leu | Phe | Ala | Gly 285 | Asp | Lys | Tyr | |
| ggc | ggc | ctg | tct | gaa | acc | gca | ctg | ttc | tac | atc | ggc | ggt | atc | atc | aag | 912 |
| Gly | Gly 290 | Leu | Ser | Glu | Thr | Ala 295 | Leu | Phe | Tyr | Ile | Gly 300 | Gly | Ile | Ile | Lys | |
| cac | gcc | aag | gcg | atc | aac | gcg | ctg | gcc | aac | ccg | acc | acc | aac | tcg | tac | 960 |
| His 305 | Ala | Lys | Ala | Ile | Asn 310 | Ala | Leu | Ala | Asn | Pro 315 | Thr | Thr | Asn | Ser | Tyr 320 | |
| aaa | cgt | ctg | gtg | cca | ggc | tac | gaa | gcg | ccg | gtg | atg | ctg | gct | tac | tcc | 1008 |
| Lys | Arg | Leu | Val | Pro 325 | Gly | Tyr | Glu | Ala | Pro 330 | Val | Met | Leu | Ala | Tyr 335 | Ser | |
| gcc | cgt | aac | cgc | tcc | gcg | tcc | atc | cgt | atc | ccg | gtg | gtc | gcc | agc | ccg | 1056 |
| Ala | Arg | Asn | Arg 340 | Ser | Ala | Ser | Ile | Arg 345 | Ile | Pro | Val | Val | Ala 350 | Ser | Pro | |
| aaa | gcg | cgc | cgc | atc | gaa | gcc | cgc | ttc | ccg | gat | ccg | gcg | gct | aac | cca | 1104 |
| Lys | Ala | Arg | Arg | Ile 355 | Glu | Ala | Arg | Phe | Pro 360 | Asp | Pro | Ala | Ala | Asn 365 | Pro | |
| tac | ctg | tgc | ttc | gcc | gca | ctg | cta | atg | gcc | ggc | ctg | gac | ggc | atc | atc | 1152 |
| Tyr | Leu | Cys | Phe 370 | Ala | Ala | Leu | Leu | Met 375 | Ala | Gly | Leu | Asp | Gly 380 | Ile | Ile | |
| aac | aag | atc | cac | cct | ggc | gac | gcc | atg | gac | aaa | aac | ctg | tac | gac | ctg | 1200 |
| Asn | Lys | Ile | His | Pro 385 | Gly | Asp | Ala | Met | Asp 390 | Lys | Asn | Leu | Tyr | Asp 395 | Leu 400 | |

-continued

```
ccg ccg gaa gaa gaa gcc gag atc cca aaa gtg gcc ggc tcg ctg gac      1248
Pro Pro Glu Glu Glu Ala Glu Ile Pro Lys Val Ala Gly Ser Leu Asp
            405                 410                 415 gag gcg atg gcc gcg ctg aac gaa gac cgc gag ttc ctg acc cgc ggc      1296
Glu Ala Met Ala Ala Leu Asn Glu Asp Arg Glu Phe Leu Thr Arg Gly
        420                 425                 430 ggc gtg ttc acc gac gat gcg atc gat gcc tac atc gaa ctg cgc aaa     1344
Gly Val Phe Thr Asp Asp Ala Ile Asp Ala Tyr Ile Glu Leu Arg Lys
    435                 440                 445 gaa gag atg gac cgc gtt cgc atg acg cca cac ccg gtc gag ttc gaa     1392
Glu Glu Met Asp Arg Val Arg Met Thr Pro His Pro Val Glu Phe Glu
450                 455                 460 ctg tac tac agc gtc taa                                              1410
Leu Tyr Tyr Ser Val *
465
```

<210> SEQ ID NO 30
<211> LENGTH: 469
<212> TYPE: PRT
<213> ORGANISM: Artificial Sequence
<220> FEATURE:
<223> OTHER INFORMATION: AGS1 variant amino acid sequence (AGS1M15)

<400> SEQUENCE: 30

```
Met Ser Ala Glu His Val Leu Thr Met Leu Asn Glu His Glu Val Lys
 1               5                  10                  15

Phe Val Asp Leu Arg Phe Thr Asp Thr Lys Gly Lys Glu Gln His Val
            20                  25                  30

Thr Ile Pro Ala His Gln Val Asn Ala Asp Phe Phe Glu Glu Gly Lys
        35                  40                  45

Met Phe Asp Gly Ser Ala Ile Gly Gly Trp Lys Gly Ile Asn Glu Ser
    50                  55                  60

Asp Met Val Leu Met Pro Asp Ala Ser Thr Ala Val Leu Asp Pro Phe
65                  70                  75                  80

Phe Glu Glu Pro Thr Leu Ile Ile Arg Cys Asp Ile Leu Glu Pro Gly
                85                  90                  95

Thr Met Gln Gly Tyr Asp Arg Asp Pro Arg Ser Ile Ser Lys Arg Ala
            100                 105                 110

Glu Asp Phe Leu Arg Ser Ser Gly Ile Ala Asp Thr Val Leu Phe Gly
        115                 120                 125

Pro Glu Pro Glu Phe Phe Leu Phe Asp Asp Ile Arg Phe Gly Ser Ser
    130                 135                 140

Ile Arg Gly Ser His Val Ala Ile Asp Asp Ile Glu Gly Ala Trp Asn
145                 150                 155                 160

Ser Gly Thr Lys Tyr Asp Gly Gly Asn Lys Gly His Arg Pro Ala Val
                165                 170                 175

Lys Gly Gly Tyr Phe Pro Val Pro Pro Val Asp Ser Ser Gln Asp Leu
            180                 185                 190

Arg Ser Thr Met Cys Leu Thr Met Glu Glu Met Gly Leu Val Val Glu
        195                 200                 205

Ala His His His Glu Val Ala Thr Ala Gly Gln Asn Glu Val Ala Thr
    210                 215                 220

Arg Phe Asn Thr Met Thr Lys Lys Ala Asp Glu Ile Gln Ile Tyr Lys
225                 230                 235                 240

Tyr Val Val His Asn Val Ala His Ala Phe Gly Lys Thr Ala Thr Phe
                245                 250                 255

Met Pro Lys Pro Met Phe Gly Asp Asn Gly Ser Gly Met His Cys His
```

```
                       260                 265                 270
Met Ser Leu Ser Lys Asn Gly Thr Asn Leu Phe Ala Gly Asp Lys Tyr
            275                 280                 285

Gly Gly Leu Ser Glu Thr Ala Leu Phe Tyr Ile Gly Ile Ile Lys
        290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Ala Ser Pro
            340                 345                 350

Lys Ala Arg Arg Ile Glu Ala Arg Phe Pro Asp Pro Ala Ala Asn Pro
        355                 360                 365

Tyr Leu Cys Phe Ala Ala Leu Leu Met Ala Gly Leu Asp Gly Ile Ile
    370                 375                 380

Asn Lys Ile His Pro Gly Asp Ala Met Asp Lys Asn Leu Tyr Asp Leu
385                 390                 395                 400

Pro Pro Glu Glu Ala Glu Ile Pro Lys Val Ala Gly Ser Leu Asp
                405                 410                 415

Glu Ala Met Ala Ala Leu Asn Glu Asp Arg Glu Phe Leu Thr Arg Gly
            420                 425                 430

Gly Val Phe Thr Asp Asp Ala Ile Asp Ala Tyr Ile Glu Leu Arg Lys
        435                 440                 445

Glu Glu Met Asp Arg Val Arg Met Thr Pro His Pro Val Glu Phe Glu
    450                 455                 460

Leu Tyr Tyr Ser Val
465

<210> SEQ ID NO 31
<211> LENGTH: 1410
<212> TYPE: DNA
<213> ORGANISM: Artificial Sequence
<220> FEATURE:
<223> OTHER INFORMATION: ags1 variant nucleotide sequence (ags1m16)
<221> NAME/KEY: CDS
<222> LOCATION: (1)...(1410)

<400> SEQUENCE: 31 atg tcc gct gaa cac gtt ttg acg atg ctg aat gag cat gaa gtg aaa      48
Met Ser Ala Glu His Val Leu Thr Met Leu Asn Glu His Glu Val Lys
1               5                   10                  15 ttc gta gac ctg cgt ttc act gac acc aag ggt aag gaa cag cac gtg      96
Phe Val Asp Leu Arg Phe Thr Asp Thr Lys Gly Lys Glu Gln His Val
            20                  25                  30 act atc ccg gct cac cag gta aac gcc gac ttc ttc gaa gaa ggt aaa     144
Thr Ile Pro Ala His Gln Val Asn Ala Asp Phe Phe Glu Glu Gly Lys
        35                  40                  45 atg ttt gac ggc tcc tct atc ggt ggt tgg aag ggc atc aac gaa tct     192
Met Phe Asp Gly Ser Ser Ile Gly Gly Trp Lys Gly Ile Asn Glu Ser
    50                  55                  60 gac atg gtg ctg atg ccg gac gcc agc acg gcg gtt ctg gat ccg ttc     240
Asp Met Val Leu Met Pro Asp Ala Ser Thr Ala Val Leu Asp Pro Phe
65                  70                  75                  80 tcc gaa gaa cct acg ctg atc att cgc tgt gac att ctc gag ccg ggc     288
Ser Glu Glu Pro Thr Leu Ile Ile Arg Cys Asp Ile Leu Glu Pro Gly
                85                  90                  95 acc atg caa ggc tac gat cgc gac ccg cgt tcc atc tcc aaa cgc gcc     336
Thr Met Gln Gly Tyr Asp Arg Asp Pro Arg Ser Ile Ser Lys Arg Ala
            100                 105                 110
```

```
gaa gac ttc ctg cgc tcc tcc ggc atc gcg gac acc gtg ctg ttc ggg      384
Glu Asp Phe Leu Arg Ser Ser Gly Ile Ala Asp Thr Val Leu Phe Gly
        115                 120                 125 cca gag cct gag ttc ttc ctg ttc gac gac atc cgc ttc ggc agc agc      432
Pro Glu Pro Glu Phe Phe Leu Phe Asp Asp Ile Arg Phe Gly Ser Ser
130                 135                 140 atc cgc ggt tcc cac gtg gcg atc gac gat atc gaa ggc gcg tgg aac      480
Ile Arg Gly Ser His Val Ala Ile Asp Asp Ile Glu Gly Ala Trp Asn
145                 150                 155                 160 tcc ggc aca aaa tac gac ggc ggc aac aaa ggc cac cgt ccg gcg gtg      528
Ser Gly Thr Lys Tyr Asp Gly Gly Asn Lys Gly His Arg Pro Ala Val
        165                 170                 175 aaa ggc ggt tac ttc ccg gtt cca tcg gtc gac tct tcg cag gat ctg      576
Lys Gly Gly Tyr Phe Pro Val Pro Ser Val Asp Ser Ser Gln Asp Leu
        180                 185                 190 cgt tcc acc atg tgt ctg acc atg gaa gag atg ggc ctg gtg gtt gaa      624
Arg Ser Thr Met Cys Leu Thr Met Glu Glu Met Gly Leu Val Val Glu
        195                 200                 205 gcg cac cac aac gaa gtg gcg acc gcc agt cag aac gaa gtg gca acc      672
Ala His His Asn Glu Val Ala Thr Ala Ser Gln Asn Glu Val Ala Thr
        210                 215                 220 cgc ttc aac acc atg acc aag aaa gcc gac gaa att cag atc tat aag      720
Arg Phe Asn Thr Met Thr Lys Lys Ala Asp Glu Ile Gln Ile Tyr Lys
225                 230                 235                 240 tac gtg gtg cac aac gtg gca cac gcc ttc ggt aaa acc gcg acc ttc      768
Tyr Val Val His Asn Val Ala His Ala Phe Gly Lys Thr Ala Thr Phe
        245                 250                 255 atg ccg aag ccc atg ttc ggc gac aac ggt tcc ggc atg cac tgc cac      816
Met Pro Lys Pro Met Phe Gly Asp Asn Gly Ser Gly Met His Cys His
        260                 265                 270 atg tcg ctg tcc aag aac ggc acc aac ctg ttc gcc ggc gac aaa tac      864
Met Ser Leu Ser Lys Asn Gly Thr Asn Leu Phe Ala Gly Asp Lys Tyr
        275                 280                 285 ggc ggc ctg tct gaa acc gca ctg ttc tac atc ggc ggt atc aac aag      912
Gly Gly Leu Ser Glu Thr Ala Leu Phe Tyr Ile Gly Gly Ile Asn Lys
        290                 295                 300 cac gcc aag gcg atc aac gcg ctg gcc aac ccg acc acc aac tcg tac      960
His Ala Lys Ala Ile Asn Ala Leu Ala Asn Pro Thr Thr Asn Ser Tyr
305                 310                 315                 320 aaa cgt ctg gtg cca ggc tac gaa gcg ccg gtg atg ctg gct tac tcc     1008
Lys Arg Leu Val Pro Gly Tyr Glu Ala Pro Val Met Leu Ala Tyr Ser
        325                 330                 335 gcc cgt aac cgc tcc gcg tcc atc cgt atc ccg gtg gtc gcc agc ccg     1056
Ala Arg Asn Arg Ser Ala Ser Ile Arg Ile Pro Val Val Ala Ser Pro
        340                 345                 350 aaa gcg cgc cgc atc gaa gcc cgc ttc ccg gat ccg gcg gct aac cca     1104
Lys Ala Arg Arg Ile Glu Ala Arg Phe Pro Asp Pro Ala Ala Asn Pro
        355                 360                 365 tac ctg tgc ttc gcc gca ctg ctg atg gcc ggc ctg gac ggc atc atc     1152
Tyr Leu Cys Phe Ala Ala Leu Leu Met Ala Gly Leu Asp Gly Ile Ile
        370                 375                 380 aac aag atc cac cct ggc gac gcc atg gac aaa aac ctg tac gac ctg     1200
Asn Lys Ile His Pro Gly Asp Ala Met Asp Lys Asn Leu Tyr Asp Leu
385                 390                 395                 400 ccg ccg gaa gaa gaa gcc gag atc cca aaa gtg gcc ggc tcg ctg gac     1248
Pro Pro Glu Glu Glu Ala Glu Ile Pro Lys Val Ala Gly Ser Leu Asp
        405                 410                 415 gag gcg atg gcc gcg ctg aac gaa gac cgc gag ttc ctg acc cgc ggc     1296
Glu Ala Met Ala Ala Leu Asn Glu Asp Arg Glu Phe Leu Thr Arg Gly
        420                 425                 430
```

-continued

```
ggc gtg ttc act gac gat gcg atc gat gcc tac atc gaa ctg cgc aaa    1344
Gly Val Phe Thr Asp Asp Ala Ile Asp Ala Tyr Ile Glu Leu Arg Lys
        435                 440                 445 gaa gag atg gac cgc gtt cgc atg acg cca cac ccg gtc gag ttc gaa    1392
Glu Glu Met Asp Arg Val Arg Met Thr Pro His Pro Val Glu Phe Glu
    450                 455                 460 ctg tac tac agc gtc taa                                            1410
Leu Tyr Tyr Ser Val *
465

<210> SEQ ID NO 32
<211> LENGTH: 469
<212> TYPE: PRT
<213> ORGANISM: Artificial Sequence
<220> FEATURE:
<223> OTHER INFORMATION: AGS1 variant amino acid sequence (AGS1M16)

<400> SEQUENCE: 32

Met Ser Ala Glu His Val Leu Thr Met Leu Asn Glu His Glu Val Lys
 1               5                  10                  15

Phe Val Asp Leu Arg Phe Thr Asp Thr Lys Gly Lys Glu Gln His Val
            20                  25                  30

Thr Ile Pro Ala His Gln Val Asn Ala Asp Phe Phe Glu Glu Gly Lys
        35                  40                  45

Met Phe Asp Gly Ser Ser Ile Gly Gly Trp Lys Gly Ile Asn Glu Ser
    50                  55                  60

Asp Met Val Leu Met Pro Asp Ala Ser Thr Ala Val Leu Asp Pro Phe
65                  70                  75                  80

Ser Glu Glu Pro Thr Leu Ile Ile Arg Cys Asp Ile Leu Glu Pro Gly
                85                  90                  95

Thr Met Gln Gly Tyr Asp Arg Asp Pro Arg Ser Ile Ser Lys Arg Ala
            100                 105                 110

Glu Asp Phe Leu Arg Ser Ser Gly Ile Ala Asp Thr Val Leu Phe Gly
        115                 120                 125

Pro Glu Pro Glu Phe Phe Leu Phe Asp Asp Ile Arg Phe Gly Ser Ser
    130                 135                 140

Ile Arg Gly Ser His Val Ala Ile Asp Asp Ile Glu Gly Ala Trp Asn
145                 150                 155                 160

Ser Gly Thr Lys Tyr Asp Gly Gly Asn Lys Gly His Arg Pro Ala Val
                165                 170                 175

Lys Gly Gly Tyr Phe Pro Val Pro Ser Val Asp Ser Ser Gln Asp Leu
            180                 185                 190

Arg Ser Thr Met Cys Leu Thr Met Glu Glu Met Gly Leu Val Val Glu
        195                 200                 205

Ala His His Asn Glu Val Ala Thr Ala Ser Gln Asn Glu Val Ala Thr
    210                 215                 220

Arg Phe Asn Thr Met Thr Lys Lys Ala Asp Glu Ile Gln Ile Tyr Lys
225                 230                 235                 240

Tyr Val Val His Asn Val Ala His Ala Phe Gly Lys Thr Ala Thr Phe
                245                 250                 255

Met Pro Lys Pro Met Phe Gly Asp Asn Gly Ser Gly Met His Cys His
            260                 265                 270

Met Ser Leu Ser Lys Asn Gly Thr Asn Leu Phe Ala Gly Asp Lys Tyr
        275                 280                 285

Gly Gly Leu Ser Glu Thr Ala Leu Phe Tyr Ile Gly Gly Ile Asn Lys
    290                 295                 300
```

```
His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Ala Ser Pro
            340                 345                 350

Lys Ala Arg Arg Ile Glu Ala Arg Phe Pro Asp Pro Ala Ala Asn Pro
        355                 360                 365

Tyr Leu Cys Phe Ala Ala Leu Leu Met Ala Gly Leu Asp Gly Ile Ile
    370                 375                 380

Asn Lys Ile His Pro Gly Asp Ala Met Asp Lys Asn Leu Tyr Asp Leu
385                 390                 395                 400

Pro Pro Glu Glu Glu Ala Glu Ile Pro Lys Val Ala Gly Ser Leu Asp
                405                 410                 415

Glu Ala Met Ala Ala Leu Asn Glu Asp Arg Glu Phe Leu Thr Arg Gly
            420                 425                 430

Gly Val Phe Thr Asp Asp Ala Ile Asp Ala Tyr Ile Glu Leu Arg Lys
        435                 440                 445

Glu Glu Met Asp Arg Val Arg Met Thr Pro His Pro Val Glu Phe Glu
450                 455                 460

Leu Tyr Tyr Ser Val
465

<210> SEQ ID NO 33
<211> LENGTH: 1410
<212> TYPE: DNA
<213> ORGANISM: Artificial Sequence
<220> FEATURE:
<223> OTHER INFORMATION: ags1 variant nucleotide sequence (ags1m17)
<221> NAME/KEY: CDS
<222> LOCATION: (1)...(1410)

<400> SEQUENCE: 33 atg tcc gct gaa cac gtt ttg acg atg ctg aat gag cat gaa gtg aaa       48
Met Ser Ala Glu His Val Leu Thr Met Leu Asn Glu His Glu Val Lys
1               5                   10                  15 ttc gta gac ctg cgt ttc act gac acc aag ggt aag gaa cag cac gtg       96
Phe Val Asp Leu Arg Phe Thr Asp Thr Lys Gly Lys Glu Gln His Val
                20                  25                  30 act atc ccg gct cac cag gta aac gcc gac ttc ttc gaa gaa ggt aaa      144
Thr Ile Pro Ala His Gln Val Asn Ala Asp Phe Phe Glu Glu Gly Lys
            35                  40                  45 atg ttt gac ggc tcc tct atc ggt ggt tgg aag ggc atc aac gaa tct      192
Met Phe Asp Gly Ser Ser Ile Gly Gly Trp Lys Gly Ile Asn Glu Ser
        50                  55                  60 gac atg gtg ctg atg ccg gac gcc agc acg gcg gtt ctg gat ccg ttc      240
Asp Met Val Leu Met Pro Asp Ala Ser Thr Ala Val Leu Asp Pro Phe
65                  70                  75                  80 tcc gaa gaa cct acg ctg atc att cgc tgt gac att ctc gag ccg ggc      288
Ser Glu Glu Pro Thr Leu Ile Ile Arg Cys Asp Ile Leu Glu Pro Gly
                85                  90                  95 acc atg caa ggc tac gat cgc gac ccg cgt tcc atc tcc aaa cgc gcc      336
Thr Met Gln Gly Tyr Asp Arg Asp Pro Arg Ser Ile Ser Lys Arg Ala
            100                 105                 110 gaa gac ttc ctg cgc tcc tcc ggc atc gcg gac acc gtg ctg ttc ggg      384
Glu Asp Phe Leu Arg Ser Ser Gly Ile Ala Asp Thr Val Leu Phe Gly
        115                 120                 125 cca gag cct gag ttc ttc ctg ttc gac gac atc cgc ttc ggc agc agc      432
Pro Glu Pro Glu Phe Phe Leu Phe Asp Asp Ile Arg Phe Gly Ser Ser
    130                 135                 140
```

```
atc cgc ggt tcc cac gtg gcg atc gac gat atc gaa ggc gcc tgg aac      480
Ile Arg Gly Ser His Val Ala Ile Asp Asp Ile Glu Gly Ala Trp Asn
145                 150                 155                 160 tcc ggc aca aaa tac gac ggc ggc aac aaa ggc cac cgt ccg gcg gtg      528
Ser Gly Thr Lys Tyr Asp Gly Gly Asn Lys Gly His Arg Pro Ala Val
                165                 170                 175 aaa ggc ggt tac ttc ccg gtt cca tcg gtc gac tct tcg cag gat ctg      576
Lys Gly Gly Tyr Phe Pro Val Pro Ser Val Asp Ser Ser Gln Asp Leu
            180                 185                 190 cgt tcc acc atg tgt ctg acc atg gaa gag atg ggc ctg gtg gtt gaa      624
Arg Ser Thr Met Cys Leu Thr Met Glu Glu Met Gly Leu Val Val Glu
        195                 200                 205 gcg cac cac acc gag gca gcg acc gct agc cag aac gaa gtg gca acc      672
Ala His His Thr Glu Ala Ala Thr Ala Ser Gln Asn Glu Val Ala Thr
    210                 215                 220 cgc ttc aac acc atg acc aag aaa gcc gac gaa att cag atc tat aag      720
Arg Phe Asn Thr Met Thr Lys Lys Ala Asp Glu Ile Gln Ile Tyr Lys
225                 230                 235                 240 tac gtg gtg cac aac gtg gca cac gcc ttc ggt aaa acc gcg acc ttc      768
Tyr Val Val His Asn Val Ala His Ala Phe Gly Lys Thr Ala Thr Phe
                245                 250                 255 atg ccg aag ccc atg ttc ggc gac aac ggt tcc ggc atg cac tgc cac      816
Met Pro Lys Pro Met Phe Gly Asp Asn Gly Ser Gly Met His Cys His
            260                 265                 270 atg tcg ctg tcc aag aac ggc acc aac ctg ttc gcc ggc gac aaa tac      864
Met Ser Leu Ser Lys Asn Gly Thr Asn Leu Phe Ala Gly Asp Lys Tyr
        275                 280                 285 ggc ggc ctg tct gaa acc gca ctg ttc tac atc ggc ggt atc aac aag      912
Gly Gly Leu Ser Glu Thr Ala Leu Phe Tyr Ile Gly Gly Ile Asn Lys
    290                 295                 300 cac gcc aag gcg atc aac gcg ctg gcc aac ccg acc acc aac tcg tac      960
His Ala Lys Ala Ile Asn Ala Leu Ala Asn Pro Thr Thr Asn Ser Tyr
305                 310                 315                 320 aaa cgt ctg gtg cca ggc tac gaa gcg ccg gtg atg ctg gct tac tcc     1008
Lys Arg Leu Val Pro Gly Tyr Glu Ala Pro Val Met Leu Ala Tyr Ser
                325                 330                 335 gcc cgt aac cgc tcc gcg tcc atc cgt atc ccg gtg gtc gcc agc ccg     1056
Ala Arg Asn Arg Ser Ala Ser Ile Arg Ile Pro Val Val Ala Ser Pro
            340                 345                 350 aaa gcg cgc cgc atc gaa gcc cgc ttc ccg gat ccg gcg gct aac cca     1104
Lys Ala Arg Arg Ile Glu Ala Arg Phe Pro Asp Pro Ala Ala Asn Pro
        355                 360                 365 tac ctg tgc ttc gcc gca ctg ctg atg gcc ggc ctg gac ggc atc atc     1152
Tyr Leu Cys Phe Ala Ala Leu Leu Met Ala Gly Leu Asp Gly Ile Ile
    370                 375                 380 aac aag atc cac cct ggc gac gcc atg gac aaa aac ctg tac gac ctg     1200
Asn Lys Ile His Pro Gly Asp Ala Met Asp Lys Asn Leu Tyr Asp Leu
385                 390                 395                 400 ccg ccg gaa gaa gaa gcc gag atc cca aaa gtg gcc ggc tcg ctg gac     1248
Pro Pro Glu Glu Glu Ala Glu Ile Pro Lys Val Ala Gly Ser Leu Asp
                405                 410                 415 gag gcg atg gcc gcg ctg aac gaa gac cgc gag ttc ctg acc cgc ggc     1296
Glu Ala Met Ala Ala Leu Asn Glu Asp Arg Glu Phe Leu Thr Arg Gly
            420                 425                 430 ggc gtg ttc act gac gat gcg atc gat gcc tac atc gaa ctg cgc aaa     1344
Gly Val Phe Thr Asp Asp Ala Ile Asp Ala Tyr Ile Glu Leu Arg Lys
        435                 440                 445 gaa gag atg gac cgc gtt cgc atg acg cca cac ccg gtc gag ttc gaa     1392
Glu Glu Met Asp Arg Val Arg Met Thr Pro His Pro Val Glu Phe Glu
    450                 455                 460
```

```
ctg tac tac agc gtc taa                                          1410
Leu Tyr Tyr Ser Val *
465
```

<210> SEQ ID NO 34
<211> LENGTH: 469
<212> TYPE: PRT
<213> ORGANISM: Artificial Sequence
<220> FEATURE:
<223> OTHER INFORMATION: AGS1 variant amino acid sequence (AGS1M17)

<400> SEQUENCE: 34

```
Met Ser Ala Glu His Val Leu Thr Met Leu Asn Glu His Glu Val Lys
 1               5                  10                  15

Phe Val Asp Leu Arg Phe Thr Asp Thr Lys Gly Lys Glu Gln His Val
            20                  25                  30

Thr Ile Pro Ala His Gln Val Asn Ala Asp Phe Phe Glu Glu Gly Lys
        35                  40                  45

Met Phe Asp Gly Ser Ser Ile Gly Gly Trp Lys Gly Ile Asn Glu Ser
 50                  55                  60

Asp Met Val Leu Met Pro Asp Ala Ser Thr Ala Val Leu Asp Pro Phe
65                  70                  75                  80

Ser Glu Glu Pro Thr Leu Ile Ile Arg Cys Asp Ile Leu Glu Pro Gly
                85                  90                  95

Thr Met Gln Gly Tyr Asp Arg Asp Pro Arg Ser Ile Ser Lys Arg Ala
            100                 105                 110

Glu Asp Phe Leu Arg Ser Ser Gly Ile Ala Asp Thr Val Leu Phe Gly
        115                 120                 125

Pro Glu Pro Glu Phe Phe Leu Phe Asp Asp Ile Arg Phe Gly Ser Ser
130                 135                 140

Ile Arg Gly Ser His Val Ala Ile Asp Asp Ile Glu Gly Ala Trp Asn
145                 150                 155                 160

Ser Gly Thr Lys Tyr Asp Gly Gly Asn Lys Gly His Arg Pro Ala Val
                165                 170                 175

Lys Gly Gly Tyr Phe Pro Val Pro Ser Val Asp Ser Ser Gln Asp Leu
            180                 185                 190

Arg Ser Thr Met Cys Leu Thr Met Glu Glu Met Gly Leu Val Val Glu
        195                 200                 205

Ala His His Thr Glu Ala Ala Thr Ala Ser Gln Asn Glu Val Ala Thr
210                 215                 220

Arg Phe Asn Thr Met Thr Lys Lys Ala Asp Glu Ile Gln Ile Tyr Lys
225                 230                 235                 240

Tyr Val Val His Asn Val Ala His Ala Phe Gly Lys Thr Ala Thr Phe
                245                 250                 255

Met Pro Lys Pro Met Phe Gly Asp Asn Gly Ser Gly Met His Cys His
            260                 265                 270

Met Ser Leu Ser Lys Asn Gly Thr Asn Leu Phe Ala Gly Asp Lys Tyr
        275                 280                 285

Gly Gly Leu Ser Glu Thr Ala Leu Phe Tyr Ile Gly Gly Ile Asn Lys
290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Ala Ser Pro
            340                 345                 350
```

```
Lys Ala Arg Arg Ile Glu Ala Arg Phe Pro Asp Pro Ala Ala Asn Pro
            355                 360                 365

Tyr Leu Cys Phe Ala Ala Leu Leu Met Ala Gly Leu Asp Gly Ile Ile
370                 375                 380

Asn Lys Ile His Pro Gly Asp Ala Met Asp Lys Asn Leu Tyr Asp Leu
385                 390                 395                 400

Pro Pro Glu Glu Glu Ala Glu Ile Pro Lys Val Ala Gly Ser Leu Asp
            405                 410                 415

Glu Ala Met Ala Ala Leu Asn Glu Asp Arg Glu Phe Leu Thr Arg Gly
            420                 425                 430

Gly Val Phe Thr Asp Asp Ala Ile Asp Ala Tyr Ile Glu Leu Arg Lys
            435                 440                 445

Glu Glu Met Asp Arg Val Arg Met Thr Pro His Pro Val Glu Phe Glu
            450                 455                 460

Leu Tyr Tyr Ser Val
465

<210> SEQ ID NO 35
<211> LENGTH: 1410
<212> TYPE: DNA
<213> ORGANISM: Artificial Sequence
<220> FEATURE:
<223> OTHER INFORMATION: ags1 variant nucleotide sequence (ags1m18)
<221> NAME/KEY: CDS
<222> LOCATION: (1)...(1410)

<400> SEQUENCE: 35 atg tcc gct gaa cac gtt ttg acg atg ctg aat gag cat gaa gtg aaa      48
Met Ser Ala Glu His Val Leu Thr Met Leu Asn Glu His Glu Val Lys
1               5                   10                  15 ttc gta gac ctg cgt ttc act gac acc aag ggt aag gaa cag cac gtg      96
Phe Val Asp Leu Arg Phe Thr Asp Thr Lys Gly Lys Glu Gln His Val
                20                  25                  30 act atc ccg gct cac cag gta aac gcc gac ttc ttc gaa gaa ggt aaa     144
Thr Ile Pro Ala His Gln Val Asn Ala Asp Phe Phe Glu Glu Gly Lys
            35                  40                  45 atg ttt gac ggc tcc tct atc ggt ggt tgg aag ggc atc aac gaa tct     192
Met Phe Asp Gly Ser Ser Ile Gly Gly Trp Lys Gly Ile Asn Glu Ser
50                  55                  60 gac atg gtg ctg atg ccg gac gcc agc acg gcg gtt ctg gat ccg ttc     240
Asp Met Val Leu Met Pro Asp Ala Ser Thr Ala Val Leu Asp Pro Phe
65                  70                  75                  80 tcc gaa gaa cct acg ctg atc att cgc tgt gac att ctc gag ccg ggc     288
Ser Glu Glu Pro Thr Leu Ile Ile Arg Cys Asp Ile Leu Glu Pro Gly
                85                  90                  95 acc atg caa ggc tac gat cgc gac ccg cgt tcc atc tcc aaa cgc gcc     336
Thr Met Gln Gly Tyr Asp Arg Asp Pro Arg Ser Ile Ser Lys Arg Ala
            100                 105                 110 gaa gac ttc ctg cgc tcc tcc ggc atc gcg gac acc gtg ctg ttc ggg     384
Glu Asp Phe Leu Arg Ser Ser Gly Ile Ala Asp Thr Val Leu Phe Gly
        115                 120                 125 cca gag cct gag ttc ttc ctg ttc gac gac atc cgc ttc ggc agc agc     432
Pro Glu Pro Glu Phe Phe Leu Phe Asp Asp Ile Arg Phe Gly Ser Ser
130                 135                 140 atc cgc ggt tcc cac gtg gcg atc gac gat atc gaa ggc gcc tgg aac     480
Ile Arg Gly Ser His Val Ala Ile Asp Asp Ile Glu Gly Ala Trp Asn
145                 150                 155                 160 tcc ggc aca aaa tac gac ggc ggc aac aaa ggc cac cgt ccg gcg gtg     528
Ser Gly Thr Lys Tyr Asp Gly Gly Asn Lys Gly His Arg Pro Ala Val
                165                 170                 175
```

```
aaa ggc ggt tac ttc ccg gtt cca tcg gtc gac tct tcg cag gat ctg       576
Lys Gly Gly Tyr Phe Pro Val Pro Ser Val Asp Ser Ser Gln Asp Leu
            180             185             190 cgt tcc acc atg tgt ctg acc atg gaa gag atg ggc ctg gtt gtt gaa       624
Arg Ser Thr Met Cys Leu Thr Met Glu Glu Met Gly Leu Val Val Glu
        195             200             205 gcg cac cac acg gaa tcc gcg acc gct agc cag aac gaa gtg gca acc       672
Ala His His Thr Glu Ser Ala Thr Ala Ser Gln Asn Glu Val Ala Thr
210             215             220 cgc ttc aac acc atg acc aag aaa gcc gac gaa att cag atc tat aag       720
Arg Phe Asn Thr Met Thr Lys Lys Ala Asp Glu Ile Gln Ile Tyr Lys
225             230             235             240 tac gtg gtg cac aac gtg gca cac gcc ttc ggt aaa acc gcg acc ttc       768
Tyr Val Val His Asn Val Ala His Ala Phe Gly Lys Thr Ala Thr Phe
            245             250             255 atg ccg aag ccc atg ttc ggc gac aac ggt tcc ggc atg cac tgc cac       816
Met Pro Lys Pro Met Phe Gly Asp Asn Gly Ser Gly Met His Cys His
        260             265             270 atg tcg ctg tcc aag aac ggc acc aac ctg ttc gcc ggc gac aaa tac       864
Met Ser Leu Ser Lys Asn Gly Thr Asn Leu Phe Ala Gly Asp Lys Tyr
    275             280             285 ggc ggc ctg tct gaa acc gca ctg ttc tac atc ggc ggt atc aac aag       912
Gly Gly Leu Ser Glu Thr Ala Leu Phe Tyr Ile Gly Gly Ile Asn Lys
290             295             300 cac gcc aag gcg atc aac gcg ctg gcc aac ccg acc acc aac tcg tac       960
His Ala Lys Ala Ile Asn Ala Leu Ala Asn Pro Thr Thr Asn Ser Tyr
305             310             315             320 aaa cgt ctg gtg cca ggc tac gaa gcg ccg gtg atg ctg gct tac tcc      1008
Lys Arg Leu Val Pro Gly Tyr Glu Ala Pro Val Met Leu Ala Tyr Ser
            325             330             335 gcc cgt aac cgc tcc gcg tcc atc cgt atc ccg gtg gtc gcc agc ccg      1056
Ala Arg Asn Arg Ser Ala Ser Ile Arg Ile Pro Val Val Ala Ser Pro
        340             345             350 aaa gcg cgc cgc atc gaa gcc cgc ttc ccg gat ccg gcg gct aac cca      1104
Lys Ala Arg Arg Ile Glu Ala Arg Phe Pro Asp Pro Ala Ala Asn Pro
    355             360             365 tac ctg tgc ttc gcc gca ctg ctg atg gcc ggc ctg gac ggc atc atc      1152
Tyr Leu Cys Phe Ala Ala Leu Leu Met Ala Gly Leu Asp Gly Ile Ile
370             375             380 aac aag atc cac cct ggc gac gcc atg gac aaa aac ctg tac gac ctg      1200
Asn Lys Ile His Pro Gly Asp Ala Met Asp Lys Asn Leu Tyr Asp Leu
385             390             395             400 ccg ccg gaa gaa gaa gcc gag atc cca aaa gtg gcc ggc tcg ctg gac      1248
Pro Pro Glu Glu Glu Ala Glu Ile Pro Lys Val Ala Gly Ser Leu Asp
            405             410             415 gag gcg atg gcc gcg ctg aac gaa gac cgc gag ttc ctg acc cgc ggc      1296
Glu Ala Met Ala Ala Leu Asn Glu Asp Arg Glu Phe Leu Thr Arg Gly
        420             425             430 ggc gtg ttc act gac gat gcg atc gat gcc tac atc gaa ctg cgc aaa      1344
Gly Val Phe Thr Asp Asp Ala Ile Asp Ala Tyr Ile Glu Leu Arg Lys
    435             440             445 gaa gag atg gac cgc gtt cgc atg acg cca cac ccg gtc gag ttc gaa      1392
Glu Glu Met Asp Arg Val Arg Met Thr Pro His Pro Val Glu Phe Glu
450             455             460 ctg tac tac agc gtc taa                                              1410
Leu Tyr Tyr Ser Val *
465

<210> SEQ ID NO 36
<211> LENGTH: 469
```

```
<212> TYPE: PRT
<213> ORGANISM: Artificial Sequence
<220> FEATURE:
<223> OTHER INFORMATION: AGS1 variant amino acid sequence (AGS1M18)

<400> SEQUENCE: 36
```

| | | | | | | | | | | | | | | |
|---|---|---|---|---|---|---|---|---|---|---|---|---|---|---|
| Met | Ser | Ala | Glu | His | Val | Leu | Thr | Met | Leu | Asn | Glu | His | Glu | Val | Lys |
| 1 | | | | 5 | | | | | 10 | | | | | 15 | |
| Phe | Val | Asp | Leu | Arg | Phe | Thr | Asp | Thr | Lys | Gly | Lys | Glu | Gln | His | Val |
| | | | 20 | | | | | 25 | | | | | 30 | | |
| Thr | Ile | Pro | Ala | His | Gln | Val | Asn | Ala | Asp | Phe | Phe | Glu | Glu | Gly | Lys |
| | | | 35 | | | | | 40 | | | | | 45 | | |
| Met | Phe | Asp | Gly | Ser | Ser | Ile | Gly | Gly | Trp | Lys | Gly | Ile | Asn | Glu | Ser |
| | 50 | | | | | 55 | | | | | 60 | | | | |
| Asp | Met | Val | Leu | Met | Pro | Asp | Ala | Ser | Thr | Ala | Val | Leu | Asp | Pro | Phe |
| 65 | | | | | 70 | | | | | 75 | | | | | 80 |
| Ser | Glu | Glu | Pro | Thr | Leu | Ile | Ile | Arg | Cys | Asp | Ile | Leu | Glu | Pro | Gly |
| | | | | 85 | | | | | 90 | | | | | 95 | |
| Thr | Met | Gln | Gly | Tyr | Asp | Arg | Asp | Pro | Arg | Ser | Ile | Ser | Lys | Arg | Ala |
| | | | | 100 | | | | | 105 | | | | | 110 | |
| Glu | Asp | Phe | Leu | Arg | Ser | Ser | Gly | Ile | Ala | Asp | Thr | Val | Leu | Phe | Gly |
| | | | | 115 | | | | | 120 | | | | | 125 | |
| Pro | Glu | Pro | Glu | Phe | Phe | Leu | Phe | Asp | Asp | Ile | Arg | Phe | Gly | Ser | Ser |
| | | 130 | | | | | 135 | | | | | 140 | | | |
| Ile | Arg | Gly | Ser | His | Val | Ala | Ile | Asp | Asp | Ile | Glu | Gly | Ala | Trp | Asn |
| 145 | | | | | 150 | | | | | 155 | | | | | 160 |
| Ser | Gly | Thr | Lys | Tyr | Asp | Gly | Gly | Asn | Lys | Gly | His | Arg | Pro | Ala | Val |
| | | | | 165 | | | | | 170 | | | | | 175 | |
| Lys | Gly | Gly | Tyr | Phe | Pro | Val | Pro | Ser | Val | Asp | Ser | Ser | Gln | Asp | Leu |
| | | | 180 | | | | | 185 | | | | | 190 | | |
| Arg | Ser | Thr | Met | Cys | Leu | Thr | Met | Glu | Glu | Met | Gly | Leu | Val | Val | Glu |
| | | | | 195 | | | | | 200 | | | | | 205 | |
| Ala | His | His | Thr | Glu | Ser | Ala | Thr | Ala | Ser | Gln | Asn | Glu | Val | Ala | Thr |
| | | 210 | | | | | 215 | | | | | 220 | | | |
| Arg | Phe | Asn | Thr | Met | Thr | Lys | Lys | Ala | Asp | Glu | Ile | Gln | Ile | Tyr | Lys |
| 225 | | | | | 230 | | | | | 235 | | | | | 240 |
| Tyr | Val | Val | His | Asn | Val | Ala | His | Ala | Phe | Gly | Lys | Thr | Ala | Thr | Phe |
| | | | | 245 | | | | | 250 | | | | | 255 | |
| Met | Pro | Lys | Pro | Met | Phe | Gly | Asp | Asn | Gly | Ser | Gly | Met | His | Cys | His |
| | | | 260 | | | | | 265 | | | | | 270 | | |
| Met | Ser | Leu | Ser | Lys | Asn | Gly | Thr | Asn | Leu | Phe | Ala | Gly | Asp | Lys | Tyr |
| | | 275 | | | | | 280 | | | | | 285 | | | |
| Gly | Gly | Leu | Ser | Glu | Thr | Ala | Leu | Phe | Tyr | Ile | Gly | Gly | Ile | Asn | Lys |
| | | 290 | | | | | 295 | | | | | 300 | | | |
| His | Ala | Lys | Ala | Ile | Asn | Ala | Leu | Ala | Asn | Pro | Thr | Thr | Asn | Ser | Tyr |
| 305 | | | | | 310 | | | | | 315 | | | | | 320 |
| Lys | Arg | Leu | Val | Pro | Gly | Tyr | Glu | Ala | Pro | Val | Met | Leu | Ala | Tyr | Ser |
| | | | | 325 | | | | | 330 | | | | | 335 | |
| Ala | Arg | Asn | Arg | Ser | Ala | Ser | Ile | Arg | Ile | Pro | Val | Val | Ala | Ser | Pro |
| | | | 340 | | | | | 345 | | | | | 350 | | |
| Lys | Ala | Arg | Arg | Ile | Glu | Ala | Arg | Phe | Pro | Asp | Pro | Ala | Ala | Asn | Pro |
| | | | 355 | | | | | 360 | | | | | 365 | | |
| Tyr | Leu | Cys | Phe | Ala | Ala | Leu | Leu | Met | Ala | Gly | Leu | Asp | Gly | Ile | Ile |
| | 370 | | | | | 375 | | | | | 380 | | | | |
| Asn | Lys | Ile | His | Pro | Gly | Asp | Ala | Met | Asp | Lys | Asn | Leu | Tyr | Asp | Leu |

```
                385                 390                 395                 400

Pro Pro Glu Glu Glu Ala Glu Ile Pro Lys Val Ala Gly Ser Leu Asp
                      405                 410                 415

Glu Ala Met Ala Ala Leu Asn Glu Asp Arg Glu Phe Leu Thr Arg Gly
                      420                 425                 430

Gly Val Phe Thr Asp Asp Ala Ile Asp Ala Tyr Ile Glu Leu Arg Lys
                      435                 440                 445

Glu Glu Met Asp Arg Val Arg Met Thr Pro His Pro Val Glu Phe Glu
                      450                 455                 460

Leu Tyr Tyr Ser Val
      465

<210> SEQ ID NO 37
<211> LENGTH: 1410
<212> TYPE: DNA
<213> ORGANISM: Artificial Sequence
<220> FEATURE:
<223> OTHER INFORMATION: ags1 variant nucleotide sequence (ags1m19)
<221> NAME/KEY: CDS
<222> LOCATION: (1)...(1410)

<400> SEQUENCE: 37 atg tcc gct gaa cac gtt ttg acg atg ctg aat gag cat gaa gtg aaa        48
Met Ser Ala Glu His Val Leu Thr Met Leu Asn Glu His Glu Val Lys
 1               5                  10                  15 ttc gta gac ctg cgt ttc act gac acc aag ggt aag gaa cag cac gtg        96
Phe Val Asp Leu Arg Phe Thr Asp Thr Lys Gly Lys Glu Gln His Val
             20                  25                  30 act atc ccg gct cac cag gta aac gcc gac ttc ttc gaa gaa ggt aaa       144
Thr Ile Pro Ala His Gln Val Asn Ala Asp Phe Phe Glu Glu Gly Lys
         35                  40                  45 atg ttt gac ggc tcc tct atc ggt ggt tgg aag ggc atc aac gaa tct       192
Met Phe Asp Gly Ser Ser Ile Gly Gly Trp Lys Gly Ile Asn Glu Ser
     50                  55                  60 gac atg gtg ctg atg ccg gac gcc agc acg gcg gtt ctg gat ccg ttc       240
Asp Met Val Leu Met Pro Asp Ala Ser Thr Ala Val Leu Asp Pro Phe
 65                  70                  75                  80 tcc gaa gaa cct acg ctg atc att cgc tgt gac att ctc gag ccg ggc       288
Ser Glu Glu Pro Thr Leu Ile Ile Arg Cys Asp Ile Leu Glu Pro Gly
                 85                  90                  95 acc atg caa ggc tac gat cgc gac ccg cgt tcc atc tcc aaa cgc gcc       336
Thr Met Gln Gly Tyr Asp Arg Asp Pro Arg Ser Ile Ser Lys Arg Ala
            100                 105                 110 gaa gac ttc ctg cgc tcc tcc ggc atc gcg gac acc gtg ctg ttc ggg       384
Glu Asp Phe Leu Arg Ser Ser Gly Ile Ala Asp Thr Val Leu Phe Gly
        115                 120                 125 cca gag cct gag ttc ttc ctg ttc gac gac atc cgc ttc ggc agc agc       432
Pro Glu Pro Glu Phe Phe Leu Phe Asp Asp Ile Arg Phe Gly Ser Ser
    130                 135                 140 atc cgc ggt tcc cac gtg gcg atc gac gat atc gaa ggc gcc tgg aac       480
Ile Arg Gly Ser His Val Ala Ile Asp Asp Ile Glu Gly Ala Trp Asn
145                 150                 155                 160 tcc ggc aca aaa tac gac ggc ggc aac aaa ggc cac cgt ccg gcg gtg       528
Ser Gly Thr Lys Tyr Asp Gly Gly Asn Lys Gly His Arg Pro Ala Val
                165                 170                 175 aaa ggc ggt tac ttc ccg gtt cca tcg gtc gac tct tcg cag gat ctg       576
Lys Gly Gly Tyr Phe Pro Val Pro Ser Val Asp Ser Ser Gln Asp Leu
            180                 185                 190 cgt tcc acc atg tgt ctg acc atg gaa gag atg ggc ctg gtg gtt gaa       624
Arg Ser Thr Met Cys Leu Thr Met Glu Glu Met Gly Leu Val Val Glu
        195                 200                 205
```

```
gcg cac cac tcc gag gcc gcg acc gct agc cag aac gaa gtg gca acc      672
Ala His His Ser Glu Ala Ala Thr Ala Ser Gln Asn Glu Val Ala Thr
    210             215                 220 cgc ttc aac acc atg acc aag aaa gcc gac gaa att cag atc tat aag      720
Arg Phe Asn Thr Met Thr Lys Lys Ala Asp Glu Ile Gln Ile Tyr Lys
225             230                 235                 240 tac gtg gtg cac aac gtg gca cac gcc ttc ggt aaa acc gcg acc ttc      768
Tyr Val Val His Asn Val Ala His Ala Phe Gly Lys Thr Ala Thr Phe
                245                 250                 255 atg ccg aag ccc atg ttc ggc gac aac ggt tcc ggc atg cac tgc cac      816
Met Pro Lys Pro Met Phe Gly Asp Asn Gly Ser Gly Met His Cys His
        260                 265                 270 atg tcg ctg tcc aag aac ggc acc aac ctg ttc gcc ggc gac aaa tac      864
Met Ser Leu Ser Lys Asn Gly Thr Asn Leu Phe Ala Gly Asp Lys Tyr
    275                 280                 285 ggc ggc ctg tct gaa acc gca ctg ttc tac atc ggc ggt atc aac aag      912
Gly Gly Leu Ser Glu Thr Ala Leu Phe Tyr Ile Gly Gly Ile Asn Lys
290                 295                 300 cac gcc aag gcg atc aac gcg ctg gcc aac ccg acc acc aac tcg tac      960
His Ala Lys Ala Ile Asn Ala Leu Ala Asn Pro Thr Thr Asn Ser Tyr
305                 310                 315                 320 aaa cgt ctg gtg cca ggc tac gaa gcg ccg gtg atg ctg gct tac tcc     1008
Lys Arg Leu Val Pro Gly Tyr Glu Ala Pro Val Met Leu Ala Tyr Ser
                325                 330                 335 gcc cgt aac cgc tcc gcg tcc atc cgt atc ccg gtg gtc gcc agc ccg     1056
Ala Arg Asn Arg Ser Ala Ser Ile Arg Ile Pro Val Val Ala Ser Pro
            340                 345                 350 aaa gcg cgc cgc atc gaa gcc cgc ttc ccg gat ccg gcg gct aac cca     1104
Lys Ala Arg Arg Ile Glu Ala Arg Phe Pro Asp Pro Ala Ala Asn Pro
        355                 360                 365 tac ctg tgc ttc gcc gca ctg ctg atg gcc ggc ctg gac ggc atc atc     1152
Tyr Leu Cys Phe Ala Ala Leu Leu Met Ala Gly Leu Asp Gly Ile Ile
370                 375                 380 aac aag atc cac cct ggc gac gcc atg gac aaa aac ctg tac gac ctg     1200
Asn Lys Ile His Pro Gly Asp Ala Met Asp Lys Asn Leu Tyr Asp Leu
385                 390                 395                 400 ccg ccg gaa gaa gaa gcc gag atc cca aaa gtg gcc ggc tcg ctg gac     1248
Pro Pro Glu Glu Glu Ala Glu Ile Pro Lys Val Ala Gly Ser Leu Asp
                405                 410                 415 gag gcg atg gcc gcg ctg aac gaa gac cgc gag ttc ctg acc cgc ggc     1296
Glu Ala Met Ala Ala Leu Asn Glu Asp Arg Glu Phe Leu Thr Arg Gly
            420                 425                 430 ggc gtg ttc act gac gat gcg atc gat gcc tac atc gaa ctg cgc aaa     1344
Gly Val Phe Thr Asp Asp Ala Ile Asp Ala Tyr Ile Glu Leu Arg Lys
        435                 440                 445 gaa gag atg gac cgc gtt cgc atg acg cca cac ccg gtc gag ttc gaa     1392
Glu Glu Met Asp Arg Val Arg Met Thr Pro His Pro Val Glu Phe Glu
450                 455                 460 ctg tac tac agc gtc taa                                             1410
Leu Tyr Tyr Ser Val *
465

<210> SEQ ID NO 38
<211> LENGTH: 469
<212> TYPE: PRT
<213> ORGANISM: Artificial Sequence
<220> FEATURE:
<223> OTHER INFORMATION: AGS1 variant amino acid sequence (AGS1M19)

<400> SEQUENCE: 38

Met Ser Ala Glu His Val Leu Thr Met Leu Asn Glu His Glu Val Lys
```

```
              1               5                  10                 15
        Phe Val Asp Leu Arg Phe Thr Asp Thr Lys Gly Lys Glu Gln His Val
                        20                  25                  30

Thr Ile Pro Ala His Gln Val Asn Ala Asp Phe Phe Glu Glu Gly Lys
                        35                  40                  45

Met Phe Asp Gly Ser Ser Ile Gly Gly Trp Lys Gly Ile Asn Glu Ser
                        50                  55                  60

Asp Met Val Leu Met Pro Asp Ala Ser Thr Ala Val Leu Asp Pro Phe
        65                  70                  75                  80

Ser Glu Glu Pro Thr Leu Ile Ile Arg Cys Asp Ile Leu Glu Pro Gly
                        85                  90                  95

Thr Met Gln Gly Tyr Asp Arg Asp Pro Arg Ser Ile Ser Lys Arg Ala
                        100                 105                 110

Glu Asp Phe Leu Arg Ser Ser Gly Ile Ala Asp Thr Val Leu Phe Gly
                        115                 120                 125

Pro Glu Pro Glu Phe Phe Leu Phe Asp Asp Ile Arg Phe Gly Ser Ser
                        130                 135                 140

Ile Arg Gly Ser His Val Ala Ile Asp Asp Ile Glu Gly Ala Trp Asn
        145                 150                 155                 160

Ser Gly Thr Lys Tyr Asp Gly Gly Asn Lys Gly His Arg Pro Ala Val
                        165                 170                 175

Lys Gly Gly Tyr Phe Pro Val Pro Ser Val Asp Ser Ser Gln Asp Leu
                        180                 185                 190

Arg Ser Thr Met Cys Leu Thr Met Glu Glu Met Gly Leu Val Val Glu
                        195                 200                 205

Ala His His Ser Glu Ala Ala Thr Ala Ser Gln Asn Glu Val Ala Thr
                        210                 215                 220

Arg Phe Asn Thr Met Thr Lys Lys Ala Asp Glu Ile Gln Ile Tyr Lys
        225                 230                 235                 240

Tyr Val Val His Asn Val Ala His Ala Phe Gly Lys Thr Ala Thr Phe
                        245                 250                 255

Met Pro Lys Pro Met Phe Gly Asp Asn Gly Ser Gly Met His Cys His
                        260                 265                 270

Met Ser Leu Ser Lys Asn Gly Thr Asn Leu Phe Ala Gly Asp Lys Tyr
                        275                 280                 285

Gly Gly Leu Ser Glu Thr Ala Leu Phe Tyr Ile Gly Gly Ile Asn Lys
                        290                 295                 300

His Ala Lys Ala Ile Asn Ala Leu Ala Asn Pro Thr Thr Asn Ser Tyr
        305                 310                 315                 320

Lys Arg Leu Val Pro Gly Tyr Glu Ala Pro Val Met Leu Ala Tyr Ser
                        325                 330                 335

Ala Arg Asn Arg Ser Ala Ser Ile Arg Ile Pro Val Val Ala Ser Pro
                        340                 345                 350

Lys Ala Arg Arg Ile Glu Ala Arg Phe Pro Asp Pro Ala Ala Asn Pro
                        355                 360                 365

Tyr Leu Cys Phe Ala Ala Leu Leu Met Ala Gly Leu Asp Gly Ile Ile
                        370                 375                 380

Asn Lys Ile His Pro Gly Asp Ala Met Asp Lys Asn Leu Tyr Asp Leu
        385                 390                 395                 400

Pro Pro Glu Glu Glu Ala Glu Ile Pro Lys Val Ala Gly Ser Leu Asp
                        405                 410                 415

Glu Ala Met Ala Ala Leu Asn Glu Asp Arg Glu Phe Leu Thr Arg Gly
                        420                 425                 430
```

-continued

```
Gly Val Phe Thr Asp Asp Ala Ile Asp Ala Tyr Ile Glu Leu Arg Lys
            435                 440                 445

Glu Glu Met Asp Arg Val Arg Met Thr Pro His Pro Val Glu Phe Glu
    450                 455                 460

Leu Tyr Tyr Ser Val
465

<210> SEQ ID NO 39
<211> LENGTH: 1410
<212> TYPE: DNA
<213> ORGANISM: Artificial Sequence
<220> FEATURE:
<223> OTHER INFORMATION: ags1 variant nucleotide sequence (ags1m20)
<221> NAME/KEY: CDS
<222> LOCATION: (1)...(1410)

<400> SEQUENCE: 39 atg tcc gct gaa cac gtt ttg acg atg ctg aat gag cat gaa gtg aaa      48
Met Ser Ala Glu His Val Leu Thr Met Leu Asn Glu His Glu Val Lys
 1               5                  10                  15 ttc gta gac ctg cgt ttc act gac acc aag ggt aag gaa cag cac gtg      96
Phe Val Asp Leu Arg Phe Thr Asp Thr Lys Gly Lys Glu Gln His Val
                 20                  25                  30 act atc ccg gct cac cag gta aac gcc gac ttc ttc gaa gaa ggt aaa     144
Thr Ile Pro Ala His Gln Val Asn Ala Asp Phe Phe Glu Glu Gly Lys
             35                  40                  45 atg ttt gac ggc tcc tct atc ggt ggt tgg aag ggc atc aac gaa tct     192
Met Phe Asp Gly Ser Ser Ile Gly Gly Trp Lys Gly Ile Asn Glu Ser
         50                  55                  60 gac atg gtg ctg atg ccg gac gcc agc acg gcg gtt ctg gat ccg ttc     240
Asp Met Val Leu Met Pro Asp Ala Ser Thr Ala Val Leu Asp Pro Phe
 65                  70                  75                  80 tcc gaa gaa cct acg ctg atc att cgc tgt gac att ctc gag ccg ggc     288
Ser Glu Glu Pro Thr Leu Ile Ile Arg Cys Asp Ile Leu Glu Pro Gly
                 85                  90                  95 acc atg caa ggc tac gat cgc gac ccg cgt tcc atc tcc aaa cgc gcc     336
Thr Met Gln Gly Tyr Asp Arg Asp Pro Arg Ser Ile Ser Lys Arg Ala
            100                 105                 110 gaa gac ttc ctg cgc tcc tcc ggc atc gcg gac acc gtg ctg ttc ggg     384
Glu Asp Phe Leu Arg Ser Ser Gly Ile Ala Asp Thr Val Leu Phe Gly
        115                 120                 125 cca gag cct gag ttc ttc ctg ttc gac gac atc cgc ttc ggc agc agc     432
Pro Glu Pro Glu Phe Phe Leu Phe Asp Asp Ile Arg Phe Gly Ser Ser
    130                 135                 140 atc cgc ggt tcc cac gtg gcg atc gac gat atc gaa ggc gcc tgg aac     480
Ile Arg Gly Ser His Val Ala Ile Asp Asp Ile Glu Gly Ala Trp Asn
145                 150                 155                 160 tcc ggc aca aaa tac gac ggc ggc aac aaa ggc cac cgt ccg gcg gtg     528
Ser Gly Thr Lys Tyr Asp Gly Gly Asn Lys Gly His Arg Pro Ala Val
                165                 170                 175 aaa ggc ggt tac ttc ccg gtt cca tcg gtc gac tct tcg cag gat ctg     576
Lys Gly Gly Tyr Phe Pro Val Pro Ser Val Asp Ser Ser Gln Asp Leu
            180                 185                 190 cgt tcc acc atg tgt ctg acc atg gaa gag atg ggc ctg gtg gtt gaa     624
Arg Ser Thr Met Cys Leu Thr Met Glu Glu Met Gly Leu Val Val Glu
        195                 200                 205 gcg cac cac atg gag cat gcg acc gct agc cag aac gaa gtg gca acc     672
Ala His His Met Glu His Ala Thr Ala Ser Gln Asn Glu Val Ala Thr
    210                 215                 220 cgc ttc aac acc atg acc aag aaa gcc gac gaa att cag atc tat aag     720
Arg Phe Asn Thr Met Thr Lys Lys Ala Asp Glu Ile Gln Ile Tyr Lys
225                 230                 235                 240
```

```
tac gtg gtg cac aac gtg gca cac gcc ttc ggt aaa acc gcg acc ttc      768
Tyr Val Val His Asn Val Ala His Ala Phe Gly Lys Thr Ala Thr Phe
            245                 250                 255 atg ccg aag ccc atg ttc ggc gac aac ggt tcc ggc atg cac tgc cac      816
Met Pro Lys Pro Met Phe Gly Asp Asn Gly Ser Gly Met His Cys His
        260                 265                 270 atg tcg ctg tcc aag aac ggc acc aac ctg ttc gcc ggc gac aaa tac      864
Met Ser Leu Ser Lys Asn Gly Thr Asn Leu Phe Ala Gly Asp Lys Tyr
    275                 280                 285 ggc ggc ctg tct gaa acc gca ctg ttc tac atc ggc ggt atc aac aag      912
Gly Gly Leu Ser Glu Thr Ala Leu Phe Tyr Ile Gly Gly Ile Asn Lys
290                 295                 300 cac gcc aag gcg atc aac gcg ctg gcc aac ccg acc acc aac tcg tac      960
His Ala Lys Ala Ile Asn Ala Leu Ala Asn Pro Thr Thr Asn Ser Tyr
305                 310                 315                 320 aaa cgt ctg gtg cca ggc tac gaa gcg ccg gtg atg ctg gct tac tcc     1008
Lys Arg Leu Val Pro Gly Tyr Glu Ala Pro Val Met Leu Ala Tyr Ser
                325                 330                 335 gcc cgt aac cgc tcc gcg tcc atc cgt atc ccg gtg gtc gcc agc ccg     1056
Ala Arg Asn Arg Ser Ala Ser Ile Arg Ile Pro Val Val Ala Ser Pro
            340                 345                 350 aaa gcg cgc cgc atc gaa gcc cgc ttc ccg gat ccg gcg gct aac cca     1104
Lys Ala Arg Arg Ile Glu Ala Arg Phe Pro Asp Pro Ala Ala Asn Pro
        355                 360                 365 tac ctg tgc ttc gcc gca ctg ctg atg gcc ggc ctg gac ggc atc atc     1152
Tyr Leu Cys Phe Ala Ala Leu Leu Met Ala Gly Leu Asp Gly Ile Ile
    370                 375                 380 aac aag atc cac cct ggc gac gcc atg gac aaa aac ctg tac gac ctg     1200
Asn Lys Ile His Pro Gly Asp Ala Met Asp Lys Asn Leu Tyr Asp Leu
385                 390                 395                 400 ccg ccg gaa gaa gaa gcc gag atc cca aaa gtg gcc ggc tcg ctg gac     1248
Pro Pro Glu Glu Glu Ala Glu Ile Pro Lys Val Ala Gly Ser Leu Asp
                405                 410                 415 gag gcg atg gcc gcg ctg aac gaa gac cgc gag ttc ctg acc cgc ggc     1296
Glu Ala Met Ala Ala Leu Asn Glu Asp Arg Glu Phe Leu Thr Arg Gly
            420                 425                 430 ggc gtg ttc act gac gat gcg atc gat gcc tac atc gaa ctg cgc aaa     1344
Gly Val Phe Thr Asp Asp Ala Ile Asp Ala Tyr Ile Glu Leu Arg Lys
        435                 440                 445 gaa gag atg gac cgc gtt cgc atg acg cca cac ccg gtc gag ttc gaa     1392
Glu Glu Met Asp Arg Val Arg Met Thr Pro His Pro Val Glu Phe Glu
    450                 455                 460 ctg tac tac agc gtc taa                                              1410
Leu Tyr Tyr Ser Val *
465

<210> SEQ ID NO 40
<211> LENGTH: 469
<212> TYPE: PRT
<213> ORGANISM: Artificial Sequence
<220> FEATURE:
<223> OTHER INFORMATION: AGS1 variant amino acid sequence (AGS1M20)

<400> SEQUENCE: 40

Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
            20                  25                  30

Thr Ile Pro Ala His Gln Val Asn Ala Asp Phe Phe Glu Glu Gly Lys
        35                  40                  45
```

-continued

```
Met Phe Asp Gly Ser Ser Ile Gly Gly Trp Lys Gly Ile Asn Glu Ser
    50                  55                  60

Asp Met Val Leu Met Pro Asp Ala Ser Thr Ala Val Leu Asp Pro Phe
 65                  70                  75                  80

Ser Glu Glu Pro Thr Leu Ile Ile Arg Cys Asp Ile Leu Glu Pro Gly
                 85                  90                  95

Thr Met Gln Gly Tyr Asp Arg Asp Pro Arg Ser Ile Ser Lys Arg Ala
                100                 105                 110

Glu Asp Phe Leu Arg Ser Ser Gly Ile Ala Asp Thr Val Leu Phe Gly
            115                 120                 125

Pro Glu Pro Glu Phe Phe Leu Phe Asp Asp Ile Arg Phe Gly Ser Ser
    130                 135                 140

Ile Arg Gly Ser His Val Ala Ile Asp Asp Ile Glu Gly Ala Trp Asn
145                 150                 155                 160

Ser Gly Thr Lys Tyr Asp Gly Gly Asn Lys Gly His Arg Pro Ala Val
                165                 170                 175

Lys Gly Gly Tyr Phe Pro Val Pro Ser Val Asp Ser Ser Gln Asp Leu
                180                 185                 190

Arg Ser Thr Met Cys Leu Thr Met Glu Glu Met Gly Leu Val Val Glu
            195                 200                 205

Ala His His Met Glu His Ala Thr Ala Ser Gln Asn Glu Val Ala Thr
    210                 215                 220

Arg Phe Asn Thr Met Thr Lys Lys Ala Asp Glu Ile Gln Ile Tyr Lys
225                 230                 235                 240

Tyr Val Val His Asn Val Ala His Ala Phe Gly Lys Thr Ala Thr Phe
                245                 250                 255

Met Pro Lys Pro Met Phe Gly Asp Asn Gly Ser Gly Met His Cys His
                260                 265                 270

Met Ser Leu Ser Lys Asn Gly Thr Asn Leu Phe Ala Gly Asp Lys Tyr
            275                 280                 285

Gly Gly Leu Ser Glu Thr Ala Leu Phe Tyr Ile Gly Gly Ile Asn Lys
    290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Ala Ser Pro
            340                 345                 350

Lys Ala Arg Arg Ile Glu Ala Arg Phe Pro Asp Pro Ala Ala Asn Pro
    355                 360                 365

Tyr Leu Cys Phe Ala Ala Leu Leu Met Ala Gly Leu Asp Gly Ile Ile
370                 375                 380

Asn Lys Ile His Pro Gly Asp Ala Met Asp Lys Asn Leu Tyr Asp Leu
385                 390                 395                 400

Pro Pro Glu Glu Glu Ala Glu Ile Pro Lys Val Ala Gly Ser Leu Asp
                405                 410                 415

Glu Ala Met Ala Ala Leu Asn Glu Asp Arg Glu Phe Leu Thr Arg Gly
            420                 425                 430

Gly Val Phe Thr Asp Asp Ala Ile Asp Ala Tyr Ile Glu Leu Arg Lys
    435                 440                 445

Glu Glu Met Asp Arg Val Arg Met Thr Pro His Pro Val Glu Phe Glu
    450                 455                 460

Leu Tyr Tyr Ser Val
465
```

<210> SEQ ID NO 41
<211> LENGTH: 1410
<212> TYPE: DNA
<213> ORGANISM: Artificial Sequence
<220> FEATURE:
<223> OTHER INFORMATION: ags1 variant nucleotide sequence (ags1m21)
<221> NAME/KEY: CDS
<222> LOCATION: (1)...(1410)

<400> SEQUENCE: 41

| | | | | | | | | | | | | | | | | |
|---|---|---|---|---|---|---|---|---|---|---|---|---|---|---|---|---|
| atg | tcc | gct | gaa | cac | gtt | ttg | acg | atg | ctg | aat | gag | cat | gaa | gtg | aaa | 48 |
| Met | Ser | Ala | Glu | His | Val | Leu | Thr | Met | Leu | Asn | Glu | His | Glu | Val | Lys | |
| 1 | | | | 5 | | | | | 10 | | | | | 15 | | |
| ttc | gta | gac | ctg | cgt | ttc | act | gac | acc | aag | ggt | aag | gaa | cag | cac | gtg | 96 |
| Phe | Val | Asp | Leu | Arg | Phe | Thr | Asp | Thr | Lys | Gly | Lys | Glu | Gln | His | Val | |
| | | | 20 | | | | | 25 | | | | | 30 | | | |
| act | atc | ccg | gct | cac | cag | gta | aac | gcc | gac | ttc | ttc | gaa | gaa | ggt | aaa | 144 |
| Thr | Ile | Pro | Ala | His | Gln | Val | Asn | Ala | Asp | Phe | Phe | Glu | Glu | Gly | Lys | |
| | 35 | | | | | 40 | | | | | 45 | | | | | |
| atg | ttt | gac | ggc | tcc | tct | atc | ggt | ggt | tgg | aag | ggc | atc | aac | gaa | tct | 192 |
| Met | Phe | Asp | Gly | Ser | Ser | Ile | Gly | Gly | Trp | Lys | Gly | Ile | Asn | Glu | Ser | |
| 50 | | | | | 55 | | | | | 60 | | | | | | |
| gac | atg | gtg | ctg | atg | ccg | gac | gcc | agc | acg | gcg | gtt | ctg | gat | ccg | ttc | 240 |
| Asp | Met | Val | Leu | Met | Pro | Asp | Ala | Ser | Thr | Ala | Val | Leu | Asp | Pro | Phe | |
| 65 | | | | 70 | | | | | 75 | | | | | 80 | | |
| ttc | gaa | gaa | cct | acg | ctg | atc | att | cgc | tgt | gac | att | ctc | gag | ccg | ggc | 288 |
| Phe | Glu | Glu | Pro | Thr | Leu | Ile | Ile | Arg | Cys | Asp | Ile | Leu | Glu | Pro | Gly | |
| | | | | 85 | | | | | 90 | | | | | 95 | | |
| acc | atg | caa | ggc | tac | gat | cgc | gac | ccg | cgt | tcc | atc | tcc | aaa | cgc | gcc | 336 |
| Thr | Met | Gln | Gly | Tyr | Asp | Arg | Asp | Pro | Arg | Ser | Ile | Ser | Lys | Arg | Ala | |
| | | | 100 | | | | | 105 | | | | | 110 | | | |
| gaa | gac | ttc | ctg | cgc | tcc | tcc | ggc | atc | gcg | gac | acc | gtg | ctg | ttc | ggg | 384 |
| Glu | Asp | Phe | Leu | Arg | Ser | Ser | Gly | Ile | Ala | Asp | Thr | Val | Leu | Phe | Gly | |
| | | 115 | | | | | 120 | | | | | 125 | | | | |
| cca | gag | cct | gag | ttc | ttc | ctg | ttc | gac | gac | atc | cgc | ttc | ggc | agc | agc | 432 |
| Pro | Glu | Pro | Glu | Phe | Phe | Leu | Phe | Asp | Asp | Ile | Arg | Phe | Gly | Ser | Ser | |
| | 130 | | | | | 135 | | | | | 140 | | | | | |
| atc | cgc | ggt | tcc | cac | gtg | gcg | atc | gac | gat | atc | gaa | ggc | gcc | tgg | agc | 480 |
| Ile | Arg | Gly | Ser | His | Val | Ala | Ile | Asp | Asp | Ile | Glu | Gly | Ala | Trp | Ser | |
| 145 | | | | | 150 | | | | | 155 | | | | | 160 | |
| tcc | ggc | aca | aaa | tac | gac | aga | ggc | aac | aaa | ggc | cac | cgt | ccg | gcg | gtg | 528 |
| Ser | Gly | Thr | Lys | Tyr | Asp | Arg | Gly | Asn | Lys | Gly | His | Arg | Pro | Ala | Val | |
| | | | | 165 | | | | | 170 | | | | | 175 | | |
| aaa | ggc | ggt | tac | ttc | ccg | gtt | cca | ccg | gtc | gac | tct | tcg | cag | gat | ctg | 576 |
| Lys | Gly | Gly | Tyr | Phe | Pro | Val | Pro | Pro | Val | Asp | Ser | Ser | Gln | Asp | Leu | |
| | | | 180 | | | | | 185 | | | | | 190 | | | |
| cgt | tcc | acc | atg | tgt | ctg | acc | atg | gaa | gag | atg | ggc | ctg | gtg | gtt | gaa | 624 |
| Arg | Ser | Thr | Met | Cys | Leu | Thr | Met | Glu | Glu | Met | Gly | Leu | Val | Val | Glu | |
| | | 195 | | | | | 200 | | | | | 205 | | | | |
| gcg | cac | cac | cac | gaa | atg | gcg | acc | gcc | ggt | cag | aac | gaa | gtg | gca | acc | 672 |
| Ala | His | His | His | Glu | Met | Ala | Thr | Ala | Gly | Gln | Asn | Glu | Val | Ala | Thr | |
| | 210 | | | | | 215 | | | | | 220 | | | | | |
| cgc | ttc | aac | acc | atg | acc | aag | aaa | gcc | gac | gaa | att | cag | atc | tat | aag | 720 |
| Arg | Phe | Asn | Thr | Met | Thr | Lys | Lys | Ala | Asp | Glu | Ile | Gln | Ile | Tyr | Lys | |
| 225 | | | | | 230 | | | | | 235 | | | | | 240 | |
| tac | gtg | gtg | cac | aac | gtg | gcg | cac | gcc | ttc | ggt | aaa | acc | gcg | acc | ttc | 768 |
| Tyr | Val | Val | His | Asn | Val | Ala | His | Ala | Phe | Gly | Lys | Thr | Ala | Thr | Phe | |
| | | | | 245 | | | | | 250 | | | | | 255 | | |
| atg | ccg | aag | ccc | atg | ttc | ggc | gac | aac | ggt | tcc | ggc | atg | cac | tgc | cac | 816 |
| Met | Pro | Lys | Pro | Met | Phe | Gly | Asp | Asn | Gly | Ser | Gly | Met | His | Cys | His | |
| | | | 260 | | | | | 265 | | | | | 270 | | | |

```
atg tcg ctg tcc aag aac ggc acc aac ctg ttc gcc ggc gac aaa tac         864
Met Ser Leu Ser Lys Asn Gly Thr Asn Leu Phe Ala Gly Asp Lys Tyr
        275                 280                 285 ggc ggc ctg tct gaa acc gca ctg ttc tac atc ggc ggt atc atc aag         912
Gly Gly Leu Ser Glu Thr Ala Leu Phe Tyr Ile Gly Gly Ile Ile Lys
    290                 295                 300 cac gcc aag gcg atc aac gcg ctg gcc aac ccg acc acc aac tcg tac         960
His Ala Lys Ala Ile Asn Ala Leu Ala Asn Pro Thr Thr Asn Ser Tyr
305                 310                 315                 320 aaa cgt ctg gtg cca ggc tac gaa gcg ccg gtg atg ctg gct tac tcc        1008
Lys Arg Leu Val Pro Gly Tyr Glu Ala Pro Val Met Leu Ala Tyr Ser
                325                 330                 335 gcc cgt aac cgc tcc gcg tcc atc cgt atc ccg gtg gtc gcc agc ccg        1056
Ala Arg Asn Arg Ser Ala Ser Ile Arg Ile Pro Val Val Ala Ser Pro
            340                 345                 350 aaa gcg cgc cgc atc gaa gcc cgc ttc ccg gat ccg gcg gct aac cca        1104
Lys Ala Arg Arg Ile Glu Ala Arg Phe Pro Asp Pro Ala Ala Asn Pro
        355                 360                 365 tac ctg tgc ttc gcc gca ctg ctg atg gcc ggc ctg gac ggc atc atc        1152
Tyr Leu Cys Phe Ala Ala Leu Leu Met Ala Gly Leu Asp Gly Ile Ile
    370                 375                 380 aac aag atc cac cct ggc gac gcc atg gac aaa aac ctg tac gac ctg        1200
Asn Lys Ile His Pro Gly Asp Ala Met Asp Lys Asn Leu Tyr Asp Leu
385                 390                 395                 400 ccg ccg gaa gaa gaa gcc gag atc cca aaa gtg gcc ggc tcg ctg gac        1248
Pro Pro Glu Glu Glu Ala Glu Ile Pro Lys Val Ala Gly Ser Leu Asp
                405                 410                 415 gag gcg atg gcc gcg ctg aac gaa gac cgc gag ttc ctg acc cgc ggc        1296
Glu Ala Met Ala Ala Leu Asn Glu Asp Arg Glu Phe Leu Thr Arg Gly
            420                 425                 430 ggc gtg ttc acc gac gat gcg atc gat gcc tac atc gaa ctg cgc aaa        1344
Gly Val Phe Thr Asp Asp Ala Ile Asp Ala Tyr Ile Glu Leu Arg Lys
        435                 440                 445 gaa gag atg gac cgc gtt cgc atg acg cca cac ccg gtc gag ttc gaa        1392
Glu Glu Met Asp Arg Val Arg Met Thr Pro His Pro Val Glu Phe Glu
    450                 455                 460 ctg tac tac agc gtc taa                                                 1410
Leu Tyr Tyr Ser Val *
465

<210> SEQ ID NO 42
<211> LENGTH: 469
<212> TYPE: PRT
<213> ORGANISM: Artificial Sequence
<220> FEATURE:
<223> OTHER INFORMATION: AGS1 variant amino acid sequence (AGS1M21)

<400> SEQUENCE: 42

Met Ser Ala Glu His Val Leu Thr Met Leu Asn Glu His Glu Val Lys
 1               5                  10                  15

Phe Val Asp Leu Arg Phe Thr Asp Thr Lys Gly Lys Glu Gln His Val
                20                  25                  30

Thr Ile Pro Ala His Gln Val Asn Ala Asp Phe Phe Glu Glu Gly Lys
            35                  40                  45

Met Phe Asp Gly Ser Ser Ile Gly Gly Trp Lys Gly Ile Asn Glu Ser
        50                  55                  60

Asp Met Val Leu Met Pro Asp Ala Ser Thr Ala Val Leu Asp Pro Phe
65                  70                  75                  80

Phe Glu Glu Pro Thr Leu Ile Ile Arg Cys Asp Ile Leu Glu Pro Gly
                85                  90                  95
```

```
Thr Met Gln Gly Tyr Asp Arg Asp Pro Arg Ser Ile Ser Lys Arg Ala
            100                 105                 110

Glu Asp Phe Leu Arg Ser Ser Gly Ile Ala Asp Thr Val Leu Phe Gly
            115                 120                 125

Pro Glu Pro Glu Phe Phe Leu Phe Asp Asp Ile Arg Phe Gly Ser Ser
130                 135                 140

Ile Arg Gly Ser His Val Ala Ile Asp Asp Ile Glu Gly Ala Trp Ser
145                 150                 155                 160

Ser Gly Thr Lys Tyr Asp Arg Gly Asn Lys Gly His Arg Pro Ala Val
                165                 170                 175

Lys Gly Gly Tyr Phe Pro Val Pro Pro Val Asp Ser Ser Gln Asp Leu
            180                 185                 190

Arg Ser Thr Met Cys Leu Thr Met Glu Glu Met Gly Leu Val Val Glu
            195                 200                 205

Ala His His His Glu Met Ala Thr Ala Gly Gln Asn Glu Val Ala Thr
            210                 215                 220

Arg Phe Asn Thr Met Thr Lys Lys Ala Asp Glu Ile Gln Ile Tyr Lys
225                 230                 235                 240

Tyr Val Val His Asn Val Ala His Ala Phe Gly Lys Thr Ala Thr Phe
                245                 250                 255

Met Pro Lys Pro Met Phe Gly Asp Asn Gly Ser Gly Met His Cys His
            260                 265                 270

Met Ser Leu Ser Lys Asn Gly Thr Asn Leu Phe Ala Gly Asp Lys Tyr
            275                 280                 285

Gly Gly Leu Ser Glu Thr Ala Leu Phe Tyr Ile Gly Gly Ile Ile Lys
            290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Ala Ser Pro
            340                 345                 350

Lys Ala Arg Arg Ile Glu Ala Arg Phe Pro Asp Pro Ala Ala Asn Pro
            355                 360                 365

Tyr Leu Cys Phe Ala Ala Leu Leu Met Ala Gly Leu Asp Gly Ile Ile
            370                 375                 380

Asn Lys Ile His Pro Gly Asp Ala Met Asp Lys Asn Leu Tyr Asp Leu
385                 390                 395                 400

Pro Pro Glu Glu Glu Ala Glu Ile Pro Lys Val Ala Gly Ser Leu Asp
                405                 410                 415

Glu Ala Met Ala Ala Leu Asn Glu Asp Arg Glu Phe Leu Thr Arg Gly
            420                 425                 430

Gly Val Phe Thr Asp Asp Ala Ile Asp Ala Tyr Ile Glu Leu Arg Lys
            435                 440                 445

Glu Glu Met Asp Arg Val Arg Met Thr Pro His Pro Val Glu Phe Glu
            450                 455                 460

Leu Tyr Tyr Ser Val
465

<210> SEQ ID NO 43
<211> LENGTH: 1543
<212> TYPE: DNA
<213> ORGANISM: Artificial Sequence
<220> FEATURE:
<223> OTHER INFORMATION: ags1 variant nucleotide sequence (ags1(ad-))
```

```
<221> NAME/KEY: CDS
<222> LOCATION: (1)...(1410)

<400> SEQUENCE: 43 atg tcc gct gaa cac gtt ttg acg atg ctg aat gag cat gaa gtg aaa       48
Met Ser Ala Glu His Val Leu Thr Met Leu Asn Glu His Glu Val Lys
 1               5                  10                  15 ttc gta gac ctg cgt ttc act gac acc aag ggt aag gaa cag cac gtg       96
Phe Val Asp Leu Arg Phe Thr Asp Thr Lys Gly Lys Glu Gln His Val
             20                  25                  30 act atc ccg gct cac cag gta aac gcc gac ttc ttc gaa gaa ggt aaa      144
Thr Ile Pro Ala His Gln Val Asn Ala Asp Phe Phe Glu Glu Gly Lys
         35                  40                  45 atg ttt gac ggc tcc tct atc ggt ggt tgg aag ggc atc aac gaa tct      192
Met Phe Asp Gly Ser Ser Ile Gly Gly Trp Lys Gly Ile Asn Glu Ser
     50                  55                  60 gac atg gtg ctg atg ccg gac gcc agc acg gcg gtt ctg gat ccg ttc      240
Asp Met Val Leu Met Pro Asp Ala Ser Thr Ala Val Leu Asp Pro Phe
 65                  70                  75                  80 ttc gaa gaa cct acg ctg atc att cgc tgt gac att ctc gag ccg ggc      288
Phe Glu Glu Pro Thr Leu Ile Ile Arg Cys Asp Ile Leu Glu Pro Gly
                 85                  90                  95 acc atg caa ggc tac gat cgc gac ccg cgt tcc atc tcc aaa cgc gcc      336
Thr Met Gln Gly Tyr Asp Arg Asp Pro Arg Ser Ile Ser Lys Arg Ala
            100                 105                 110 gaa gac ttc ctg cgc tcc tcc ggc atc gcg gac acc gtg ctg ttc ggg      384
Glu Asp Phe Leu Arg Ser Ser Gly Ile Ala Asp Thr Val Leu Phe Gly
        115                 120                 125 cca gag cct gag ttc ttc ctg ttc gac gac atc cgc ttc ggc agc agc      432
Pro Glu Pro Glu Phe Phe Leu Phe Asp Asp Ile Arg Phe Gly Ser Ser
    130                 135                 140 atc cgc ggt tcc cac gtg gcg atc gac gat atc gaa ggc gcc tgg aac      480
Ile Arg Gly Ser His Val Ala Ile Asp Asp Ile Glu Gly Ala Trp Asn
145                 150                 155                 160 tcc ggc aca aaa tac gac ggc ggc aac aaa ggc cac cgt ccg gcg gtg      528
Ser Gly Thr Lys Tyr Asp Gly Gly Asn Lys Gly His Arg Pro Ala Val
                165                 170                 175 aaa ggc ggt tac ttc ccg gtt cca ccg gtc gac tct tcg cag gat ctg      576
Lys Gly Gly Tyr Phe Pro Val Pro Pro Val Asp Ser Ser Gln Asp Leu
            180                 185                 190 cgt tcc acc atg tgt ctg acc atg gaa gag atg ggc ctg gtg gtt gaa      624
Arg Ser Thr Met Cys Leu Thr Met Glu Glu Met Gly Leu Val Val Glu
        195                 200                 205 gcg cac cac cac gaa gtg gcg acc gcc ggt cag aac gaa gtg gca acc      672
Ala His His His Glu Val Ala Thr Ala Gly Gln Asn Glu Val Ala Thr
    210                 215                 220 cgc ttc aac acc atg acc aag aaa gcc gac gaa att cag atc tat aag      720
Arg Phe Asn Thr Met Thr Lys Lys Ala Asp Glu Ile Gln Ile Tyr Lys
225                 230                 235                 240 tac gtg gtg cac aac gtg gcg cac gcc ttc ggt aaa acc gcg acc ttc      768
Tyr Val Val His Asn Val Ala His Ala Phe Gly Lys Thr Ala Thr Phe
                245                 250                 255 atg ccg aag ccc atg ttc ggc gac aac ggt tcc ggc atg cac tgc cac      816
Met Pro Lys Pro Met Phe Gly Asp Asn Gly Ser Gly Met His Cys His
            260                 265                 270 atg tcg ctg tcc aag aac ggc acc aac ctg ttc gcc ggc gac aaa tac      864
Met Ser Leu Ser Lys Asn Gly Thr Asn Leu Phe Ala Gly Asp Lys Tyr
        275                 280                 285 ggc ggc ctg tct gaa acc gca ctg ttc tac atc ggc ggt atc atc aag      912
Gly Gly Leu Ser Glu Thr Ala Leu Phe Tyr Ile Gly Gly Ile Ile Lys
    290                 295                 300
```

-continued

```
cac gcc aag gcg atc aac gcg ctg gcc aac ccg acc acc aac tcg tac    960
His Ala Lys Ala Ile Asn Ala Leu Ala Asn Pro Thr Thr Asn Ser Tyr
305                 310                 315                 320 aaa cgt ctg gtg cca ggc tac gaa gcg ccg gtg atg ctg gct tac tcc   1008
Lys Arg Leu Val Pro Gly Tyr Glu Ala Pro Val Met Leu Ala Tyr Ser
                325                 330                 335 gcc cgt aac cgc tcc gcg tcc atc cgt atc ccg gtg gtc gcc agc ccg   1056
Ala Arg Asn Arg Ser Ala Ser Ile Arg Ile Pro Val Val Ala Ser Pro
            340                 345                 350 aaa gcg cgc cgc atc gaa gcc cgc ttc ccg gat ccg gcg gct aac cca   1104
Lys Ala Arg Arg Ile Glu Ala Arg Phe Pro Asp Pro Ala Ala Asn Pro
        355                 360                 365 tac ctg tgc ttc gcc gca ctg ctg atg gcc ggc ctg gac ggc atc atc   1152
Tyr Leu Cys Phe Ala Ala Leu Leu Met Ala Gly Leu Asp Gly Ile Ile
    370                 375                 380 aac aag atc cac cct ggc gac gcc atg gac aaa aac ctg ttc gac ctg   1200
Asn Lys Ile His Pro Gly Asp Ala Met Asp Lys Asn Leu Phe Asp Leu
385                 390                 395                 400 ccg ccg gaa gaa gaa gcc gag atc cca aaa gtg gcc ggc tcg ctg gac   1248
Pro Pro Glu Glu Glu Ala Glu Ile Pro Lys Val Ala Gly Ser Leu Asp
                405                 410                 415 gag gcg atg gcc gcg ctg aac gaa gac cgc gag ttc ctg acc cgc ggc   1296
Glu Ala Met Ala Ala Leu Asn Glu Asp Arg Glu Phe Leu Thr Arg Gly
            420                 425                 430 ggc gtg ttc acc gac gat gcg atc gat gcc tac atc gaa ctg cgc aaa   1344
Gly Val Phe Thr Asp Asp Ala Ile Asp Ala Tyr Ile Glu Leu Arg Lys
        435                 440                 445 gaa gag atg gac cgc gtt cgc atg acg cca cac ccg gtc gag ttc gaa   1392
Glu Glu Met Asp Arg Val Arg Met Thr Pro His Pro Val Glu Phe Glu
    450                 455                 460 ctg tac tac agc gtc taa gccctacccg cgccgtctgc aaaggcggac          1440
Leu Tyr Tyr Ser Val  *
465 ggcgcccaca attttctgca ggtcgacaag cttgcggccg cactcgagtc tggtaaagaa  1500 accgctgctg cgaaatttga acgccagcac atggactcgt cta                   1543

<210> SEQ ID NO 44
<211> LENGTH: 469
<212> TYPE: PRT
<213> ORGANISM: Artificial Sequence
<220> FEATURE:
<223> OTHER INFORMATION: AGS1 variant amino acid sequence (AGS1(AD-))

<400> SEQUENCE: 44

Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
            20                  25                  30

Thr Ile Pro Ala His Gln Val Asn Ala Asp Phe Phe Glu Glu Gly Lys
        35                  40                  45

Met Phe Asp Gly Ser Ser Ile Gly Gly Trp Lys Gly Ile Asn Glu Ser
    50                  55                  60

Asp Met Val Leu Met Pro Asp Ala Ser Thr Ala Val Leu Asp Pro Phe
65                  70                  75                  80

Phe Glu Glu Pro Thr Leu Ile Ile Arg Cys Asp Ile Leu Glu Pro Gly
                85                  90                  95

Thr Met Gln Gly Tyr Asp Arg Asp Pro Arg Ser Ile Ser Lys Arg Ala
            100                 105                 110
```

```
Glu Asp Phe Leu Arg Ser Ser Gly Ile Ala Asp Thr Val Leu Phe Gly
            115                 120                 125
Pro Glu Pro Glu Phe Phe Leu Phe Asp Asp Ile Arg Phe Gly Ser Ser
        130                 135                 140
Ile Arg Gly Ser His Val Ala Ile Asp Asp Ile Glu Gly Ala Trp Asn
145                 150                 155                 160
Ser Gly Thr Lys Tyr Asp Gly Gly Asn Lys Gly His Arg Pro Ala Val
                165                 170                 175
Lys Gly Gly Tyr Phe Pro Val Pro Val Asp Ser Ser Gln Asp Leu
                180                 185                 190
Arg Ser Thr Met Cys Leu Thr Met Glu Glu Met Gly Leu Val Val Glu
            195                 200                 205
Ala His His Glu Val Ala Thr Ala Gly Gln Asn Glu Val Ala Thr
        210                 215                 220
Arg Phe Asn Thr Met Thr Lys Lys Ala Asp Glu Ile Gln Ile Tyr Lys
225                 230                 235                 240
Tyr Val Val His Asn Val Ala His Ala Phe Gly Lys Thr Ala Thr Phe
                245                 250                 255
Met Pro Lys Pro Met Phe Gly Asp Asn Gly Ser Gly Met His Cys His
                260                 265                 270
Met Ser Leu Ser Lys Asn Gly Thr Asn Leu Phe Ala Gly Asp Lys Tyr
            275                 280                 285
Gly Gly Leu Ser Glu Thr Ala Leu Phe Tyr Ile Gly Ile Ile Lys
        290                 295                 300
His Ala Lys Ala Ile Asn Ala Leu Ala Asn Pro Thr Thr Asn Ser Tyr
305                 310                 315                 320
Lys Arg Leu Val Pro Gly Tyr Glu Ala Pro Val Met Leu Ala Tyr Ser
                325                 330                 335
Ala Arg Asn Arg Ser Ala Ser Ile Arg Ile Pro Val Val Ala Ser Pro
            340                 345                 350
Lys Ala Arg Arg Ile Glu Ala Arg Phe Pro Asp Pro Ala Ala Asn Pro
        355                 360                 365
Tyr Leu Cys Phe Ala Ala Leu Leu Met Ala Gly Leu Asp Gly Ile Ile
370                 375                 380
Asn Lys Ile His Pro Gly Asp Ala Met Asp Lys Asn Leu Phe Asp Leu
385                 390                 395                 400
Pro Pro Glu Glu Glu Ala Glu Ile Pro Lys Val Ala Gly Ser Leu Asp
                405                 410                 415
Glu Ala Met Ala Ala Leu Asn Glu Asp Arg Glu Phe Leu Thr Arg Gly
            420                 425                 430
Gly Val Phe Thr Asp Asp Ala Ile Asp Ala Tyr Ile Glu Leu Arg Lys
        435                 440                 445
Glu Glu Met Asp Arg Val Arg Met Thr Pro His Pro Val Glu Phe Glu
    450                 455                 460
Leu Tyr Tyr Ser Val
465

<210> SEQ ID NO 45
<211> LENGTH: 1410
<212> TYPE: DNA
<213> ORGANISM: Artificial Sequence
<220> FEATURE:
<223> OTHER INFORMATION: ags1 variant nucleotide sequence
      (ags1m17(ad-))
<221> NAME/KEY: CDS
<222> LOCATION: (1)...(1410)
```

<400> SEQUENCE: 45

```
atg tcc gct gaa cac gtt ttg acg atg ctg aat gag cat gaa gtg aaa     48
Met Ser Ala Glu His Val Leu Thr Met Leu Asn Glu His Glu Val Lys
1               5                   10                  15 ttc gta gac ctg cgt ttc act gac acc aag ggt aag gaa cag cac gtg     96
Phe Val Asp Leu Arg Phe Thr Asp Thr Lys Gly Lys Glu Gln His Val
            20                  25                  30 act atc ccg gct cac cag gta aac gcc gac ttc ttc gaa gaa ggt aaa    144
Thr Ile Pro Ala His Gln Val Asn Ala Asp Phe Phe Glu Glu Gly Lys
        35                  40                  45 atg ttt gac ggc tcc tct atc ggt ggt tgg aag ggc atc aac gaa tct    192
Met Phe Asp Gly Ser Ser Ile Gly Gly Trp Lys Gly Ile Asn Glu Ser
    50                  55                  60 gac atg gtg ctg atg ccg gac gcc agc acg gcg gtt ctg gat ccg ttc    240
Asp Met Val Leu Met Pro Asp Ala Ser Thr Ala Val Leu Asp Pro Phe
65                  70                  75                  80 tcc gaa gaa cct acg ctg atc att cgc tgt gac atc ctc gag ccg ggc    288
Ser Glu Glu Pro Thr Leu Ile Ile Arg Cys Asp Ile Leu Glu Pro Gly
                85                  90                  95 acc atg caa ggc tac gat cgc gac ccg cgt tcc atc tcc aaa cgc gcc    336
Thr Met Gln Gly Tyr Asp Arg Asp Pro Arg Ser Ile Ser Lys Arg Ala
            100                 105                 110 gaa gac ttc ctg cgc tcc tcc ggc atc gcg gac acc gtg ctg ttc ggg    384
Glu Asp Phe Leu Arg Ser Ser Gly Ile Ala Asp Thr Val Leu Phe Gly
        115                 120                 125 cca gag cct gag ttc ttc ctg ttc gac gac atc cgc ttc ggc agc agc    432
Pro Glu Pro Glu Phe Phe Leu Phe Asp Asp Ile Arg Phe Gly Ser Ser
    130                 135                 140 atc cgc ggt tcc cac gtg gcg atc gac gat atc gaa ggc gcc tgg aac    480
Ile Arg Gly Ser His Val Ala Ile Asp Asp Ile Glu Gly Ala Trp Asn
145                 150                 155                 160 tcc ggc aca aaa tac gac ggc ggc aac aaa ggc cac cgt ccg gcg gtg    528
Ser Gly Thr Lys Tyr Asp Gly Gly Asn Lys Gly His Arg Pro Ala Val
                165                 170                 175 aaa ggc ggt tac ttc ccg gtt cca tcg gtc gac tct tcg cag gat ctg    576
Lys Gly Gly Tyr Phe Pro Val Pro Ser Val Asp Ser Ser Gln Asp Leu
            180                 185                 190 cgt tcc acc atg tgt ctg acc atg gaa gag atg ggc ctg gtg gtt gaa    624
Arg Ser Thr Met Cys Leu Thr Met Glu Glu Met Gly Leu Val Val Glu
        195                 200                 205 gcg cac cac acc gag gca gcg acc gct agc cag aac gaa gtg gca acc    672
Ala His His Thr Glu Ala Ala Thr Ala Ser Gln Asn Glu Val Ala Thr
    210                 215                 220 cgc ttc aac acc atg acc aag aaa gcc gac gaa att cag atc tat aag    720
Arg Phe Asn Thr Met Thr Lys Lys Ala Asp Glu Ile Gln Ile Tyr Lys
225                 230                 235                 240 tac gtg gtg cac aac gtg gca cac gcc ttc ggt aaa acc gcg acc ttc    768
Tyr Val Val His Asn Val Ala His Ala Phe Gly Lys Thr Ala Thr Phe
                245                 250                 255 atg ccg aag ccc atg ttc ggc gac aac ggt tcc ggc atg cac tgc cac    816
Met Pro Lys Pro Met Phe Gly Asp Asn Gly Ser Gly Met His Cys His
            260                 265                 270 atg tcg ctg tcc aag aac ggc acc aac ctg ttc gcc ggc gac aaa tac    864
Met Ser Leu Ser Lys Asn Gly Thr Asn Leu Phe Ala Gly Asp Lys Tyr
        275                 280                 285 ggc ggc ctg tct gaa acc gca ctg ttc tac atc ggt ggt atc aac aag    912
Gly Gly Leu Ser Glu Thr Ala Leu Phe Tyr Ile Gly Gly Ile Asn Lys
    290                 295                 300 cac gcc aag gcg atc aac gcg ctg gcc aac ccg acc acc aac tcg tac    960
His Ala Lys Ala Ile Asn Ala Leu Ala Asn Pro Thr Thr Asn Ser Tyr
```

```
                305                 310                 315                 320
aaa cgt ctg gtg cca ggc tac gaa gcg ccg gtg atg ctg gct tac tcc         1008
Lys Arg Leu Val Pro Gly Tyr Glu Ala Pro Val Met Leu Ala Tyr Ser
            325                 330                 335 gcc cgt aac cgc tcc gcg tcc atc cgt atc ccg gtg gtc gcc agc ccg         1056
Ala Arg Asn Arg Ser Ala Ser Ile Arg Ile Pro Val Val Ala Ser Pro
        340                 345                 350 aaa gcg cgc cgc atc gaa gcc cgc ttc ccg gat ccg gcg gct aac cca         1104
Lys Ala Arg Arg Ile Glu Ala Arg Phe Pro Asp Pro Ala Ala Asn Pro
    355                 360                 365 tac ctg tgc ttc gcc gca ctg ctg atg gcc ggc ctg gac ggc atc atc         1152
Tyr Leu Cys Phe Ala Ala Leu Leu Met Ala Gly Leu Asp Gly Ile Ile
370                 375                 380 aac aag atc cac cct ggc gac gcc atg gac aaa aac ctg ttc gac ctg         1200
Asn Lys Ile His Pro Gly Asp Ala Met Asp Lys Asn Leu Phe Asp Leu
385                 390                 395                 400 ccg ccg gaa gaa gaa gcc gag atc cca aaa gtg gcc ggc tcg ctg gac         1248
Pro Pro Glu Glu Glu Ala Glu Ile Pro Lys Val Ala Gly Ser Leu Asp
                405                 410                 415 gag gcg atg gcc gcg ctg aac gaa gac cgc gag ttc ctg acc cgc ggc         1296
Glu Ala Met Ala Ala Leu Asn Glu Asp Arg Glu Phe Leu Thr Arg Gly
            420                 425                 430 ggc gtg ttc act gac gat gcg atc gat gcc tac atc gaa ctg cgc aaa         1344
Gly Val Phe Thr Asp Asp Ala Ile Asp Ala Tyr Ile Glu Leu Arg Lys
        435                 440                 445 gaa gag atg gac cgc gtt cgc atg acg cca cac ccg gtc gag ttc gaa         1392
Glu Glu Met Asp Arg Val Arg Met Thr Pro His Pro Val Glu Phe Glu
    450                 455                 460 ctg tac tac agc gtc taa                                                 1410
Leu Tyr Tyr Ser Val *
465

<210> SEQ ID NO 46
<211> LENGTH: 469
<212> TYPE: PRT
<213> ORGANISM: Artificial Sequence
<220> FEATURE:
<223> OTHER INFORMATION: AGS1 variant amino acid sequence
      (AGS1M17(AD-))

<400> SEQUENCE: 46

Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
            20                  25                  30

Thr Ile Pro Ala His Gln Val Asn Ala Asp Phe Phe Glu Glu Gly Lys
        35                  40                  45

Met Phe Asp Gly Ser Ser Ile Gly Gly Trp Lys Gly Ile Asn Glu Ser
    50                  55                  60

Asp Met Val Leu Met Pro Asp Ala Ser Thr Ala Val Leu Asp Pro Phe
65                  70                  75                  80

Ser Glu Glu Pro Thr Leu Ile Ile Arg Cys Asp Ile Leu Glu Pro Gly
                85                  90                  95

Thr Met Gln Gly Tyr Asp Arg Asp Pro Arg Ser Ile Ser Lys Arg Ala
            100                 105                 110

Glu Asp Phe Leu Arg Ser Ser Gly Ile Ala Asp Thr Val Leu Phe Gly
        115                 120                 125

Pro Glu Pro Glu Phe Phe Leu Phe Asp Asp Ile Arg Phe Gly Ser Ser
    130                 135                 140
```

```
Ile Arg Gly Ser His Val Ala Ile Asp Asp Ile Glu Gly Ala Trp Asn
145                 150                 155                 160

Ser Gly Thr Lys Tyr Asp Gly Asn Lys Gly His Arg Pro Ala Val
            165                 170                 175

Lys Gly Gly Tyr Phe Pro Val Pro Ser Val Asp Ser Ser Gln Asp Leu
                180                 185                 190

Arg Ser Thr Met Cys Leu Thr Met Glu Glu Met Gly Leu Val Val Glu
            195                 200                 205

Ala His His Thr Glu Ala Ala Thr Ala Ser Gln Asn Glu Val Ala Thr
        210                 215                 220

Arg Phe Asn Thr Met Thr Lys Lys Ala Asp Glu Ile Gln Ile Tyr Lys
225                 230                 235                 240

Tyr Val Val His Asn Val Ala His Ala Phe Gly Lys Thr Ala Thr Phe
                245                 250                 255

Met Pro Lys Pro Met Phe Gly Asp Asn Gly Ser Gly Met His Cys His
                260                 265                 270

Met Ser Leu Ser Lys Asn Gly Thr Asn Leu Phe Ala Gly Asp Lys Tyr
            275                 280                 285

Gly Gly Leu Ser Glu Thr Ala Leu Phe Tyr Ile Gly Gly Ile Asn Lys
        290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Ala Ser Pro
                340                 345                 350

Lys Ala Arg Arg Ile Glu Ala Arg Phe Pro Asp Pro Ala Ala Asn Pro
            355                 360                 365

Tyr Leu Cys Phe Ala Ala Leu Leu Met Ala Gly Leu Asp Gly Ile Ile
        370                 375                 380

Asn Lys Ile His Pro Gly Asp Ala Met Asp Lys Asn Leu Phe Asp Leu
385                 390                 395                 400

Pro Pro Glu Glu Glu Ala Glu Ile Pro Lys Val Ala Gly Ser Leu Asp
                405                 410                 415

Glu Ala Met Ala Ala Leu Asn Glu Asp Arg Glu Phe Leu Thr Arg Gly
            420                 425                 430

Gly Val Phe Thr Asp Asp Ala Ile Asp Ala Tyr Ile Glu Leu Arg Lys
        435                 440                 445

Glu Glu Met Asp Arg Val Arg Met Thr Pro His Pro Val Glu Phe Glu
450                 455                 460

Leu Tyr Tyr Ser Val
465

<210> SEQ ID NO 47
<211> LENGTH: 1410
<212> TYPE: DNA
<213> ORGANISM: Artificial Sequence
<220> FEATURE:
<223> OTHER INFORMATION: synthetic nucleotide sequence encoding
      AGS1M16 (synags1m16)

<400> SEQUENCE: 47
atgtcagcag agcatgtgct caccatgctg aatgagcatg aggtgaagtt cgtggacctc    60
cgcttcaccg acaccaaggg caaggagcag catgtcacca tccctgctca tcaagtcaac   120
gccgacttct ttgaagaagg caagatgttt gatggaagct caattggagg atggaagggc   180
```

```
atcaatgaga gcgacatggt gctgatgcca gatgcttcga cggcggtgct ggacccttc    240 tcagaagaac caacattgat catcagatgt gacatcctgg agcctggcac catgcaaggc    300
tatgatcgag atccaagaag catcagcaag cgcgccgagg acttcttgag gagcagcggc    360
atcgccgaca ccgtgctctt cgggccggag ccggagttct tcctcttcga cgacatcaga    420
tttggatcaa gcatcagagg aagtcatgtg gccatcgacg acattgaagg agcatggaac    480
agcggcacca agtacgacgg cggcaacaag ggccaccggc cggcggtgaa gggcggctac    540
ttcccggtgc cgtcggtgga cagcagccaa gatttgagga gcaccatgtg cctcacaatg    600
gaggagatgg ggctggtggt ggaagctcat cacaacgagg tggcgacggc atcacaaaat    660
gaggtggcaa caaggttcaa caccatgacc aagaaggctg atgagatcca gatctacaag    720
tatgtggtgc acaatgttgc tcatgccttc ggcaagacgg ccaccttcat gcccaagcca    780
atgttcggcg acaatggaag cggcatgcac tgccacatga gcttgagcaa gaatggcacc    840
aacctatttg ctggagacaa gtacggcggc ctttctgaga cggcgctctt ctacatcggc    900
ggcatcaaca agcatgccaa ggccatcaac gcgctggcca accccaccac caacagctac    960
aagaggctgg tgcctggata tgaggcgccg gtgatgctgg catattcagc aaggaacagg   1020
agcgcctcca tcaggattcc tgtggtggcc tcgcccaagg caagaagaat tgaagcaaga   1080
tttccagatc ccgccgccaa cccttattta tgcttcgccg cgctgctgat ggccggcctg   1140
gatggcatca tcaacaagat ccatcctgga gatgcaatgg acaagaacct ctacgacctg   1200
ccgccagaag aagaagctga gatccccaag gtggctggat cattggatga agcaatggcg   1260
gcgctcaatg aagatcgaga gttcctcacc cgcggcggcg tcttcactga tgatgccatc   1320
gacgcctaca tcgagctgag gaaggaggag atggacaggg tgaggatgac gccgcacccg   1380
gtggagtttg agctctacta ctccgtgtaa                                    1410
```

BACTERIAL GLUTAMINE SYNTHETASES AND METHODS OF USE

CROSS REFERENCE TO RELATED APPLICATION

This application claims the benefit of U.S. Provisional Application Ser. No. 60/812,000, filed Jun. 8, 2006, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "329217_SequenceListing.txt", created on Jun. 4, 2007, and having a size of 229,348 bytes and is filed concurrently with the specification. The sequence listing contained in this ASCII formatted document is part of the specification and is herein incorporated by reference in its entirety.

FIELD OF THE INVENTION

This invention relates to plant molecular biology, particularly to a novel class of glutamine synthetase enzymes that confer resistance to herbicidal glutamine synthetase inhibitors.

BACKGROUND OF THE INVENTION

Plants obtain nitrogen from their environment in the form of inorganic compounds, namely nitrate and ammonia taken up from roots, and atmospheric $N_2$ reduced to ammonia in nitrogen-fixing root nodules. The first step in the assimilation of inorganic nitrogen into organic form predominately involves the incorporation of ammonia with glutamate to form glutamine, catalyzed by the enzyme glutamine synthetase.

Several herbicides function by inhibiting plant glutamine synthetase. A typical example of such compound is the glutamic acid analogue, glufosinate (or phosphinothricin). Many of these herbicides inhibit glutamine synthetase present in the crop plants as well as in weeds, thereby limiting the use of such compounds as glufosinate. Since herbicidal selectivity is important in any commercially useful herbicide, it would be of great interest to be able to confer resistance in selected plants to such non-selective herbicides as glufosinate, as well as to other herbicidal glutamine synthetase inhibitors.

Enzymes that are resistant to herbicidal glutamine synthetase inhibitors are known in the art. Methione sulfoximine (MSO), a glutamate analog, is a mixed competitive inhibitor of pea leaf glutamine synthetase (Leason et al. (1982) *Phytochemistry* 21:855). Phosphinothricin-resistant alfalfa cells have been reported (Newmark (1983) *Nature* 305:383-384). The resistance was due to amplification of the glutamine synthetase gene (Donn et al. (1984) *Journal of Molecular and Applied Genetics* 2: 621-635). The Bar gene, isolated from *Streptomyces hygroscopicus*, codes for the enzyme phosphinothricin N-acetyltransferase (PAT). This gene can confer resistance to glufosinate herbicides in that PAT detoxifies phosphinothricin by acetylation, which produces an inactive compound.

Additional genes that are resistant to herbicidal glutamine synthetase inhibitors are needed where the resistance is due to a functional mutation in the glutamine synthetase enzyme, rather than an amplification or inactivation by acetylation of the enzyme.

SUMMARY OF INVENTION

Compositions and methods for conferring resistance to herbicidal glutamine synthetase inhibitors in plants, plant cells, tissues and seeds are provided. In one embodiment, the polynucleotides employed in the various methods and compositions confer resistance to glufosinate. Compositions include polynucleotides encoding polypeptides resistant to herbicidal glutamine synthetase inhibitors, vectors comprising those polynucleotides, and host cells comprising the vectors. Compositions comprising a coding sequence for a polypeptide that confers resistance or tolerance to herbicidal glutamine synthetase inhibitors are provided. Compositions comprising a coding sequence for a polypeptide that results in improved nitrogen utilization and/or enhanced yield in a plant are further provided. The coding sequences can be used in DNA constructs or expression cassettes for transformation and expression in organisms, including microorganisms and plants. Compositions also comprise transformed bacteria, plants, plant cells, tissues, and seeds.

The present invention provides for isolated polynucleotides comprising SEQ ID NO:1, as well as variants of the polynucleotide sequence set forth in SEQ ID NO:1, including SEQ ID NOS:3, 5, 7, 9, 11, 13, 15, 17, 19, 21, 23, 25, 27, 29, 31, 33, 35, 37, 39, 41, 43, 45, 47, or the glutamine synthetase nucleotide sequence deposited in a bacterial host as Accession No. NRRL B-30930, and the polypeptides corresponding to those polynucleotides. In one embodiment, the polynucleotides of the present invention comprise at least one modification between amino acids 125 to 175 or between amino acids 200 to 250 corresponding to SEQ ID NO:2, or at least one modification that results in the loss of an adenylylation site.

DESCRIPTION OF FIGURES

FIGS. 1A-1C show an alignment of the nucleotide sequence of the herbicide-resistant variants of glutamine synthetase, including pAX3421m1 (SEQ ID NO:4), pAX3422m2 (SEQ ID NO:6), pAX3427m3 (SEQ ID NO:8), pAX3428m4 (SEQ ID NO:10), pAX3430m6 (SEQ ID NO:12), pAX3431m7 (SEQ ID NO:14), pAX3432m8 (SEQ ID NO:16), pAX3433m9 (SEQ ID NO:18), pAX3434m10 (SEQ ID NO:20), pAX3435m11 (SEQ ID NO:22), pAX3436m12 (SEQ ID NO:24), pAX3437m13 (SEQ ID NO:26), pAX3438m14 (SEQ ID NO:28), pAX3426m15 (SEQ ID NO:30) and pAX3439m16 (SEQ ID NO:32) with the wild-type ags1 amino acid sequence (SEQ ID NO:2).

DETAILED DESCRIPTION OF THE INVENTION

I. Compositions

Compositions and methods for conferring herbicide resistance or tolerance, particularly resistance or tolerance to herbicidal glutamine synthetase inhibitors, in organisms are provided. The methods involve transforming organisms with polynucleotides encoding an herbicide tolerance gene that encodes a polypeptide that is resistant to herbicidal glutamine synthetase inhibitors. In one embodiment, the polynucleotides encode an herbicide tolerance gene that encodes a polypeptide that is resistant to inhibition by glufosinate. By "herbicidal resistance" or "herbicidal tolerance" gene of the invention is intended the nucleotide sequence set forth in SEQ ID NO: 3, 5, 7, 9, 11, 13, 15, 17, 19, 21, 23, 25, 27, 29, 31, 33, 35, 37, 39, 41, 43, 45, or 47 and fragments and variants thereof that encode a glutamine synthetase inhibitor (GS inhibitor) resistance or tolerance polypeptide. Likewise, a "herbicidal resistance" or "herbicidal tolerance" polypeptide of the invention is a polypeptide having the amino acid sequence set forth in SEQ ID NO: 4, 6, 8, 10, 12, 14, 16, 18, 20, 22, 24, 26, 28, 30, 32, 34, 36, 38, 40, 42, 44, 46, and fragments and variants thereof, that confer GS-inhibitor resistance or tolerance to a host cell.

The present invention provides for isolated polynucleotides comprising variants of the polynucleotide sequence set forth in SEQ ID NO:1, wherein the variants encode polypeptides that are resistant to herbicidal glutamine synthetase inhibitors. In one embodiment, the polynucleotides of the present invention encode polypeptides that comprise at least one modification between amino acids 125 to 175 or at least one modification between amino acids 200 to 250 corresponding to SEQ ID NO:2. For the purposes of the present invention, "modification" is intended a change in the nucleotide sequence that results in a change in the encoded polypeptide. A modification can also encompass a substitution of one amino acid for another amino acid in a polypeptide sequence. By "corresponding to" is intended that the recited amino acid positions relate to the amino acid positions designated in SEQ ID NO:2, and that substitutions corresponding to these amino acid positions may be found in variant sequences when these variant sequences are aligned with SEQ ID NO:2 using standard alignment methods.

A plasmid containing the herbicide resistance nucleotide sequence of the invention was deposited in the permanent collection of the Agricultural Research Service Culture Collection, Northern Regional Research Laboratory (NRRL), 1815 North University Street, Peoria, Ill. 61604, United States of America, on Jun. 8, 2006, and assigned Accession No. B-30930. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The definition of the enzyme "glutamine synthetase," or "glutamine synthase" is functional and includes any glutamine synthetase capable of functioning in a given desired host, especially a bacterium or plant, to convert glutamic acid to glutamine. The term therefore includes not only the enzyme from the specific plant species involved in the transformation, but may include glutamine synthetase from other plant species or microbes, if such glutamine synthetase is capable of functioning in the transformed plant or bacterial cells.

The term "herbicidal glutamine synthetase inhibitor" or "herbicidal glutamine synthase inhibitor" is meant to include any inhibitor, competitive or noncompetitive, that significantly decreases the glutamine synthetase activity of a plant cell of a given species and, as a consequence thereof, causes herbicidal effects in the plant cell. Examples of glutamine synthetase inhibitors are glufosinate, phosphinothricin, methionine sulfoximine, as well as other glutamic acid analogs.

The term "glufosinate" denotes the known compound, in its biologically active form. It may be present in any enantomeric form, and may be alone or in combination with other inert or active compounds which do not interfere with glufosinate activity.

A. Glutamine Synthetase

In the present invention, the class of enzymes that confers herbicide resistance is glutamine synthetase (GS). The term "glutamine synthetase" or "glutamine synthase" or "GS" as used herein refers to both a native glutamine synthetase or a variant or fragment thereof.

Glutamine synthetase is a key enzyme in nitrogen metabolism; it has dual functions in two essential biochemical reactions, ammonia assimilation and glutamine biosynthesis. Glutamine produced by GS is essential for protein synthesis, and its amide nitrogen is donated to synthesize many essential metabolites.

The common form of GS is a dodecameric enzyme with identical subunits of approximately 55 kDa, encoded by glnA. The crystal structure of this enzyme revealed that it is composed of 12 identical subunits arranged as two superimposed hexagonal rings that are held together by both hydrophobic interactions and hydrogen bonding between the subunits. (Yamashita et al. (1989) *J. Biol. Chem.* 264:17681-17690).

Glutamine synthetase catalyzes the formation of glutamine from glutamate and ammonia in an ATP-dependent reaction. It also catalyzes gamma-glutamyl transfer from glutamine to hydroxylamine yielding gamma-glutamylhydroxymate (Stadtman et al. (1974) in *The Enzymes* (Boyer, ed.) 3:755-807 (Academic Press, New York). The catalysis of glutamine synthetase involves the initial formation of a gamma-glutamyl phosphate intermediate, followed by the displacement of the activated phosphate group by ammonia through the formation of a phosphorylated tetrahedral intermediate. In *E. coli*, the highly conserved residues Asp50 and Glu327 form a negatively charged binding pocket that constitutes the ammonia binding site (Liaw et al. (1995) *Protein Sci.* 4:2358-2365).

A number of potent inhibitors are known for glutamine synthetase that mimic the geometry of the tetrahedral intermediate, including glufosinate (or phosphinothricin (PPT)) and L-methionine-DL-sulfoximide (MSX). The phosphorylation of MSX and glufosinate is similar to the phosphorylation of glutamate in the first step of the normal enzymatic reaction of glutamine synthetase, and is required for irreversible inhibition to occur (Crespo et al. (1999) *Eur. J. Biochem.* 266:1202-1209). In plants, inhibition of glutamine synthetase results in a buildup of phytotoxic ammonia and a lack of essential amino acids, and an inhibition of photorespiration and photosynthesis, and, ultimately, plant death.

Glufosinate is a natural compound isolated from two species of *Streptomyces* fungi that inhibits the activity of glutamine synthetase. The application of glufosinate results in reduced glutamine levels and a corresponding increase in concentrations of ammonia in plant tissues, leading to cell membrane disruption and cessation of photosynthesis, resulting in plant withering and death. A number of analogues of glufosinate that inhibit plant glutamine synthetase are known in the art. See, for example, Berlicki et al. (2005) *J. Med. Chem.* 48(20):6340-6349 and Forlani et al. (2006) *J. Agric. Food Chem.* 54(3):796-802, each of which are herein incorporated by reference in their entirety.

B. Herbicide-Resistant Glutamine Synthetase

Resistance to L-phosphinothricin has been reported in alfalfa cells, after a stepwise selection on growing levels of L-PPT, resulting in gene amplification (Donn et al. (1984) *J. Mol. Appl. Genet.* 2:621), and by introgression in tobacco, potato and tomato plants, via *Agrobacterium*-mediated transformation of the Bar gene, which encodes for phosphinotricine acetyltransferase (PAT), a detoxifying enzyme (De Block et al. (1987) *EMBO J.* 6:2513). Mutants of plant glutamine synthetase enzymes that are resistant to phosphinothricin are described in U.S. Pat. No. 5,145,777. These mutants confer resistance by the overexpression of glutamine synthetase.

C. Activity of Glutamine Synthetase

A variety of methods can be used to measure glutamine synthetase activity. See, for example, Crespo et al. (1999) *Eur. J. Biochem.* 266:1202-1209, Gawronski et al. (2004) *Anal. Biochem.* 327:114-118, and U.S. Pat. Nos. 5,098,838 and 5,145,777, each of which are herein incorporated by reference in their entirety. Activity can be measured using purified glutamine synthetase polypeptides, or by testing the ability of organisms transformed with the polynucleotides of the invention to grow in the presence of herbicidal glutamine synthetase inhibitors.

D. Isolated Polynucleotides, and Variants and Fragments Thereof.

In some embodiments, the present invention comprises isolated or recombinant polynucleotides encoding polypeptides that are resistant to herbicidal glutamine synthetase inhibitors. An "isolated" or "purified" polynucleotide or polypeptide, or biologically active portion thereof, is substantially free of other cellular material, or culture medium when produced by recombinant techniques, or substantially free of chemical precursors or other chemicals when chemically synthesized. By "biologically active" is intended to possess the desired biological activity of the native polypeptide, that is, resistance to herbicidal glutamine synthetase inhibitors. An "isolated" polynucleotide may be free of sequences (for example, protein encoding sequences) that naturally flank the nucleic acid (i.e., sequences located at the 5' and 3' ends of the nucleic acid) in the genomic DNA of the organism from which the polynucleotide is derived. For purposes of the invention, "isolated" when used to refer to polynucleotides excludes isolated chromosomes. For example, in various embodiments, the isolated glyphosate resistance-encoding polynucleotide can contain less than about 5 kb, 4 kb, 3 kb, 2 kb, 1 kb, 0.5 kb, or 0.1 kb of nucleotide sequence that naturally flanks the polynucleotide in genomic DNA of the cell from which the polynucleotide is derived.

The present invention further contemplates variants and fragments of the polynucleotides described herein. A "fragment" of a polynucleotide may encode a biologically active portion of a polypeptide, or it may be a fragment that can be used as a hybridization probe or PCR primer using methods disclosed elsewhere herein. Polynucleotides that are fragments of a polynucleotide comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400 contiguous nucleotides, or up to the number of nucleotides present in a full-length polynucleotide disclosed herein. By "contiguous" nucleotides is intended nucleotide residues that are immediately adjacent to one another.

Fragments of the polynucleotides of the present invention generally will encode polypeptide fragments that retain the biological activity of the full-length herbicide resistance protein; i.e., resistance to herbicidal glutamine synthetase inhibitors. By "retains herbicide resistance activity" is intended that the fragment will have at least about 30%, at least about 50%, at least about 70%, or at least about 80% of the herbicide resistance activity of the full-length herbicide resistance protein disclosed herein as SEQ ID NO:6. Methods for measuring herbicide resistance activity are well known in the art. See, for example, U.S. Pat. Nos. 5,098,838 and 5,145,777, each of which are herein incorporated by reference in their entirety. Activity can also refer to the enzymatic activity of the glutamine synthetase enzyme as described elsewhere herein.

A fragment of a polynucleotide that encodes a biologically active portion of a polypeptide of the invention will encode at least about 15, 25, 30, 50, 75, 100, 125, 150, 175, 200, 250, 300, 350, 400, 450 contiguous amino acids, or up to the total number of amino acids present in a full-length polypeptide of the invention.

The invention also encompasses variant polynucleotides. "Variants" of the polynucleotide include those sequences that encode the polypeptides disclosed herein but that differ conservatively because of the degeneracy of the genetic code, as well as those that are sufficiently identical. The term "sufficiently identical" is intended a polypeptide or polynucleotide sequence that has at least about 60% or 65% sequence identity, about 70% or 75% sequence identity, about 80% or 85% sequence identity, about 90%, 91%, 92%, 93%, 94%, 95%, 96%, 97%, 98% or 99% sequence identity compared to a reference sequence using one of the alignment programs using standard parameters. One of skill in the art will recognize that these values can be appropriately adjusted to determine corresponding identity of polypeptides encoded by two polynucleotides by taking into account codon degeneracy, amino acid similarity, reading frame positioning, and the like.

To determine the percent identity of two amino acid sequences or of two polynucleotides, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain polynucleotides homologous to herbicide resistance-encoding polynucleotides used in methods of the invention. BLAST polypeptide searches can be performed with the BLASTX program, score=50, wordlength=3, to obtain amino acid sequences homologous to polypeptide molecules expressed using the methods of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. See www.ncbi.nlm.nih.gov. Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple polypeptides. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453 is used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

Naturally occurring allelic variants can be identified with the use of well-known molecular biology techniques, such as polymerase chain reaction (PCR) and hybridization techniques as outlined below. Variant polynucleotides also include synthetically derived polynucleotides that have been generated, for example, by using site-directed mutagenesis but which still encode the polypeptide having the desired biological activity.

The skilled artisan will further appreciate that changes can be introduced by mutation into the polynucleotides of the invention thereby leading to changes in the amino acid sequence of the encoded polypeptides, without altering the biological activity of the polypeptides. Thus, variant isolated polynucleotides can be created by introducing one or more nucleotide substitutions, additions, or deletions into the corresponding polynucleotide disclosed herein, such that one or more amino acid substitutions, additions or deletions are introduced into the encoded polypeptide. Mutations can be introduced by standard techniques, such as site-directed mutagenesis and PCR-mediated mutagenesis, or gene shuffling techniques. Such variant polynucleotides are also encompassed by the present invention.

Variant polynucleotides can be made by introducing mutations randomly along all or part of the coding sequence, such as by saturation mutagenesis, and the resultant mutants can be screened for the ability to confer herbicide resistance activity to identify mutants that retain activity. Following mutagenesis, the encoded polypeptide can be expressed recombinantly, and the activity of the polypeptide can be determined using standard assay techniques.

Gene shuffling or sexual PCR procedures (for example, Smith (1994) *Nature* 370:324-325; U.S. Pat. Nos. 5,837,458; 5,830,721; 5,811,238; and 5,733,731, each of which is herein incorporated by reference) can be used to identify additional polynucleotides that encode polypeptides that perform similar functions as those described herein (for example, polypeptides that are resistant to herbicidal glutamine synthetase inhibitors). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in different clones becoming mixed and accumulating in some of the resulting sequences. Multiple cycles of selection and shuffling have led to the functional enhancement of several enzymes (Stemmer (1994) *Nature* 370:389-391; Stemmer (1994) *Proc. Natl. Acad. Sci. USA* 91:10747-10751; Crameri et al. (1996) *Nat. Biotechnol.* 14:315-319; Zhang et al. (1997) *Proc. Natl. Acad. Sci. USA* 94:4504-4509; and Crameri et al. (1997) *Nat. Biotechnol.* 15:436-438). Permutational mutagenesis strategies can also be performed. See, for example, U.S. Provisional Application No. 60/813,095, filed Jun. 13, 2006, herein incorporated by reference in its entirety. Such procedures could be performed, for example, on polynucleotides encoding polypeptides that are resistant to herbicidal glutamine synthetase inhibitors.

In a hybridization method, all or part of the herbicide resistance polynucleotide sequence or a sequence encoding a domain of the invention can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known herbicide resistance-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, 200, 250, 300, 350, 400, 500, 600, 700, 800, 900, 1000, 1200, or 1400 consecutive nucleotides of the herbicide resistance-encoding polynucleotide of the invention or a fragment or variant thereof. Methods for the preparation of probes for hybridization are generally known in the art and are disclosed in Sambrook and Russell (2001) supra, and Sambrook et al. (1989) *Molecular Cloning: A Laboratory Manual* (2d ed., Cold Spring Harbor Laboratory Press, Cold Spring Harbor, N.Y.), both of which are herein incorporated by reference.

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, or less than about 500 nucleotides in length.

Stringent conditions may be those in which the salt concentration is less than about 1.5 M Na ion, or about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the polynucleotide sequence, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash conditions, and desired $T_m$, those of ordinary skill in the art will understand that variations in the stringency of hybridization and/or wash solutions are inherently described. If the desired degree of mismatching results in a $T_m$ of less than 45° C. (aqueous solution) or 32° C. (formamide solution), the SSC concentration can be increased so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

E. Isolated Proteins and Variants and Fragments Thereof

Herbicide resistance polypeptides are also encompassed within the present invention. An herbicide resistance polypeptide that is substantially free of cellular material includes preparations of polypeptides having less than about 30%, 20%, 10%, or 5% (by dry weight) of non-herbicide resistance polypeptide (also referred to herein as a "contaminating protein"). In the present invention, "herbicide resistance protein" is intended a polypeptide that it resistant to herbicidal glutamine synthetase inhibitors. In some embodiments, the herbicide resistance protein confers resistance to glufosinate. Fragments, biologically active portions, and variants thereof are also provided, and may be used to practice the methods of the present invention.

"Fragments" or "biologically active portions" include polypeptide fragments comprising a portion of an amino acid sequence encoding an herbicide resistance protein and that retains herbicide resistance activity. A biologically active portion of an herbicide resistance protein can be a polypeptide that is, for example, 10, 25, 50, 100 or more amino acids in length. Such biologically active portions can be prepared by recombinant techniques and evaluated for herbicide resistance activity.

By "variants" is intended proteins or polypeptides having an amino acid sequence that is at least about 60%, 65%, about 70%, 75%, about 80%, 85%, 90%, 91%, 92%, 93%, 94%, 95%, 96%, 97%, 98% or 99% identical to SEQ ID NO:2, wherein one or more amino acids corresponding to positions 125 to 175 and/or positions 200-250 of SEQ ID NO:2 has been modified such that the polypeptide is resistant to herbicidal glutamine synthetase inhibitor, or wherein one or more amino acids has been modified such that there is a loss of one or more adenylylation sites in the resulting polypeptide. This protein may be altered in various ways including amino acid substitutions, deletions, truncations, and insertions of one or more amino acids of SEQ ID NO:4, 6, 8, 10, 12, 14, 16, 18, 20, 22, 24, 26, 28, 30, 32, 34, 36, 38, 40, 42, 44, or 46, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100 or more amino acid substitutions, deletions or insertions. One of skill in the art will recognize that these values can be appropriately adjusted to determine corresponding identity of polypeptides encoded by two polynucleotides by taking into account codon degeneracy, amino acid similarity, reading frame positioning, and the like.

For example, conservative amino acid substitutions may be made at one or more nonessential amino acid residues. A "nonessential" amino acid residue is a residue that can be modified from the wild-type sequence of a polypeptide without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in nonconserved regions that retain function. In general, such substitutions would not be made for conserved amino acid residues, or for amino acid residues residing within a conserved motif, where such residues are essential for polypeptide activity. However, one of skill in the art would understand that functional variants may have minor conserved or non-conserved alterations or modifications in the conserved residues.

Variants also include polypeptides encoded by a polynucleotide that hybridizes to the polynucleotide encoding a polypeptide that is resistant to herbicidal glutamine synthetase inhibitor, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retain herbicide resistance activity. Methods for measuring herbicide resistance activity are well known in the art. See, for example, U.S. Pat. Nos. 5,098,838 and 5,145,777, each of which are herein incorporated by reference in their entirety.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may lead to generation of variants that confer herbicide resistance. These herbicide resistance proteins are encompassed in the present invention and may be used in the methods of the present invention.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

F. Polynucleotide Constructs

The polynucleotides employed in the methods and compositions of the invention may be modified to obtain or enhance expression in plant cells. The polynucleotides encoding the polypeptides of the invention may be provided in expression cassettes for expression in the plant of interest. A "plant expression cassette" includes a DNA construct that is capable of resulting in the expression of a polynucleotide in a plant cell. The cassette can include in the 5'-3' direction of transcription, a transcriptional initiation region (i.e., promoter) operably-linked to one or more polynucleotides of interest, and a translation and transcriptional termination region (i.e., termination region) functional in plants. The cassette may additionally contain at least one additional polynucleotide to be introduced into the organism, such as a selectable marker gene. Alternatively, the additional polynucleotide(s) can be provided on multiple expression cassettes. Such an expression cassette is provided with a plurality of restriction sites for insertion of the polynucleotide(s) to be under the transcriptional regulation of the regulatory regions. "Heterologous" generally refers to the polynucleotide or polypeptide that is not endogenous to the cell or is not endogenous to the location in the native genome in which it is present, and has been added to the cell by infection, transfection, microinjection, electroporation, microprojection, or the like. By "operably linked" is intended a functional linkage between two polynucleotides. For example, when a promoter is operably linked to a DNA sequence, the promoter sequence initiates and mediates transcription of the DNA sequence. It is recognized that operably linked polynucleotides may or may not be contiguous and, where used to reference the joining of two polypeptide coding regions, the polypeptides are expressed in the same reading frame.

The promoter may be any polynucleotide sequence which shows transcriptional activity in the chosen plant cells, plant parts, or plants. The promoter may be native or analogous, or foreign or heterologous, to the plant host and/or to the DNA sequence of the invention. Where the promoter is "native" or "analogous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds (1987) *Nucleic Acids Res.* 15:2343-2361. Also, the location of the promoter relative to the transcription start may be optimized. See, e.g., Roberts et al. (1979) *Proc. Natl. Acad. Sci. USA*, 76:760-764. Many suitable promoters for use in plants are well known in the art.

For instance, suitable constitutive promoters for use in plants include: the promoters from plant viruses, such as the peanut chlorotic streak caulimovirus (PClSV) promoter (U.S. Pat. No. 5,850,019); the 35S promoter from cauliflower mosaic virus (CaMV) (Odell et al. (1985) *Nature* 313:810-812); promoters of Chlorella virus methyltransferase genes (U.S. Pat. No. 5,563,328) and the full-length transcript promoter from figwort mosaic virus (FMV) (U.S. Pat. No. 5,378,619); the promoters from such genes as rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); maize H3 histone (Lepetit et al. (1992) *Mol. Gen. Genet.* 231:276-285 and Atanassova et al. (1992) *Plant J.* 2(3):291-300); *Brassica napus* ALS3 (PCT application WO 97/41228); and promoters of various *Agrobacterium* genes (see U.S. Pat. Nos. 4,771,002; 5,102,796; 5,182,200; and 5,428,147).

Suitable inducible promoters for use in plants include: the promoter from the ACE1 system which responds to copper (Mett et al. (1993) *PNAS* 90:4567-4571); the promoter of the maize In2 gene which responds to benzenesulfonamide herbicide safeners (Hershey et al. (1991) *Mol. Gen. Genetics* 227:229-237 and Gatz et al. (1994) *Mol. Gen. Genetics* 243: 32-38); and the promoter of the Tet repressor from Tn10 (Gatz et al. (1991) *Mol. Gen. Genet.* 227:229-237). Another inducible promoter for use in plants is one that responds to an inducing agent to which plants do not normally respond. An exemplary inducible promoter of this type is the inducible promoter from a steroid hormone gene, the transcriptional activity of which is induced by a glucocorticosteroid hormone (Schena et al. (1991) *Proc. Natl. Acad. Sci. USA* 88:10421) or the recent application of a chimeric transcription activator, XVE, for use in an estrogen receptor-based inducible plant expression system activated by estradiol (Zuo et al. (2000) *Plant J.*, 24:265-273). Other inducible promoters for use in plants are described in EP 332104, PCT WO 93/21334 and PCT WO 97/06269 which are herein incorporated by reference in their entirety. Promoters composed of portions of other promoters and partially or totally synthetic promoters can also be used. See, e.g., Ni et al. (1995) *Plant J.* 7:661-676 and PCT WO 95/14098 describing such promoters for use in plants.

The promoter may include, or be modified to include, one or more enhancer elements. In some embodiments, the promoter may include a plurality of enhancer elements. Promoters containing enhancer elements provide for higher levels of transcription as compared to promoters that do not include them. Suitable enhancer elements for use in plants include the PClSV enhancer element (U.S. Pat. No. 5,850,019), the CaMV 35S enhancer element (U.S. Pat. Nos. 5,106,739 and 5,164,316) and the FMV enhancer element (Maiti et al. (1997) *Transgenic Res.* 6:143-156). See also PCT WO 96/23898.

Often, such constructs can contain 5' and 3' untranslated regions. Such constructs may contain a "signal sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the construct can be engineered to contain a signal peptide to facilitate transfer of the peptide to the endoplasmic reticulum. By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that, when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. It may also be preferable to engineer the plant expression cassette to contain an intron, such that mRNA processing of the intron is required for expression.

By "3' untranslated region" is intended a polynucleotide located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a polynucleotide located upstream of a coding sequence.

Other upstream or downstream untranslated elements include enhancers. Enhancers are polynucleotides that act to increase the expression of a promoter region. Enhancers are well known in the art and include, but are not limited to, the SV40 enhancer region and the 35S enhancer element.

The termination region may be native with the transcriptional initiation region, may be native with the sequence of the present invention, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

In one aspect of the invention, synthetic DNA sequences are designed for a given polypeptide, such as the polypeptides of the invention. Expression of the open reading frame of the synthetic DNA sequence in a cell results in production of the polypeptide of the invention. Synthetic DNA sequences can be useful to simply remove unwanted restriction endonuclease sites, to facilitate DNA cloning strategies, to alter or remove any potential codon bias, to alter or improve GC content, to remove or alter alternate reading frames, and/or to alter or remove intron/exon splice recognition sites, polyadenylation sites, Shine-Delgarno sequences, unwanted promoter elements and the like that may be present in a native DNA sequence. It is also possible that synthetic DNA sequences may be utilized to introduce other improvements to a DNA sequence, such as introduction of an intron sequence, creation of a DNA sequence that in expressed as a protein fusion to organelle targeting sequences, such as chloroplast transit peptides, apoplast/vacuolar targeting peptides, or peptide sequences that result in retention of the resulting peptide in the endoplasmic reticulum. Synthetic genes can also be synthesized using host cell-preferred codons for improved expression, or may be synthesized using codons at a host-preferred codon usage frequency. See, for example, Campbell and Gowri (1990) *Plant Physiol.* 92:1-11; U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the polynucleotides of interest are targeted to the chloroplast for expression. In this manner, where the polynucleotide of interest is not directly inserted into the chloroplast, the expression cassette will additionally contain a polynucleotide encoding a transit peptide to direct the nucleotide of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The polynucleotides of interest to be targeted to the chloroplast may be optimized for expression in the chloroplast to account for differences in codon usage between the plant nucleus and this organelle. In this manner, the polynucleotides of interest may be synthesized using chloroplast-preferred codons. See, for example, U.S. Pat. No. 5,380,831, herein incorporated by reference.

This plant expression cassette can be inserted into a plant transformation vector. By "transformation vector" is intended a DNA molecule that allows for the transformation of a cell. Such a molecule may consist of one or more expression cassettes, and may be organized into more than one vector DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a polynucleotide construct designed for transfer between different host cells. "Expression vector" refers to a vector that has the ability to incorporate, integrate and express heterologous DNA sequences or fragments in a foreign cell.

The plant transformation vector comprises one or more DNA vectors for achieving plant transformation. For example, it is a common practice in the art to utilize plant transformation vectors that comprise more than one contiguous DNA segment. These vectors are often referred to in the art as binary vectors. Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "polynucleotide of interest" (a polynucleotide engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker sequence and the sequence of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science,* 5:446-451). Several types of *Agrobacterium* strains (e.g., LBA4404, GV3101, EHA101, EHA105, etc.) can be used for plant transformation. The second plasmid vector is not necessary for introduction of polynucleotides into plants by other methods such as microprojection, microinjection, electroporation, polyethylene glycol, etc.

G. Expression of Herbicide Tolerance and Insect Tolerance Genes

The plants tolerant of inhibitors of glutamine synthetase described herein may further exhibit resistance or tolerance to one or more herbicides (in addition to GS-inhibitors) and/or one or more pests such as insects, nematodes or fungi. In some embodiments, one or more of the plants described herein exhibit tolerance or resistance to one or more herbicides in addition to GS-inhibitors. A number of genes are available, both transgenic and non-transgenic, that confer herbicide resistance. Genes conferring resistance to an herbicide that inhibits the growing point or meristem, such as an imidazalinone or a sulfonylurea can be suitable. Exemplary genes in this category code for mutant ALS and AHAS enzymes as described, for example, in U.S. Pat. Nos. 5,767,366 and 5,928,937. U.S. Pat. Nos. 4,761,373 and 5,013,659 are directed to plants resistant to various imidazolinone or sulfonamide herbicides.

Genes for resistance to glyphosate, such as glyphosate resistance EPSP synthase genes, are particularly useful in the methods and compositions disclosed herein. See, for example, U.S. patent application Ser. Nos. 11/500,718, 11/185,342, 11/185,560, 11/315,678, 11/312,866, 11/400,598, 11/605,824, and 11/651,752, U.S. Pat. No. 4,940,835 and U.S. Pat. No. 4,769,061, each of which are herein incorporated by reference in their entirety. U.S. Pat. No. 5,554,798 discloses transgenic glyphosate resistant maize plants, which resistance is conferred by an altered 5-enolpyruvyl-3-phosphoshikimate (EPSP) synthase gene.

Genes for resistance to phosphono compounds such as glufosinate ammonium or phosphinothricin, and pyridinoxy or phenoxy propionic acids and cyclohexones are also suitable. See European application No. 0 242 246. See also, U.S. Pat. Nos. 5,879,903, 5,276,268 and 5,561,236. Other suitable herbicides include those that inhibit photosynthesis, such as a triazine and a benzonitrile (nitrilase) (see U.S. Pat. No. 4,810,648) as well as herbicides such as 2,2-dichloropropionic acid, sethoxydim, haloxyfop, imidazolinone herbicides, sulfonylurea herbicides, triazolopyrimidine herbicides, s-triazine herbicides and bromoxynil.

The insectidal proteins useful for the invention may be expressed in one or more plants disclosed herein. Genes useful for insect or pest resistance include, for example, endotoxin genes encoding toxins identified in *Bacillus* organisms. Genes encoding *Bacillus thuringiensis* (Bt) toxins from several subspecies have been cloned and recombinant clones have been found to be toxic to lepidopteran, dipteran and coleopteran insect larvae. See, for example, U.S. patent application Ser. Nos. 10/782,020, 10/782,141, 10/782,570, 10/783,417, 10/781,979, 10/782,096, 10/926,819, and 11/343,533, each of which are herein incorporated by reference in their entirety. Various other delta-endotoxin genes such as Cry1Aa, Cry1Ab, Cry1Ac, Cry1B, Cry1C, Cry1D, Cry1Ea, Cry1Fa, Cry3A, Cry9A, Cry9C and Cry9B; as well as genes encoding vegetative insecticial proteins such as Vip1, Vip2 and Vip3), are also useful in the methods and compositions disclosed herein. A full list of Bt toxins can be found on the worldwide web at www.lifesci.sussex.ac.uk/home/Neil_Crickmore/Bt/.

H. Plants and Plant Parts

By "plant" is intended whole plants, plant organs (e.g., leaves, stems, roots, etc.), seeds, plant cells, propagules, embryos and progeny of the same. Plant cells can be differentiated or undifferentiated (e.g., callus, suspension culture cells, protoplasts, leaf cells, root cells, phloem cells, pollen). The present invention may be used for introduction of polynucleotides into any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Crop plants are also of interest, including, for example, maize, sorghum, wheat, sunflower, tomato, crucifers, peppers, potato, cotton, rice, soybean, sugarbeet, sugarcane, tobacco, barley, oilseed rape, etc.

This invention is suitable for any member of the monocot plant family including, but not limited to, maize, rice, barley, oats, wheat, sorghum, rye, sugarcane, pineapple, yams, onion, banana, coconut, and dates.

II. Methods

A. Methods to Increase Agronomically Important Properties in Plants

Methods for improving agronomically important plant properties are also provided. The methods comprise introducing into a plant or plant cell a nucleotide sequence encoding a bacteria-derived glutamine synthetase enzyme. By "bacteria-derived glutamine synthetase enzyme" is intended a glutamine synthetase enzyme isolated from a bacterium, or a biologically-active variant or fragment thereof. In one embodiment, the nucleotide sequence comprises a variant of SEQ ID NO:1, wherein the variant polynucleotide is at least 80% identical to SEQ ID NO:1. In another embodiment, the nucleotide sequence comprises a polynucleotide having at least one modification between amino acids 125 to 175, at least one modification between amino acids 200 to 250 corresponding to SEQ ID NO:2, or at least one modification that results in the loss of one or more adenylylation sites. In another embodiment, the polynucleotide is selected from the group consisting of SEQ ID NOS:3, 5, 7, 9, 11, 13, 15, 17, 19, 21, 23, 25, 27, 29, 31, 33, 35, 37, 39, 41, 43, 45, or 47. Expression of these enzymes in a plant results in enhanced nitrogen assimilation and/or utilization capacities of the plant, as well as improved agronomic characteristics such as plant yield.

As defined herein, the "yield" of the plant refers to the quality and/or quantity of biomass produced by the plant. By "biomass" is intended any measured plant product. An increase in biomass production is any improvement in the yield of the measured plant product. The method comprises introducing into a plant of interest a polynucleotide encoding a glutamine synthetase enzyme derived from bacteria. In one embodiment, the glutamine synthetase enzyme is resistant to herbicidal glutamine synthetase inhibitor, although resistance is not necessary to achieve enhanced agronomic properties. In another embodiment, the glutamine synthetase enzyme has increased enzymatic activity relative to a control glutamine synthetase enzyme as defined infra.

While not bound by any particular theory or mechanism, expression of a bacteria-derived glutamine synthetase enzyme in a plant may lead to enhanced activity (resulting in enhanced yield and/or nitrogen utilization) compared to a plant derived glutamine synthetase (including the endogenous glutamine synthetase in which the bacteria-derived synthetase is heterologously expressed) due to different regulatory mechanisms for the bacterial GS compared to the plant GS. The enzymatic activity of bacterial GS enzymes is regulated in a manner that is different than plant GS enzymes (Moorhead and Smith (2003) *Plant Physiol* 133:492-498, herein incorporated by reference in its entirety). In bacterial systems, the nitrogen status in the cell is sensed by the PII protein. Under conditions of high nitrogen, PII initiates a signal cascade the causes the adenylylation of individual subunits of bacterial GS enzymes. Adenylylation of bacterial GS causes a decrease in enzymatic activity. Thus, the enzymatic activity of bacterial GS enzymes can be modulated by the extent of adenylylation of the GS dodecamer. In contrast, since plants do not possess an analogous PII signal cascade, it is unlikely that plant cells would cause adenylylation of a bacterial GS enzyme.

The development of plant varieties that use nitrogen more efficiently will reduce the need for excessive inputs of nitrogen, save production costs for farmers, benefit farmers in developing countries who do not have access to fertilizer inputs, and reduce pollution associated with the application of excessive nitrogen fertilizers. Additionally, providing plants with increased yield as a result of an improved glutamine synthetase activity has several commercial applications. For example, increasing plant leaf biomass may increase the yield of leafy vegetables for human or animal consumption. Furthermore, increasing leaf biomass can be used to increase production of plant-derived pharmaceutical or industrial products.

According to the present invention, plants expressing a bacteria-derived glutamine synthetase may exhibit improved nitrogen contents, altered amino acid or protein compositions, vigorous growth characteristics, increased vegetative yields or better seed yields and qualities. These plants may be identified by examining any of following parameters: 1) the rate of growth, measured in terms of rate of increase in fresh or dry weight; 2) vegetative yield of the mature plant, in terms of fresh or dry weight; 3) the seed or fruit yield; 4) the seed or fruit weight; 5) the total nitrogen content of the plant; 6) the total nitrogen content of the fruit or seed; 7) the free amino acid content of the plant; 8) the free amino acid content of the fruit or seed; 9) the total protein content of the plant; and 10) the total protein content of the fruit or seed. The procedures and methods for examining these parameters are well known to those skilled in the art. These methods may involve enzymatic assays and immunoassays to measure enzyme/protein levels; assays to measure the amino acid composition, free amino acid pool or total nitrogen content of various plant tissues; measurement of growth rates in terms of fresh weight gains over time; or measurement of plant yield in terms of total dry weight and/or total seed weight.

The measurement can be in vitro in a cell expressing the glutamine synthetase enzyme or in plant material collected from a plant expressing the enzyme, or may be in vivo in a plant expressing the enzyme. The screening can be performed under conditions of nitrogen deficiency or under nitrogen non-limiting conditions. Nitrogen conditions are described with respect to the available nitrogen nutrient. Nitrogen deficient conditions include those that cause the growth of a control plant to cease or to be so diminished as to significantly reduce the size or quality of the control plant. Nitrogen non-limiting conditions include those having sufficient amounts of nitrogen nutrients to sustain healthy plant growth. Nitrogen conditions which constitute non-limiting or deficient are known in the art for the majority, if not all, plant varieties of interest. Additional guidance may be found in, for example, Hewitt (1966) *Sand and Water Culture Methods Used in the Study of Plant Nutrition,* 2nd ed., Farnham Royal (Bucks), Commonwealth Agricultural Bureaux; and, Hewitt (1975) *Plant Mineral Nutrition*, London, English University Press.

For the purposes of the present invention, an improvement in any of the above characteristics is relative to a control plant or plant cell grown under similar conditions. A "control" plant or plant cell is one that expresses a glutamine synthetase enzyme that is not a bacteria-derived glutamine synthetase. An improvement in any of these parameters can comprise any increase including, but not limited to, at least a 1% increase, at least a 3% increase, at least a 5% increase, at least a 10% increase, at least a 20% increase, at least a 30%, at least a 50%, at least a 70%, at least a 100% or a greater increase in one or more of these parameters.

In various embodiments, the bacteria-derived GS enzyme has improved enzymatic activity when compared to other bacteria- or plant-derived glutamine synthetase enzymes. A glutamine synthetase enzyme with improved activity is one with activity above the activity of the AGS1 enzyme disclosed herein as SEQ ID NO:2. In some embodiments, the bacteria-derived GS enzyme has improved activity due to a functional mutation in the enzyme, rather than overexpression of the enzyme in a system. Activity can be measured by any method known in the art. Unless otherwise specified, the bacteria-derived glutamine synthetase enzyme with improved activity is one that has improved activity when compared to the activity of the same or substantially the same concentration of SEQ ID NO:2 when expressed in a bacterial system (e.g., in *E. coli*).

B. Plant Transformation

Methods of the invention involve introducing one or more polynucleotides into a plant. By "introducing" is intended to present to the plant the polynucleotide in such a manner that the polynucleotide gains access to the interior of a cell of the plant. The methods of the invention do not require that a particular method for introducing a polynucleotide into a plant be used, only that the polynucleotide gains access to the interior of at least one cell of the plant.

Introduction of a polynucleotide into plant cells is accomplished by one of several techniques known in the art, including but not limited to electroporation or chemical transformation (See, for example, Ausubel, ed. (1994) *Current Protocols in Molecular Biology* (John Wiley and Sons, Inc., Indianapolis, Ind.). Markers conferring resistance to toxic substances are useful in identifying transformed cells (having taken up and expressed the test polynucleotide sequence) from non-transformed cells (those not containing or not expressing the test polynucleotide sequence). In one aspect of the invention, the polynucleotide sequences disclosed herein are useful as a marker to assess introduction of DNA into plant cells. Methods for detecting the presence of a transgene in a plant, plant organ (e.g., leaves, stems, roots, etc.), seed, plant cell, propagule, embryo or progeny of the same are well known in the art. "Transgenic plants" or "transformed plants" or "stably transformed" plants, cells, tissues or seed refer to plants that have incorporated or integrated exogenous polynucleotides into the plant cell. By "stable transformation" is intended that the polynucleotide construct introduced into a plant integrates into the genome of the plant and is capable of being inherited by progeny thereof.

In general, plant transformation methods involve transferring heterologous DNA into target plant cells (e.g., immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent (i.e., herbicide). The shoots are then transferred to a selective rooting medium for recovering rooted shoot or plantlet. The transgenic plantlet then grow into mature plants and produce fertile seeds (e.g., Hiei et al. (1994) *Plant J.* 6:271-282; Ishida et al. (1996) *Nat. Biotechnol.* 14:745-750). A general description of the techniques and methods for generating transgenic plants is found in Ayres and Park (1994) *CRC Crit. Rev. Plant Sci.* 13:219-239 and Bommineni and Jauhar (1997) *Maydica* 42: 107-120. Since the transformed material contains many cells, both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Molecular and biochemical methods may be used to confirm the presence of the integrated polynucleotide(s) of interest in the genome of transgenic plant.

Generation of transgenic plants may be performed by one of several methods, including but not limited to introduction of heterologous DNA by *Agrobacterium* into plant cells (Agrobacterium-mediated transformation), bombardment of plant cells with heterologous foreign DNA adhered to particles, and various other non-particle direct-mediated methods (e.g., Hiei et al. (1994) *Plant J.* 6:271-282; Ishida et al. (1996) *Nat. Biotechnol.* 14:745-750; Ayres and Park (1994) *CRC Crit. Rev. Plant Sci.* 13:219-239; Bommineni and Jauhar (1997) *Maydica* 42:107-120) to transfer DNA.

There are three common methods of transforming plant cells with *Agrobacterium*. The first method is co-cultivation of *Agrobacterium* with cultured isolated protoplasts. This method requires an established culture system that allows culturing protoplasts and plant regeneration from cultured protoplasts. The second method is transformation of cells or tissues with *Agrobacterium*. This method requires (a) that the plant cells or tissues can be transformed by *Agrobacterium* and (b) that the transformed cells or tissues can be induced to regenerate into whole plants. The third method is transformation of seeds, apices or meristems with *Agrobacterium*. This method requires micropropagation.

The efficiency of transformation by *Agrobacterium* may be enhanced by using a number of methods known in the art. For example, the inclusion of a natural wound response molecule such as acetosyringone (AS) to the *Agrobacterium* culture has been shown to enhance transformation efficiency with *Agrobacterium tumefaciens* (Shahla et al. (1987) *Plant Molec. Biol.* 8:291-298). Alternatively, transformation efficiency may be enhanced by wounding the target tissue to be transformed. Wounding of plant tissue may be achieved, for example, by punching, maceration, bombardment with microprojectiles, etc. See, for example, Bidney et al. (1992) *Plant Molec. Biol.* 18:301-313.

In still further embodiments, the plant cells are transfected with vectors via particle bombardment (i.e., with a gene gun). Particle mediated gene transfer methods are known in the art, are commercially available, and include, but are not limited to, the gas driven gene delivery instrument described in U.S. Pat. No. 5,584,807, the entire contents of which are herein incorporated by reference. This method involves coating the polynucleotide sequence of interest onto heavy metal particles, and accelerating the coated particles under the pressure of compressed gas for delivery to the target tissue.

Other particle bombardment methods are also available for the introduction of heterologous polynucleotide sequences into plant cells. Generally, these methods involve depositing the polynucleotide sequence of interest upon the surface of small, dense particles of a material such as gold, platinum, or tungsten. The coated particles are themselves then coated onto either a rigid surface, such as a metal plate, or onto a carrier sheet made of a fragile material such as mylar. The coated sheet is then accelerated toward the target biological tissue. The use of the flat sheet generates a uniform spread of accelerated particles that maximizes the number of cells receiving particles under uniform conditions, resulting in the introduction of the polynucleotide sample into the target tissue.

Specific initiation signals may also be used to achieve more efficient translation of sequences encoding the polypeptide of interest. Such signals include the ATG initiation codon and adjacent sequences. In cases where sequences encoding the polypeptide of interest, its initiation codon, and upstream sequences are inserted into the appropriate expression vector, no additional transcriptional or translational control signals may be needed. However, in cases where only the coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers that are appropriate for the particular cell system that is used, such as those described in the literature (Scharf et al. (1994) *Results Probl. Cell Differ.* 20:125).

Cells that have been transformed with a polynucleotide encoding a polypeptide domain of the invention may be grown into plants in accordance with conventional ways. See, for example, McCormick et al. (1986) *Plant Cell Rep.* 5:81-84. These plants may then be grown, and pollinated with either the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide encoding a polypeptide domain of the invention, for example, an expression cassette of the invention, stably incorporated into their genome.

C. Evaluation of Plant Transformation

Following introduction of DNA into plant cells, the transformation or integration of the polynucleotide into the plant genome is confirmed by various methods such as analysis of polynucleotides, polypeptides and metabolites associated with the integrated sequence.

PCR analysis is a rapid method to screen cells, tissue or shoots for the presence of incorporated gene at the earlier stage before transplanting into the soil (Sambrook and Russell (2001) *Molecular Cloning: A Laboratory Manual* (Cold Spring Harbor Laboratory Press, Cold Spring Harbor, N.Y.)). PCR is carried out using oligonucleotide primers specific to the nucleotide of interest or *Agrobacterium* vector background, etc.

Introduction of DNA may be confirmed by Southern blot analysis of genomic DNA (Sambrook and Russell (2001) supra). In general, total DNA is extracted from the cell or organism, digested with appropriate restriction enzymes, fractionated in an agarose gel and transferred to a nitrocellulose or nylon membrane. The membrane or "blot" is then probed with, for example, radiolabeled $^{32}$P target DNA fragment to confirm the integration of introduced DNA into the plant genome according to standard techniques (Sambrook and Russell (2001) supra).

In Northern analysis, RNA is isolated from specific tissues of the cell or organism, fractionated in a formaldehyde agarose gel and blotted onto a nylon filter according to standard procedures that are routinely used in the art (Sambrook and Russell (2001) supra). Expression of RNA encoded by the polynucleotide of the present invention is then tested by hybridizing the filter to a radioactive probe derived from the sequence of interest by methods known in the art (Sambrook and Russell (2001) supra).

Western blot, biochemical assays and the like may be carried out on the transgenic plants to determine the presence of a polypeptide(s) encoded by the polynucleotide(s) of interest by standard procedures (Sambrook and Russell (2001) supra) using antibodies that bind to one or more epitopes present on the herbicide resistance polypeptide.

D. Methods for Selectively Controlling Weeds in a Crop Field

Methods for selectively controlling weeds in a field containing a plant are also provided. In one embodiment, the plant seeds or plants are resistant to herbicidal glutamine synthetase inhibitors as a result of a polynucleotide of the present invention being inserted into the plant seed or plant. In specific methods, the plant is treated with an effective concentration of an herbicide, where the herbicide application results in a selective control of weeds or other untransformed plants. By "effective concentration" is intended the concentration which controls the growth or spread of weeds or other untransformed plants without significantly affecting the herbicide-resistant plant or plant seed. Thus, the amount may be small enough to simply retard or suppress the growth or development, or the amount may be large enough to irreversibly destroy the sensitive plant. Such effective concentrations for herbicides of interest are generally known in the art. The herbicide may be applied either pre- or post emergence in accordance with usual techniques for herbicide application to fields comprising plants or plant seeds which have been rendered resistant to the herbicide.

The following examples are offered by way of illustration and not by way of limitation.

EXPERIMENTAL

Example 1

Glufosinate Resistant Strain

A glufosinate resistant bacterial strain (ATX 20345) was isolated from a soil sample via a soil suspension by placing approximately 0.01 grams soil in 500 µl sterile water. The soil suspension was vortexed, and 20 µl was used to inoculate a 2.5 ml minimal medium culture supplemented with 5 mM glufosinate (Riedel-de Haën, available through Sigma-Aldrich, St. Louis, Mo.). The minimal medium contains the following ingredients (per 1 liter): 10 grams sucrose, 1 ml 0.8M $MgSO_4$, 1 ml 0.1M $CaCl_2$, 1 ml trace elements, 2.38 grams $KH_2PO_4$, 5.64 grams $K_2HPO_4$. The pH is adjusted to 7.0, and the solution is sterilized with a 0.2 µm filter. Trace elements consist of (per 100 ml) 0.1 g $FeSO_4.7H_2O$, 0.5 mg $CuSO_4.5H_2O$, 1.0 mg $H_3BO_3$, 1.0 mg $MnSO_4.5H_2O$, 7.0 mg $ZnSO_4.7H_2O$, 1.0 mg $MoO_3$, 4.0 g KCl. No additional nitrogen source was provided in the medium. Cultures were grown at 21° C. on a rotary shaker for 3 days then transferred to fresh minimal medium containing 5 mM glufosinate and incubated at 21° C. After 2 days, the cultures were used to inoculate fresh minimal medium with 5 mM glufosinate. After 2 days, the cultures were plated onto Luria Bertani (LB) agar and then restruck for isolation. ATX 20345 was selected for its ability to grow in the presence of 5 mM glufosinate. Colonies on LB agar are pinkish-red, raised, circular, and 1-2 mm in diameter. ATX 20345 was typed by fatty acid analysis (as known in the art), and determined to be a strain of *Serratia marcescens*.

ATX 20345 was able to grow to high optical density in the presence of glufosinate under the conditions described above, yet it was unable to grow under the same conditions in the absence of glufosinate. These data suggest that glufosinate is providing nitrogen to the bacterium, either by means of a cleavage of glufosinate to release a usable form of nitrogen or by the supplementation of ammonium in the glufosinate-ammonium complex provided by the supplier. Replacement of glufosinate with ammonium chloride as a nitrogen source, however, permits growth, suggesting ammonium is a suitable nitrogen source for the strain. At higher concentrations (5-50 mM), ATX 20345 grows well through 50 mM and, in fact, appear to grow better as the glufosinate concentration increases from 5 mM up to 50 mM glufosinate. Growth above 50 mM was not tested.

Example 2

Cloning of a Glutamine Synthase from ATX 20345

To obtain the gene(s) responsible for the strain's resistance to glufosinate, a small insert plasmid genomic library was prepared from strain ATX 20345. Genomic DNA was extracted from a fresh, overnight LB culture using SDS, proteinase K cell lysis followed by CTAB/NaCl, phenol-chloroform extractions. Partial digests were performed on the genomic DNA using 0.1 units Sau3A I at 37° C. for 30 minutes followed by the addition of EDTA and incubation at 65° C. for 20 minutes to halt the reaction. Resultant DNA was approximately 4-12 kb in size. The DNA was gel purified, treated with T4 polynucleotide kinase, then ligated into BamH I digested pUC18 vector. Ligations were transformed into DH5α and plated directly on M63 minimal media plates containing 20 mM glufosinate, 100 μg/ml carbenicillin, and 0.1 mM IPTG. After several days, 4 colonies had appeared, tentatively named TKH1-4. They were grown up and plasmid DNA was isolated and analyzed by digestion with EcoR I+Hind III, and Pst I/Sac I to compare inserts. Though all four clones contained inserts, TKH2 and TKH3 were identical by restriction digest analysis, and both contained inserts of approximately 4.9 kb.

To determine whether any of the four clones encoded a glutamine synthetase, all were transformed into the glnA– cell line M5004 (*E. coli* Genetic Stock Center No. 5531, Mayer (1975) *Mol. Gen. Genet.* 137:131-142), along with pUC18 vector control, and plated on LB/carbenicillin. Resultant colonies for each were struck onto M63 minimal plates with or without the addition of glutamine. Only clones containing a functional glutamine synthetase should grow in the absence of glutamine. TKH2 and TKH3 rescued the glnA– phenotype, while TKH1 and TKH4 did not (Table 1). The ability of TKH2 and TKH3 to completely rescue the glnA– phenotype demonstrates that they each contain a functional glutamine synthetase.

TABLE 1

Complementation of glnA-phenotype by THK2 and THK3

| | Growth in glnA-Cells | |
|---|---|---|
| | Glutamine added | No Glutamine |
| TKH1 | +++ | – |
| TKH2 | +++ | +++ |
| TKH3 | +++ | +++ |
| TKH4 | +++ | – |

To reconfirm that TKH2 and TKH3 confer resistance to 20 mM glufosinate, the purified plasmids were retransformed into DH5α cells. pUC18 was retransformed as a negative control. The transformation mixes were plated directly on M63 minimal plates with or without 20 mM glufosinate. While pUC18, TKH2 and TKH3 each grew in the absence of glufosinate, only TKH2 and TKH3 grew in the presence of glufosinate.

Sequencing of the TKH2 and TKH3 plasmid DNA with M13 Forward and M13 Reverse primers, and subsequent analysis of the sequences, revealed that TKH2 and TKH3 are identical clones. Based on complementation, sequence analysis, and demonstration of the ability to confer glufosinate resistance in *E. coli*, we conclude that TKH2 and TKH3 encode an identical glutamine synthetase.

Example 3

Sequence of ags1 Glutamine Synthase

The DNA sequence of the TKH clone was determined (herein referred to as ags1), and an open reading frame with homology to the glutamine synthetase family was identified. This open reading frame was amplified by PCR using high fidelity polymerase, and cloned into pUC19 to yield pAX685. The encoded protein (AGS1) shows high amino acid identity with glutamine synthetases of gram negative bacteria, including *E. coli* (90% amino acid identity), *Erwinia* (94%), *Pantoa* (93%) and *Yersinia* (96%).

Example 4

Mutagenesis of Wild-Type ags1 Glutamine Synthetase

Mutants of the bacterial glutamine synthetase gene ags1 (SEQ ID NO:1) were created by error-prone mutagenesis using the GENEMORPH® Random Mutagenesis kit, and also using oligo-directed mutagenesis as known in the art. However, many methods are available for creating libraries of mutants. The resulting mutants were cloned into a pUC19 vector, electroporated into either XL-1 or DH5 alpha *E. coli* cells, and selected for growth on M63+ agar media containing antibiotic and 2, 10, or 20 mM glufosinate. Twenty-two clones were identified as growing on 20 mM glufosinate, and picked for further analysis.

The sequences of the glufosinate resistant clones were determined. Upon sequence analysis, clones 1 and 15; clones 2 and 3; clones 5 and 6; clones 9, 10, and 12; and clones 16, 17, 19 and 20 were found to be identical. Thus, clones 1, 3, 5, 7, 9, 12, 16, 19, and 20 were not further analyzed.

Clones 2, 10, 15, 17, and 21 were shown to grow on 2, 10, 20, 50, and 100 mM glufosinate minimal M63+ agar media after electroporation into DH5α *E. coli* cells.

Figure 1A:
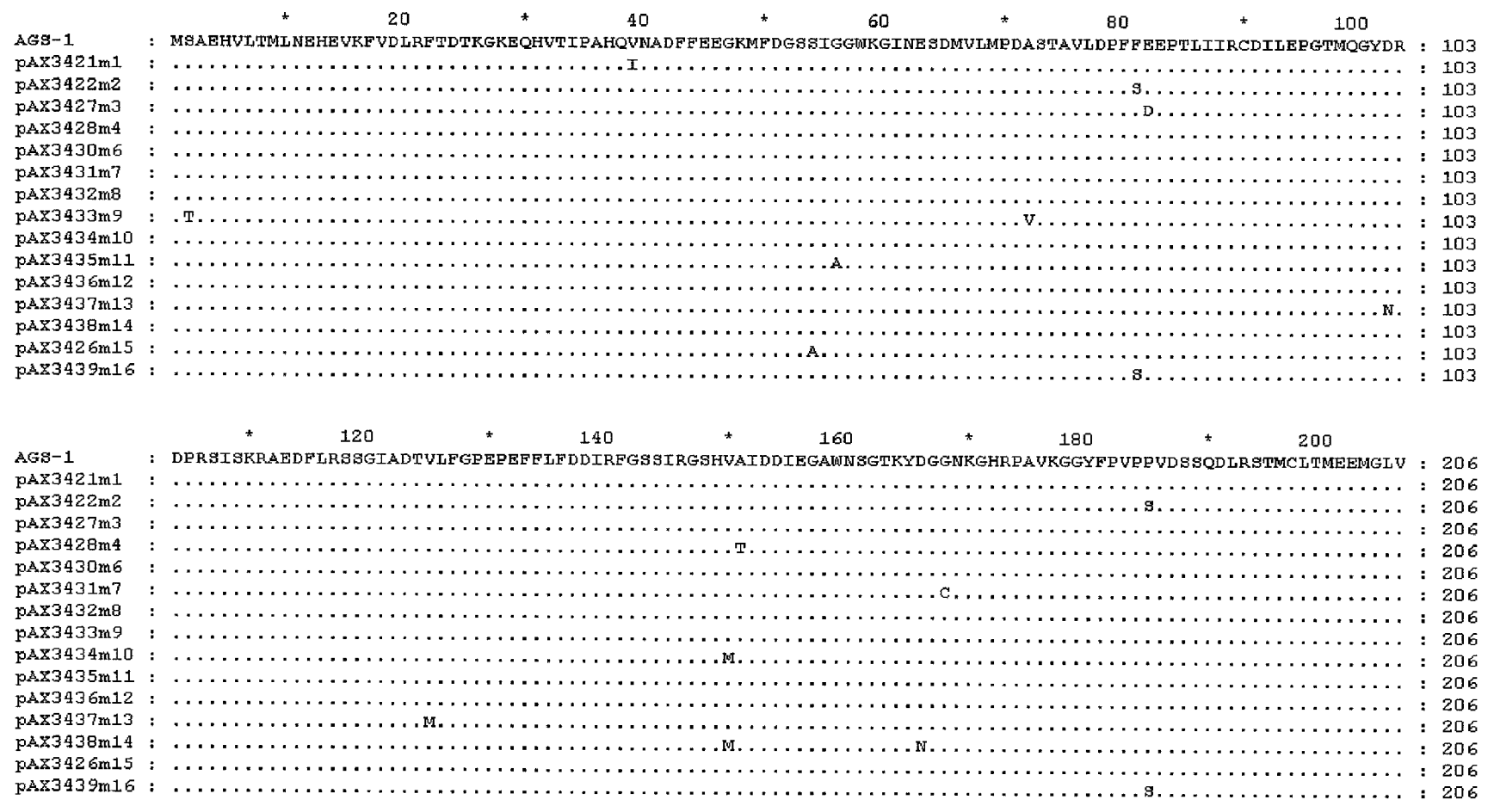
Figure 1B:
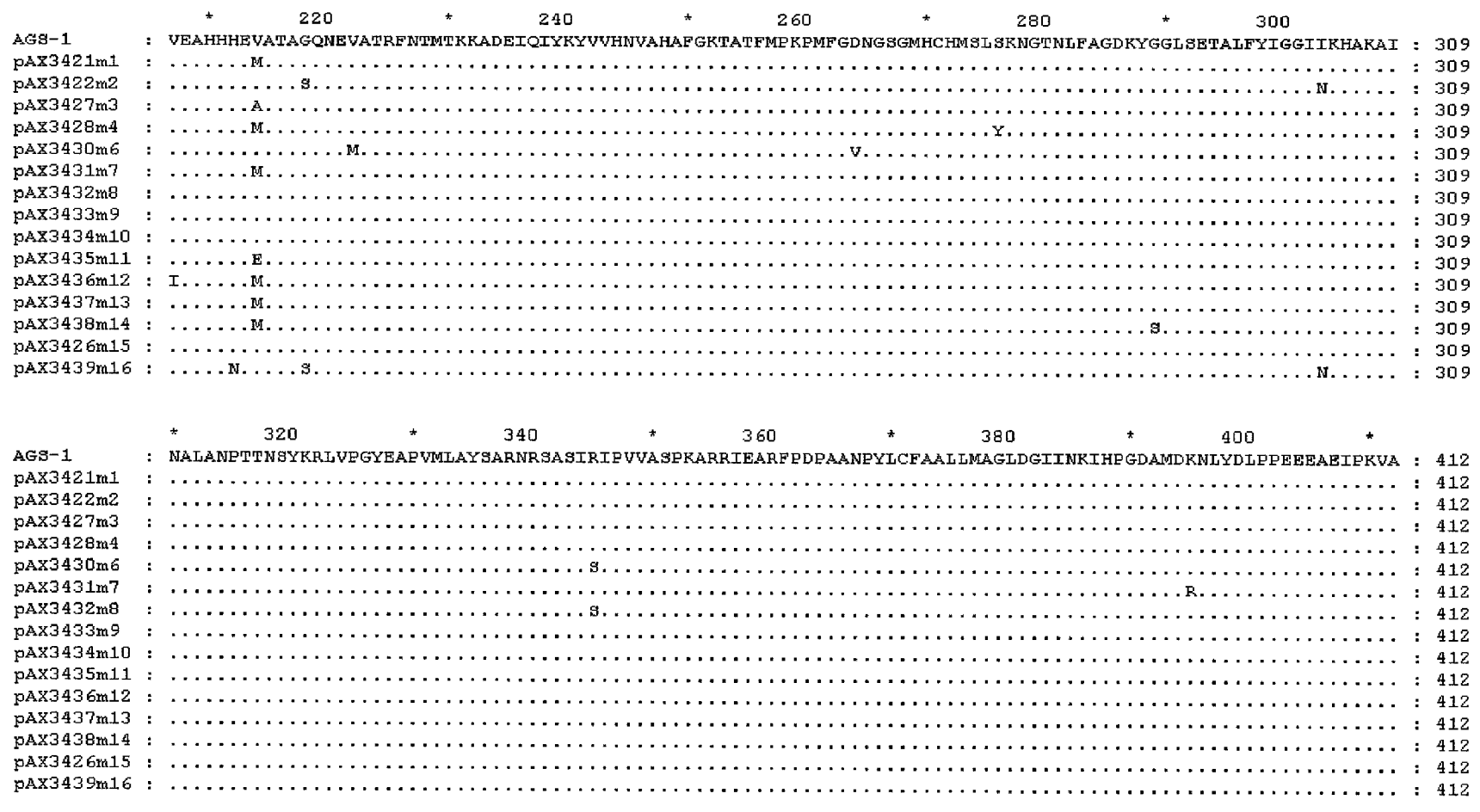

The DNA sequences of the glufosinate resistant clones were translated, and the resulting protein sequences were aligned with the sequence of wild-type AGS1 protein. Amino acid substitutions corresponding to the amino acid position of wild-type AGS1 (SEQ ID NO:2) were noted in these glufosinate-resistant clones. These substitutions are depicted in FIG. 1 and include S2T, V39I, S54A, G56A, A72V, F80S, F81S, E82D, D102M, V125M, V150M, A151T, D166N, G168C, P185S, V207I, H212N, V214M, V214A, V214E, G218S, V222M, D264V, S276Y, G289S, I303N, R345S, K395R, A420V, R447C. Of particular interest are the mutations around the glutamic acid at position 213, which is in the catalytic site of the glutamine synthetase. Another interesting cluster of mutations occurs around amino acid 150.

TABLE 2

Glufosinate Resistant Clones Derived from ags1

| Gene | pAX# | Nucleotide SEQ ID NO: | Amino Acid SEQ ID NO: | Original Clone Designation | Growth on 20 mM Glufosinate | Growth on 100 mM Glufosinate |
|---|---|---|---|---|---|---|
| ags1 (w.t.) | pAX685 | 1 | 2 | N/A | – | – |
| ags1m1 | pAX3421 | 3 | 4 | Clone #2 | +++ | +++ |
| ags1m2 | pAX3422 | 5 | 6 | Pick #6 | +++ | +++ |
| ags1m3 | pAX3427 | 7 | 8 | Clone #4 | +++ | NT |
| ags1m4 | pAX3428 | 9 | 10 | Clone #6 | +++ | NT |
| ags1m6 | pAX3430 | 11 | 12 | Clone #8 | +++ | NT |
| ags1m7 | pAX3431 | 13 | 14 | Clone #10 | +++ | +++ |
| ags1m8 | pAX3432 | 15 | 16 | Clone #11 | +++ | NT |

TABLE 2-continued

Glufosinate Resistant Clones Derived from ags1

| Gene | pAX# | Nucleotide SEQ ID NO: | Amino Acid SEQ ID NO: | Original Clone Designation | Growth on 20 mM Glufosinate | Growth on 100 mM Glufosinate |
|---|---|---|---|---|---|---|
| ags1m9 | pAX3433 | 17 | 18 | Clone #13 | +++ | NT |
| ags1m10 | pAX3434 | 19 | 20 | Clone #14 | +++ | NT |
| ags1m11 | pAX3435 | 21 | 22 | Clone #15 | +++ | +++ |
| ags1m12 | pAX3436 | 23 | 24 | Clone #17 | +++ | +++ |
| ags1m13 | pAX3437 | 25 | 26 | Clone #18 | +++ | NT |
| ags1m14 | pAX3438 | 27 | 28 | Clone #21 | +++ | +++ |
| ags1m15 | pAX3426 | 29 | 30 | Clone #22 | +++ | NT |
| ags1m16 | pAX3439 | 31 | 32 | N/A | +++ | +++ |

NT = not tested

Example 5

Complementation of a Glutamine Synthase Mutant

Clones containing ags1m1 (pAX3421) and ags1m2 (pAX3422) were selected for further work. Both clones were shown to complement ags1 mutant *E. coli* with ags1m1 growing at a faster rate than ags1m2.

Example 6

Kinetics of Glufosinate-Resistant Glutamine Synthases ags1m1 (pAX3421) and ags1m2 (pAX3422) were subcloned into *E. coli* expression vector pRSF1B (Invitrogen) so as to create an N-terminus encoding a 6Xhis tag, purified and characterized kinetically. AGS1m2 ('pick6') had relatively little enzymatic activity in a 5 minute assay as compared with wild type AGS1, but appeared to go to completion overnight. AGS1m1 ('pick 2') was indistinguishable from wild type enzyme in the absence of glufosinate, but showed activity in the presence of 100 uM glufosinate, a concentration which completely inhibited the wild type ags1 glutamine synthetase enzyme.

Example 7

Mutagenesis of ags1m2 ags1m2 was mutagenized by error-prone mutagenesis using GENEMORPH® II Random Mutagenesis kit (Stratagene) according to manufacturer's instructions. Mutagenized PCR product was digested with Sac I and Hind III, and ligated into a pUC vector, similarly digested with Sac I and Hind III. Ligations were transformed into *E. coli* cells, and plated onto M63+ plates containing antibiotic, and 125 mM glufosinate. Clones growing on 125 mM glufosinate plates were retested on 200 mM glufosinate plates, and compared to similar platings of ags1m1 and ags1m2. While cells expressing AGS1m1 and AGS1m2 did not grow on 200 mM glufosinate, a single clone, designated pAX3439, was isolated by virtue of its ability to grow on 200 mM glufosinate plates. The DNA sequence of the ags open reading frame in pAX3439 was sequenced, and the gene designated as ags1m16. The DNA sequence of ags1m16 is represented herein as SEQ ID NO:31, and the amino acid sequence is represented herein as SEQ ID NO:32. AGS1m16 differs from AGS1m2 at a single amino acid at position H212 of the protein, which is modified from Histidine ('H') to Asparagine ('N'), and contains a total of five amino acid changes relative to the wild-type AGS1 (see FIG. 1 and Table 3).

TABLE 3

Variants of ags1

| Gene | Amino acid changes in encoded protein relative to AGS1 |
|---|---|
| ags1(wild-type) | |
| ags1m1 | V39I, V214M |
| ags1m2 | F81S, P185S, G218S, I303N |
| ags1m3 | E82D, V214A |
| ags1m4 | A151T, V214M, S276Y |
| ags1m6 | V222M, D264V, R345S |
| ags1m7 | G168C, V214M, K395R |
| ags1m8 | R345S, R447C |
| ags1m9 | S2T, A72V |
| ags1m10 | V150M |
| ags1m11 | G56A, V214E |
| ags1m12 | V207I, V214M |
| ags1m13 | D102N, V125M, V214M |
| ags1m14 | V150M, D166N, V214M, G289S, A420V |
| ags1m15 | S54A |
| ags1m16 | F81S, P185S, H212N, G218S, I303N |
| ags1m17 | F81S, P185S, H212T, V214A, G218S, I303N |
| ags1m18 | F81S, P185S, H212T, V214S, G218S, I303N |
| ags1m19 | F81S, P185S, H212S, V214A, G218S, I303N |
| ags1m20 | F81S, P185S, H212M, V214H, G218S, I303N |
| ags1m21 | N160S, G167R, V214M |

AGS1m16 confers the most resistance upon *E. coli*. Cells containing AGS1m16 are able to grow at glufosinate concentrations up to 200 mM. Colonies from cells containing AGS1m2, AGS1m11, and AGS1m4 grow more quickly on 50 mM glyphosate than the other variants, except AGS1m16.

Example 8

Variants ags1m17, ags1m18, ags1m19, ags1m20, and ags1m21

Based on knowledge of the GS reaction mechanism known in the art, and alignment of AGS1 with other GS enzymes, one can predict the location of the GS reaction center in AGS1 and variants. ags1(m16) was mutagenized in the region of the protein suggested to be the GS reaction center, and several variants were identified that conferred improved growth on 225 mM glufosinate plates upon the *E. coli* host cells. ags1m17 (SEQ ID NO:33) encodes the AGS1m17 protein (SEQ ID NO:34). ags1m18 (SEQ ID NO:35) encodes the AGS1m18 protein (SEQ ID NO:36). ags1m19 (SEQ ID NO:37) encodes the AGS1m19 protein (SEQ ID NO:38). ags1m20 (SEQ ID NO:39) encodes the AGS1m20 protein (SEQ ID NO:40). Clones expressing AGS1m17, AGS1m18, AGS1m19, or AGS1m20 were all found to be able to grow on plates containing 375 mM glufosinate, whereas no growth of clones expressing AGS1m16 was observed on plates containing 375 mM glufosinate.

ags1m21 (SEQ ID NO:41) encodes the AGS1m21 protein (SEQ ID NO:42). AGS1m21 is a variant of AGS1 that contains a similar amino acid change identified in other variants (V214M), as well as two novel mutations (N160S and G167R). This enzyme was expressed in E. coli, purified, and the kinetic values $K_m$(glutamate) and $K_i$(glufosinate) of the variant measured by enzymatic assay. The mutagenized enzyme was found to possess increased resistance to glufosinate, as shown in the following table.

TABLE 4

Kinetics of AGS1m21

| Enzyme | Km, mM | Ki, uM |
|---|---|---|
| GlnA | 2.7 | nd |
| AGS1 | 3.4 | 13.0 |
| AGS1m21 | 12.0 | 2000 |

Example 9

Removal of Deadenylation Sites from AGS1 and Variants

It is well known in the art (Mehta et al. (2004) J. Biol. Chem. 279:22477-22482, herein incorporated by reference in its entirety) that in bacterial cells, bacterial GS enzymes are often subject to down-regulation by adenylylation of a particular tyrosine residue.

ags1(ad−) (SEQ ID NO:43) encoding the AGS1(AD−) protein (SEQ ID NO:44), is a variant of ags1 in which the putative adenylation site has been removed by mutating the tyrosine at position 398 of AGS1 to a phenylalanine by site directed mutagenesis.

ags1m17(ad−) (SEQ ID NO:45) encoding the AGS1m17 (AD−) protein (SEQ ID NO:46), is a variant of ags1m17 in which the putative adenylation site has been removed by mutating the tyrosine at position 398 of AGS1 to a phenylalanine by site directed mutagenesis.

The unmodified enzyme (AGS1) was compared to AGS1 (AD−) and AGS1m17(AD−) by carrying out enzymatic assays on both enzymes following purification from E. coli. A glutamine synthetase enzyme from E. coli (GlnA) was also tested. The kinetic values obtained for each enzyme are shown in Table 5 below.

TABLE 5

Kinetics of AGS1(AD-)

| Enzyme | $K_m$, mM | $K_i$, µM | $V_{max}$, nmol/min/ µg | $K_{cat}$, sec$^{-1}$ | ($K_{cat}$ * $K_i$)/ $K_m$ | MW (kD) |
|---|---|---|---|---|---|---|
| GlnA (E. coli) | 2.7 | ND | 0.24 | 0.21 | — | 52 |
| AGS1 | 3.4 | 13.0 | 0.10 | 0.08 | 0.32 | 52 |
| AGS1(AD-) | 3.4 | 13.0 | 3.8 | 3.29 | 12.59 | 52 |
| AGS1m17(AD-) | 14.1 | 23,000 | .0078 | 0.07 | 110.04 | |

Example 8

Glufosinate Resistant Clones are Mutated Near the Active Site

A surprising number of variants, and all of the most resistant clones, contain mutations in the active site of the synthetase. The two glutamic acids in the catalytic center (corresponding to positions 213 and 221 of AGS1, SEQ ID NO:2) are key to glutamine synthetase activity. The Valine at position 214 is varied in 13 of the variants, and can be mutated to methionine (M), alanine (A), serine (S), histidine (H) and glutamic acid (E). Three additional variants, including AGS1m16, have modified residues in this region.

Example 9

Identification of Additional Novel Glutamine Synthetase Enzymes that are Resistant to Herbicidal Glutamine Synthetase Using the methods of the invention, one can identify further herbicide resistant glutamine synthetases by searching databases containing glutamine synthetase enzymes, and/or by alignment of the amino acid sequence of glutamine synthetase enzymes and analysis for at least one amino acid substitution within positions corresponding to positions 125 to 175 of SEQ ID NO:2 or between positions 200 to 250 of SEQ ID NO:2. It is understood that some modification of these regions is tolerated in nature without disrupting the herbicide resistance conferring nature of these regions, and are therefore equivalent to the sequences listed herein. Therefore, it is recognized that enzymes having about 80%, about 85%, about 90%, about 95%, 96%, 97%, 98% or 99% homology to the polypeptides of the invention could confer resistance to herbicidal glutamine synthetase inhibitors.

Example 10

Plant Transformation by Particle Bombardment

Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 ml/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 ml/L (of 1 mg/ml stock) 2,4-D). However, media and salts other than DN62A5S are suitable and are known in the art. Embryos are incubated overnight at 25° C. in the dark. However, it is not necessary per se to incubate the embryos overnight. The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to express glutamine synthetase enzymes of the present invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants. The plants are assayed for improved resistance to herbicidal glutamine synthetase inhibitors.

| Materials DN62A5S Media | | |
|---|---|---|
| Components | per liter | Source |
| Chu's N6 Basal Salt Mixture (Prod. No. C 416) | 3.98 g/L | Phytotechnology Labs |
| Chu's N6 Vitamin Solution (Prod. No. C 149) | 1 ml/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 ml/L (of 1 mg/ml Stock) | Sigma |

Adjust the pH of the solution to pH 5.8 with 1N KOH/1N KCl, add Gelrite (Sigma) to 3 g/L, and autoclave. After cooling to 50° C., add 2 ml/L of a 5 mg/ml stock solution of Silver Nitrate (Phytotechnology Labs). Recipe yields about 20 plates.

Example 11

Transformation of Plant Cells by *Agrobacterium*-Mediated Transformation

Ears are best collected 8-12 days after pollination. Embryos are isolated from the ears, and those embryos 0.8-1.5 mm in size are preferred for use in transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors having a sequence of the present invention for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

Example 12

Transgenic Plants Expressing AGS1m16 synags1m16 (SEQ ID NO:47) is an alternate DNA sequence that encodes the AGS1m16 protein (SEQ ID NO:32). synags1m16 was cloned into a shuttle vector to guide overexpression of AGS1m16 in maize. The vector places overexpression of synags1m16 under the control of the Trp5 promoter (U.S. application Ser. No. 11/377,318, filed Mar. 16, 2006 and herein incorporated by reference in its entirety).

Nine transgenic maize plants containing ags1m16 were generated. Protein expression of the AGS1m16 protein was confirmed by Western blot for each of these events. As controls, six events were generated that did not contain ags1m16. Nitrogen use efficiency was evaluated for these events by determining the protein content of leaf samples isolated from the $T_0$ plants after four weeks of growth in the greenhouse.

The protein in leaf samples was quantified as follows: Fifty milligrams of leaf material (fresh weight, no midrib) were freeze-dried for dry weight determination. The dehydrated leaf tissue was then ground in the presence of fresh Milli Q water using a MiniBeadbeater-96™ and 2.3 mm stainless-steel beads. The ground leaf tissue was filtered through a 0.45 µm Polyvinylidene Fluoride (PVDF) filter. Bio-Rad Protein Dye was added to leaf samples diluted in water, and a Bradford protein assay was performed and read in the spectrophotometer at 595 nm vs. internal protein standards included in the assay.

The soluble protein concentrations were divided by the dry weight of each sample to obtain the protein mass per unit dry weight. Surprisingly, the plants containing ags1m16 were found to have an average of 24% higher protein content than the control plants that did not contain ags1m16.

TABLE 6

Increased Protein in AGS1m16 plants

| Event # | Genotype | Total protein (mg/g dry) |
|---|---|---|
| 1 | ags1m16 | 28.1 |
| 2 | ags1m16 | 8.0 |
| 3 | ags1m16 | 13.2 |
| 4 | ags1m16 | 18.4 |
| 5 | ags1m16 | 9.8 |
| 6 | ags1m16 | 13.9 |
| 7 | ags1m16 | 28.6 |
| 8 | ags1m16 | 10.9 |
| 9 | ags1m16 | 20.5 |
| Avg. | | 16.8 |
| C1 | control | 16.0 |
| C2 | control | 14.1 |
| C3 | control | 18.7 |
| C4 | control | 10.1 |
| C5 | control | 13.0 |
| C6 | control | 9.1 |
| Avg. | | 13.5 |

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated or recombinant polynucleotide comprising a variant of SEQ ID NO:1, wherein said variant polynucleotide encodes a polypeptide that has at least 95% sequence identity to SEQ ID NO:2 and that is resistant to inhibition by herbicidal glutamine synthetase inhibitor.

2. The isolated or recombinant polynucleotide of claim 1, wherein said polypeptide comprises at least one modification between amino acids 125 to 175 or at least one modification between amino acids 200 to 250 corresponding to SEQ ID NO:2.

3. The isolated or recombinant polynucleotide of claim 1 selected from the group consisting of SEQ ID NOS:3, 5, 7, 9, 11, 13, 15, 17, 19, 21, 23, 25, 27, 29, 31, 33, 35, 37, 39, 41, and 47.

4. The isolated or recombinant polynucleotide of claim 1, wherein said polynucleotide encodes a polypeptide having at least one modification that results in the loss of an adenylylation site in said polypeptide.

5. The isolated or recombinant polynucleotide of claim 4 that is selected from the group consisting of SEQ ID NO:43 and 45.

6. The isolated or recombinant polynucleotide of claim 1, wherein said herbicidal glutamine synthetase inhibitor comprises glufosinate.

7. The isolated or recombinant polynucleotide of claim 1, wherein said polynucleotide is a synthetic sequence that has been designed for expression in a plant.

8. An isolated or recombinant polynucleotide comprising the nucleotide sequence of SEQ ID NO:1.

9. A vector comprising the polynucleotide of claim 1.

10. The vector of claim 9, further comprising a polynucleotide encoding a heterologous polypeptide.

11. A host cell that contains the vector of claim 9.

12. The host cell of claim 11 that is a bacterial host cell.

13. The host cell of claim 11 that is a plant cell.

14. A transgenic plant comprising the host cell of claim 9.

15. The plant of claim 14, further comprising one or more of a polynucleotide encoding an herbicide tolerance gene or a polynucleotide encoding an insect tolerance gene.

16. The plant of claim 15, wherein said herbicide tolerance gene is an EPSP synthase gene.

17. The plant of claim 15, wherein said insect tolerance gene is an endotoxin.

18. The plant of claim 14, wherein said plant is selected from the group consisting of maize, sorghum, wheat, sunflower, tomato, crucifers, peppers, potato, cotton, rice, soybean, sugarbeet, sugarcane, tobacco, barley, and oilseed rape.

19. A transformed seed comprising the polynucleotide of claim 1.

20. A method for conferring resistance to herbicidal glutamine synthetase inhibitors in a plant comprising transforming said plant with a polynucleotide comprising a variant of SEQ ID NO:1, wherein said variant polynucleotide encodes a polypeptide that has at least 95% sequence identity to SEQ ID NO:2 and that is resistant to inhibition by herbicidal glutamine synthetase inhibitor, and regenerating a transformed plant.

21. The method of claim 20, wherein said polypeptide comprises at least one modification between amino acids 125 to 175 or at least one modification between amino acids 200 to 250 corresponding to SEQ ID NO:2.

22. The method of claim 20 wherein said polynucleotide is selected from the group consisting of SEQ ID NOS:3, 5, 7, 9, 11, 13, 15, 17, 19, 21, 23, 25, 27, 29, 31, 33, 35, 37, 39, 41, and 47.

23. The method of claim 20, wherein said polynucleotide encodes a polypeptide having at least one modification that results in the loss of an adenylylation site in said polypeptide.

24. The method of claim 23, wherein said polynucleotide is selected from the group consisting of SEQ ID NO:43 and 45.

25. The method of claim 20, wherein said herbicidal glutamine synthetase inhibitor comprises glufosinate.

26. The method of claim 20, wherein said method further comprises transformation of said plant with one or more of a polynucleotide encoding an herbicide tolerance gene or a polynucleotide encoding an insect tolerance gene.

27. The method of claim 26, wherein said herbicide tolerance gene is an EPSP synthase gene.

28. The method of claim 26, wherein said insect tolerance gene is an endotoxin.

29. A plant having stably incorporated into its genome a DNA construct comprising a polynucleotide comprising a variant of SEQ ID NO:1, wherein said variant polynucleotide encodes a polypeptide that has at least 95% sequence identity to SEQ ID NO:2 and that is resistant to inhibition by herbicidal glutamine synthetase inhibitor.

30. The plant of claim 29, wherein said polypeptide comprises at least one modification between amino acids 125 to 175 or at least one modification between amino acids 200 to 250 corresponding to SEQ ID NO:2.

31. The plant of claim 29 wherein said polynucleotide is selected from the group consisting of SEQ ID NOS:3, 5, 7, 9, 11, 13, 15, 17, 19, 21, 23, 25, 27, 29, 31, 33, 35, 37, 39, 41, and 47.

32. The plant of claim 29, wherein said polynucleotide encodes a polypeptide having at least one modification that results in the loss of an adenylylation site in said polypeptide.

33. The plant of claim 32, wherein said polynucleotide is selected from the group consisting of SEQ ID NO:43 and 45.

34. The plant of claim 29, wherein said herbicidal glutamine synthetase inhibitor comprises glufosinate.

35. The plant of claim 29, wherein said plant is a plant cell.

36. The plant of claim 29, further comprising one or more of a polynucleotide encoding an herbicide tolerance gene or a polynucleotide encoding an insect tolerance gene.

37. The plant of claim 36, wherein said herbicide tolerance gene is an EPSP synthase gene.

38. The plant of claim 36, wherein said insect tolerance gene is an endotoxin.

39. The plant of claim 29, wherein said plant is selected from the group consisting of maize, sorghum, wheat, sunflower, tomato, crucifers, peppers, potato, cotton, rice, soybean, sugarbeet, sugarcane, tobacco, barley, and oilseed rape.

40. A method for selectively controlling weeds in a field containing a plant having planted seeds or plants comprising the steps of:
  a) planting the seeds or plants which are resistant to herbicidal glutamine synthetase inhibitor as a result of a polynucleotide comprising a variant of SEQ ID NO:1 being inserted into the seed or plant, wherein said variant polynucleotide encodes a polypeptide that has at least 95% sequence identity to SEQ ID NO:2 and that is resistant to inhibition by herbicidal glutamine synthetase inhibitor; and,
  b) applying to the plants and weeds in a field an effective concentration of an herbicidal glutamine synthetase inhibitor to control weeds without significantly affecting the plants.

41. The method of claim 40, wherein said polypeptide comprises at least one modification between amino acids 125 to 175 or at least one modification between amino acids 200 to 250 corresponding to SEQ ID NO:2.

42. The method of claim 40, wherein said polynucleotide is selected from the group consisting of SEQ ID NOS:3, 5, 7, 9, 11, 13, 15, 17, 19, 21, 23, 25, 27, 29, 31, 33, 35, 37, 39, and 47.

43. The method of claim 40, wherein said polynucleotide encodes a polypeptide having at least one modification that results in the loss of an adenylylation site in said polypeptide.

44. The method of claim 43, wherein said polynucleotide is selected from the group consisting of SEQ ID NO:43 and 45.

45. The method of claim 42, wherein said herbicidal glutamine synthetase inhibitor comprises glufosinate.

46. The method of claim 40, wherein said plant or seed further comprises one or more of a polynucleotide encoding an herbicide tolerance gene or a polynucleotide encoding an insect tolerance gene.

47. The method of claim 46, wherein said herbicide tolerance gene is an EPSP synthase gene.

48. The method of claim 46, wherein said insect tolerance gene is an endotoxin.

49. A method for improving yield in a plant comprising introducing into said plant a polynucleotide encoding a glutamine synthetase enzyme derived from a bacterium, wherein said polynucleotide comprises a variant of SEQ ID NO:1 and encodes a polypeptide that has at least 95% sequence identity to SEQ ID NO:2 and that is resistant to inhibition by herbicidal glutamine synthetase inhibitor.

50. The method of claim 49, wherein said polynucleotide is at least 95% identical to a sequence selected from the group consisting of SEQ ID NOS: 3, 5, 7, 9, 11, 13, 15, 17, 19, 21, 23, 25, 27, 29, 31, 33, 35, 37, 39, and 47.

51. The method of claim 49, wherein said polynucleotide encodes a polypeptide having at least one modification that results in the loss of an adenylylation site in said polypeptide.

52. The method of claim 51, wherein said polynucleotide is selected from the group consisting of SEQ ID NO:43 and 45.

53. A method for improving nitrogen utilization in a plant comprising introducing into said plant a polynucleotide encoding a glutamine synthetase enzyme derived from a bacterium, wherein said polynucleotide comprises a variant of SEQ ID NO:1 and encodes a polypeptide that has at least 95% sequence identity to SEQ ID NO:2 and that is resistant to inhibition by herbicidal glutamine synthetase inhibitor.

54. The method of claim 53, wherein said polynucleotide is at least 95% identical to a sequence selected from the group consisting of SEQ ID NOS:3, 5, 7, 9, 11, 13, 15, 17, 19, 21, 23, 25, 27, 29, 31, 33, 35, 37, 39, 41, 43, 45, and 47.

55. The method of claim 53, wherein said polynucleotide encodes a polypeptide having at least one modification that results in the loss of an adenylylation site in said polypeptide.

56. The method of claim 55, wherein said polynucleotide is selected from the group consisting of SEQ ID NO:43 and 45.

57. The isolated or recombinant polynucleotide of claim 3 comprising a polynucleotide 100% identical to a sequence selected from the group consisting of SEQ ID NOS:3, 5, 7, 9, 11, 13, 15, 17, 19, 21, 23, 25, 27, 29, 31, 33, 35, 37, 39, 41, and 47.

58. The method of claim 22 comprising a polynucleotide 100% identical to a sequence selected from the group consisting of SEQ ID NOS:3, 5, 7, 9, 11, 13, 15, 17, 19, 21, 23, 25, 27, 29, 31, 33, 35, 37, 39, 41, and 47.

59. The plant of claim 29 comprising a polynucleotide 100% identical to a sequence selected from the group consisting of SEQ ID NOS:3, 5, 7, 9, 11, 13, 15, 17, 19, 21, 23, 25, 27, 29, 31, 33, 35, 37, 39, 41, and 47.

60. The method of claim 50 comprising a polynucleotide 100% identical to a sequence selected from the group consisting of SEQ ID NOS:3, 5, 7, 9, 11, 13, 15, 17, 19, 21, 23, 25, 27, 29, 31, 33, 35, 37, 39, 41, and 47.

61. The method of claim 54 comprising a polynucleotide 100% identical to a sequence selected from the group consisting of SEQ ID NOS:3, 5, 7, 9, 11, 13, 15, 17, 19, 21, 23, 25, 27, 29, 31, 33, 35, 37, 39, 41, and 47.

62. The recombinant polynucleotide of claim 1, wherein said polynucleotide is operably linked to a promoter that drives expression of said polynucleotide in a plant cell.

* * * * *